US007488588B1

(12) United States Patent
Airaksinen et al.

(10) Patent No.: US 7,488,588 B1
(45) Date of Patent: Feb. 10, 2009

(54) COMPOUNDS RELATED TO OR DERIVED FROM GFR α4 AND THEIR USE

(75) Inventors: Matti Airaksinen, Helsinki (FI); Mart Saarma, Helsinki (FI); Dimitri Poteriaev, Helsinki (FI); Maria Lindahl, Espoo (FI); Tönis Timmusk, Helsinki (FI); Jari Rossi, Helsinki (FI)

(73) Assignee: Licentia Ltd., Helsinki (FI)

( * ) Notice: Subject to any disclaimer, the term of this patent is extended or adjusted under 35 U.S.C. 154(b) by 588 days.

(21) Appl. No.: 10/203,639

(22) PCT Filed: Nov. 14, 2000

(86) PCT No.: PCT/FI00/00994

§ 371 (c)(1),
(2), (4) Date: Nov. 13, 2002

(87) PCT Pub. No.: WO01/62795

PCT Pub. Date: Aug. 30, 2001

(30) Foreign Application Priority Data

Feb. 21, 2000 (FI) .................................. 20000394

(51) Int. Cl.
| C07H 21/02 | (2006.01) |
| C07H 21/04 | (2006.01) |
| C07K 1/00 | (2006.01) |
| C12P 21/06 | (2006.01) |
| C12N 5/00 | (2006.01) |
| C12N 15/00 | (2006.01) |

(52) U.S. Cl. .................... 435/69.1; 536/23.1; 536/23.5; 530/350; 530/351; 435/325; 435/455

(58) Field of Classification Search ................ 435/69.1, 435/320.1, 325, 455; 530/350; 436/23.1
See application file for complete search history.

(56) References Cited

U.S. PATENT DOCUMENTS 6,455,277 B1 * 9/2002 Fox et al. .................... 435/69.1

FOREIGN PATENT DOCUMENTS

| WO | WO 99/50298 | 10/1999 |
| WO | WO 01/02557 | 1/2001 |

OTHER PUBLICATIONS

Lindahl et al JBC 276(12):9344-9351, 2001.*
Ngo, in The Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
PTO sequence search report for SEQ ID No. 10, 11, 12 and 13 in view of US 6455277, conducted Dec. 21, 2005.*
Thompson et al Mol. Cell Neurosci. 1:117-126, 1998.*
Gunn, et al., "The mouse mahogany locus encodes a transmembrane form of human attractin", Nature, vol. 398, Mar. 1999, pp. 152-156.
Enokido, et al., "GFRα4 and the tyrosine kinase Ret from a functional receptor complex for persephin", Current Biology, vol. 8, 1998, pp. 1019-1022.
Dey, et al., "Cloning of a novel murine isoform of the glial cell line-derived neurotrophic factor receptor", Neuro Report, vol. 9, No. 1, Jan. 1998, pp. 37-42.
Masure, et al., "Mammalian GFRα4, a Divergent Member of the GFRα4 Family of Coreceptors for Glial Cell Line-derived Neurotrophic Factor Family Ligands, Is a Receptor for the Neurotrophic Factor Persephin", The Journal of Biological Chemistry, vol. 275, No. 50, Dec. 2000, pp. 39427-39434.
Lindahl, et al., "Expression and Alternative Splicing of Mouse GFRα4 Suggest Roles in Endocrine Cell Development", Molecular and Cellular Neuroscience, vol. 15, 2000, pp. 522-533.
GenBank, Accession No. AL356755, Sycamore N., "Human DNA sequence from clone RP5-964F7 on chromosome 20 Contains part of a gene for a putative GDNF family receptor alpha 4 protein, the 3' part of a gene for a novel protein (disintegrin and metalloproteinase), ESTs, STSs, GSSs and CpG islands", May 23, 2000.
GenBank, Accession No. AF253318, Zhou B. et al, "Homo sapiens GFR receptor alpha 4 protein (GFRA4) mRNA, complete cds.", Oct. 26, 2000.
GenBank, Accession No. AC17113, Waterston R.H., "Homo sapiens chromosome 20 clone RP11-574H7, Working Draft Sequence, 31 unordered pieces" Dec. 14, 1999.
GenBank, Birren B. et al. "Homo sapiens chromosome 2 clone RP11-388K24 map 2, Low-pass sequence sampling", Nov. 9, 1999.
GenBank, Accession No. AP002898, Yada T. et al., "Homo sapiens genomic DNA, chromosome 20 p, clone: 13N6", Oct. 25, 2000.

* cited by examiner

*Primary Examiner*—Sumesh Kaushal
(74) *Attorney, Agent, or Firm*—Arent Fox LLP

(57) ABSTRACT

The present invention discloses purified and isolated nucleic acid sequences encoding polypeptides having a structure substantially similar to that of splicing forms of mammalian GFRα4 comprising the amino acid sequence (SEQ ID NO:1:)-(SEQ ID NO:6:). The preferred sequences comprise cDNAs having the sequence (SEQ ID NO:7:)-(SEQ ID NO:13:). The present invention is also related to purified and isolated polypeptides comprising the amino acid sequence and or substantially similar splicing forms of mammalian GFRà4. Furthermore, the invention is related to substances capable of specifically recognizing said polypeptides and including both antibodies and receptors. The active compounds of the present invention including cDNAS, polypeptides, binding substances, and antibodies. The invention is useful not only for producing cell-lines and/or transgenic non-human animal but also for diagnosing and treating neuronal disorders or endocrine tumors as well as other related diseases by enabling measurements of GFRα4-mediated signalling in endocrine cells and neurons.

12 Claims, 27 Drawing Sheets

Figure 2:
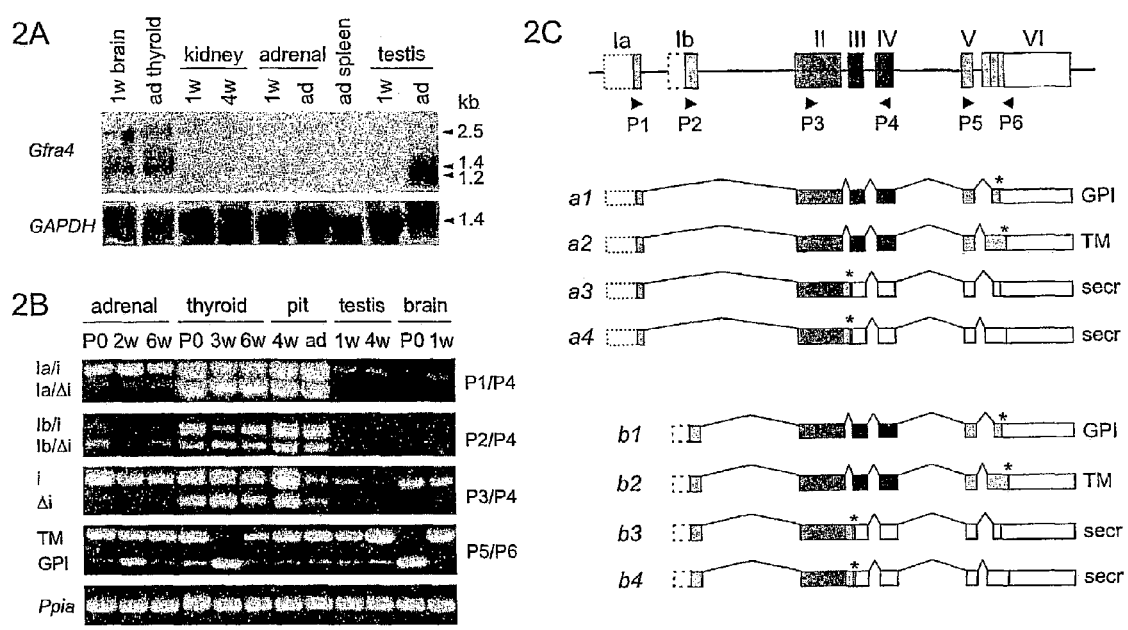

```
mGFRα1  MFLATLYFVLPLLDLLMSAEVSGGD............RLDCVKASDQCLKEQSCSTKYRTLRQCVAGK
mGFRα2  MILANAFCLFFFLDETLRSLASPSSPQGSEL.HGWRPQVDCVRANELCAAESNCSSRYRTLRQCLAGR
mGFRα3  MGLSWSPRPPLLMILLLVLSLWLPLGAGNSLATENRFVNSCTQARKKCEANPACKAAYQHLGSCTSSL
mGFRα4  MAHCMESALLLLLLLGSASFT.............................................
cGFRα4  MRGILYFCTLILLEGMAEAVSSSR..............DCLQAGESCTNDPICSSKFRTLRQCIAGN mGFRα1  ........ETNFSLTSGLEAKDECRSAMEALKQKSLYNCRCKRGMKKEKNCLRIYWSMYQSL.QGN
mGFRα2  ........DRNTML.....ANKECQAALEVLQESPLYDCRCKRGMKKELQCLQIYWSIHLGLTEGE
mGFRα3  ........SRPLPLEESAMSAD.CLEAAEQLRNSSLIDCRCHRRMKHQATCLDIYWTVHPARSLGD
mGFRα4  ..................................................................
cGFRα4  ........GAN...KLGPDAKNQCRSTVTALLSSQLYGCKCKRGMKKEKHCLSVYWSIHHTLMEGM

} D1 mGFRα1  DLLEDSPYEPVNSRLSDIFRAVPFISDVFQQVEHISKGNNCLDAAKACNLDDTCKKYRSAYITPCTTS
mGFRα2  EFYEASPYEPVTSRLSDIFRLASIFSGTGADPVVSAKSNHCLDAAKACNLNDNCKKLRSSYISICNRE
mGFRα3  YELDVSPYEDTVTSKPW.......KMNLSKLNMLKPDSDLCLKFAMICTLHDKCDRLRKAYGEACSG.
mGFRα4  ...........................DGNRCVDAAEACTADERCQQLRSEYVARCLGR
cGFRα4  NVLESSPYEPF.IRGFDYVRLASI...TAGSENEVTQVNRCLDAAKACNVDEMCQRLRTEYVSFCIRR mGFRα1  MS.NEV.....CNRRKCHKALRQFFDKVPAKHSYGMLFCSC..RDVACTERRRQTIVPVCSYEER
mGFRα2  ISPTER.....CNRRKCHKALRQFFDRVPSEYTYRMLFCSC..QDQACAERRRQTILPSCSYEDK
mGFRα3  .........IRCQRHLCLAQLRSFFEKAAESHAQGLLLCPCAPEDAGCGERRRNTIAPSCALPS.
mGFRα4  AAPGGRPGPGGCVRSRCRRALRRFFARGPPALTHALLFCGC..EGSACAERRRQTFAPACAFSGP
cGFRα4  LARADT.....CNRSKCHKALRKFFDRVPPEYTHELLFCPC..EDTACAERRRQTIVPACSYESK

} D2 mGFRα1  ..................ERPNCLNLQDSCKTNYICRSRLADFFTNCQPESRSVSN
mGFRα2  ..................EKPNCLDLRSLCRTDHLCRSLADFHANCRASYRTITS
mGFRα3  ..................VTPNCLDLRSFCRADPLCRSRLMDFQTHCHPMD.ILGT
mGFRα4  ..................GLVPPSCLEPLERCERSRICRPRLLAFQASCAPAPGSRDR
cGFRα4  ..................EKPNCLAPLDSCRENYVCRSRYAEFQFNCQPSLQTASG mGFRα1  CLKENYADCLLAYSGLIGTVMTPNYIDS..SSLSVAPWCDCSNSGNDLEDCLKFLNFFKDNTCLKN
mGFRα2  CPADNYQACLGSYAGMIGFDMTPNYVDSNPTGIVVSPWCNCRGSGNMEEECEKFLKDFTENPCLRN
mGFRα3  CATEQ.SRCLRAYLGLIGTAMTPNFISKVNTTVALS..CTCRGSGNLQDECEQLERSFSQNPCLVE
mGFRα4  CPEEGGPRCLRVYAGLIGTVVTPNYLDN..VSARVAPWCGCAASGNRREECEAFRKLFTRNPCLDG
cGFRα4  CRRDSYAACLLAYTGIIGSPITPNYIDNSTSS..IAPWCTCNASGNRQEECESFLHLFTDNVCLQN

} D3 mGFRα1  AIQAFGNGSDVTMWQPAPPVQTTTAMTTTAFRIKNKPLGP..AGSENEIPTHVLPPCANLQAQKLK
mGFRα2  AIQAFGNGTDVNM.SPKGP....TFSATQAPRVEKTPSLPDDLSDSTSLGTSVITTCTSIQEQGLK
mGFRα3  AIAA........................................................
mGFRα4  AIQAE........................................................
cGFRα4  AIQAFGNGTYLN..AATAPSISPTTQMYKQERNANRAAATLSENIFEHL............

mGFRα1  SNVSGSTHLCLSDNDYGKDGLAGASSHITTKSMAAPPSCGLSSLPVMVFTALAALLSVSLAETS
mGFRα2  ANNSKELSMCFTELTTNISPGSKKVIKLYSGSCRAR..........LSTALTALPLLMVTLA
mGFRα3  ...........KMRFHRQLFSQDWADSTFSVVQQQNSNPALRLQPRLPILSFSILPLILLQTILW
mGFRα4  ...............DSLQPSVLQDQTAGCCFPR..VSWLYALTALALQALL
cGFRα4  ...........QPTKVAGEERLLRGSTRLSSETSSPAAPCHQAASLLQLWLPPTLAVLSHFMM
```

Fig. 1A

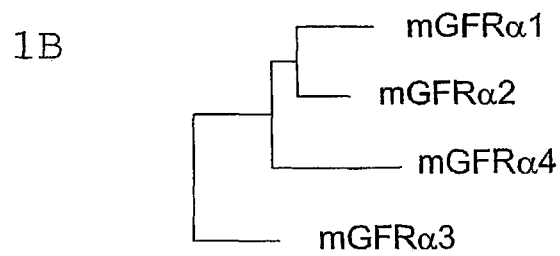
1B
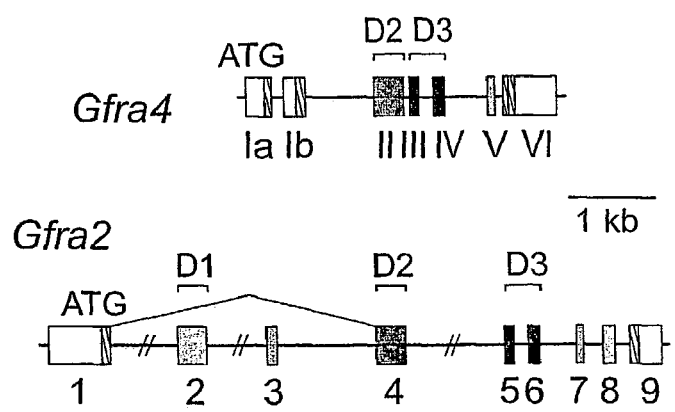
1C
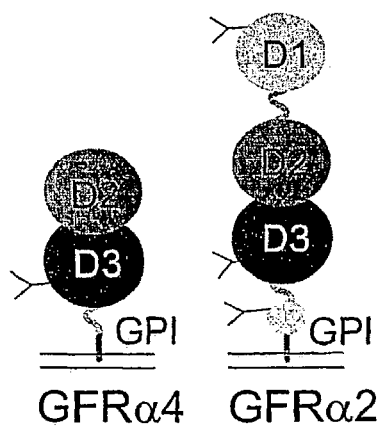
1D
Fig. 1B-D

```
exon.AGgtragt.....intron....tyyyyyyyyyyncag..exon

Ia...GGgtgaga....1284 bp....ccgcccttcaccagG...II

Ib...AGgtaaga.....851 bp....ccgcccttcaccagG...II

II...CGgtgcgt......53 bp....ccgggcgcgcgcagG..III

III..AGgtaggc......81 bp....ggggtccccgcagG...IV

IV...GGgtgagg.....541 bp....tctgcactccgcagA....V

V....GGgtaggt.....140 bp....tcctaacgcccaagG..VIa

V....GGgtaggt......73 bp....cttacccttcctagG..VIb
```

Fig. 3

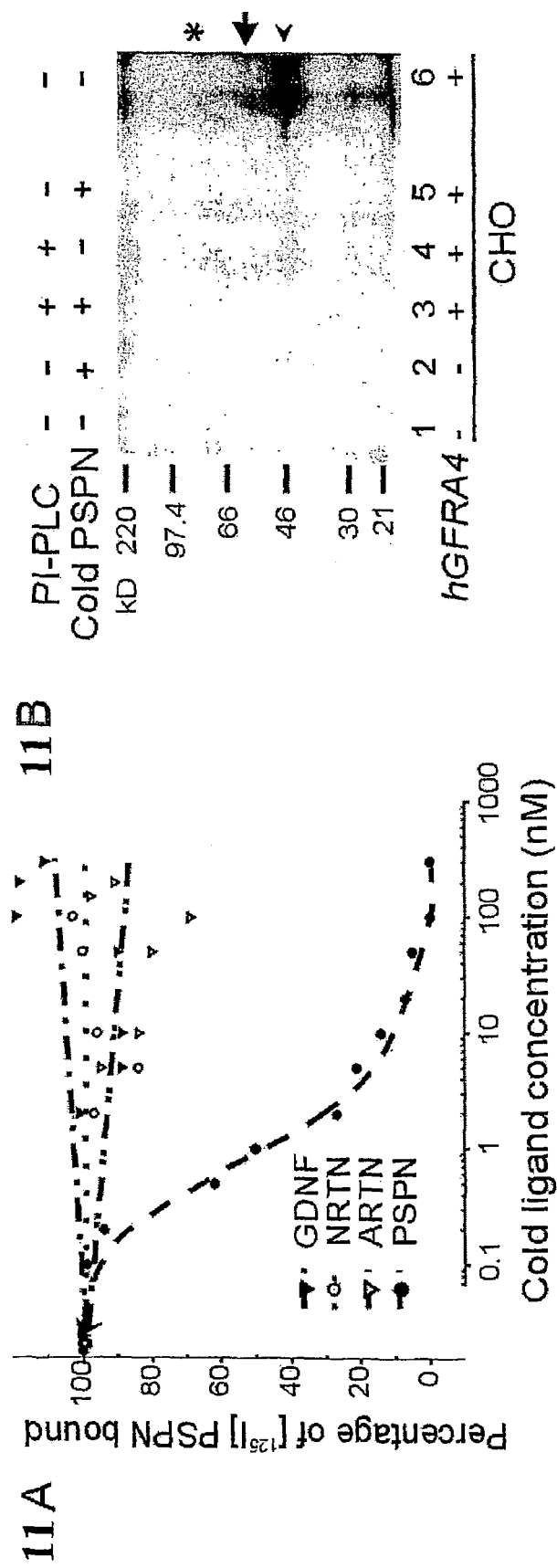
Fig. 11 A-B

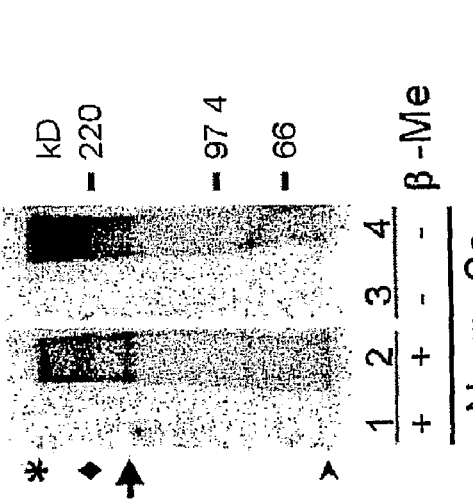
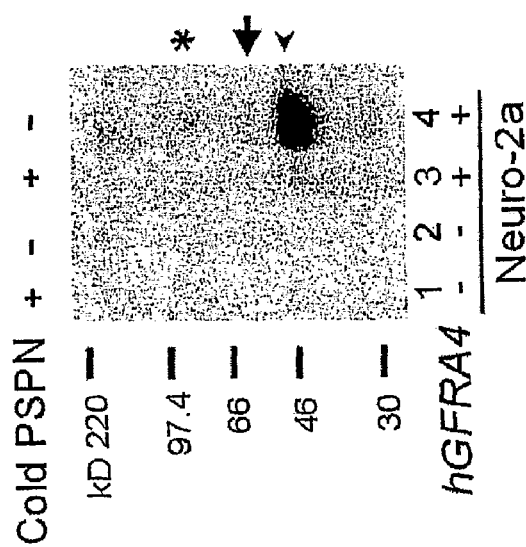
Fig. 11 C-D

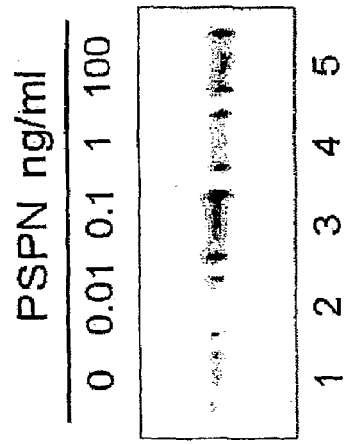
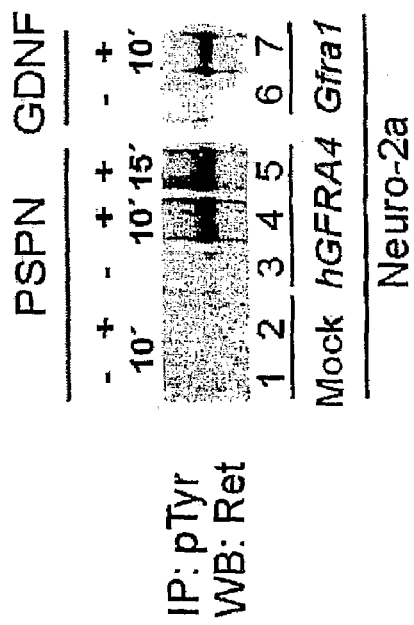
Fig. 11 E-F

15A
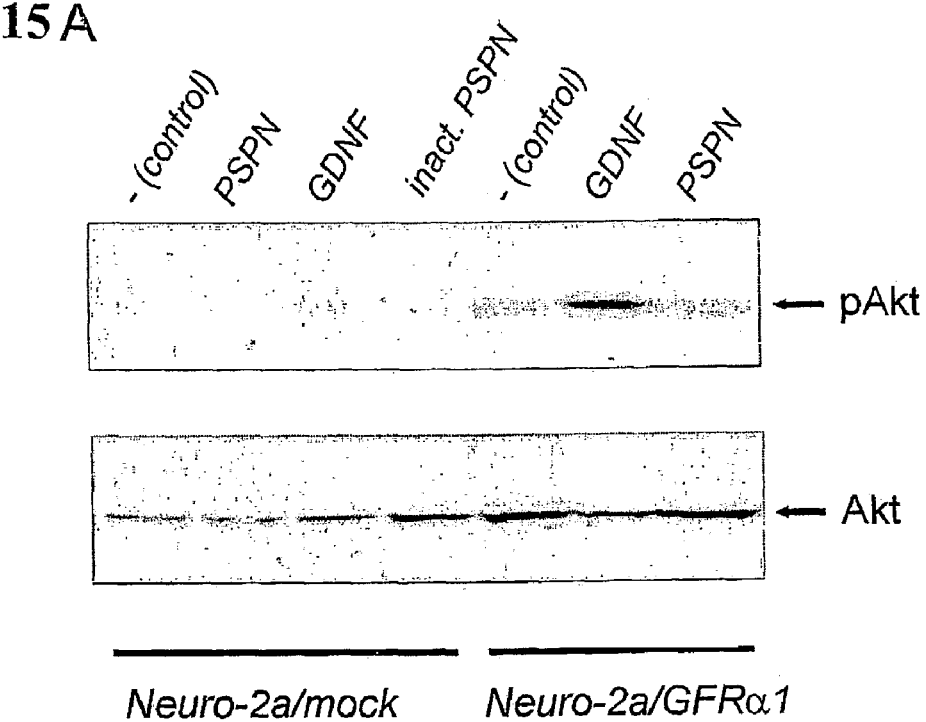
15B
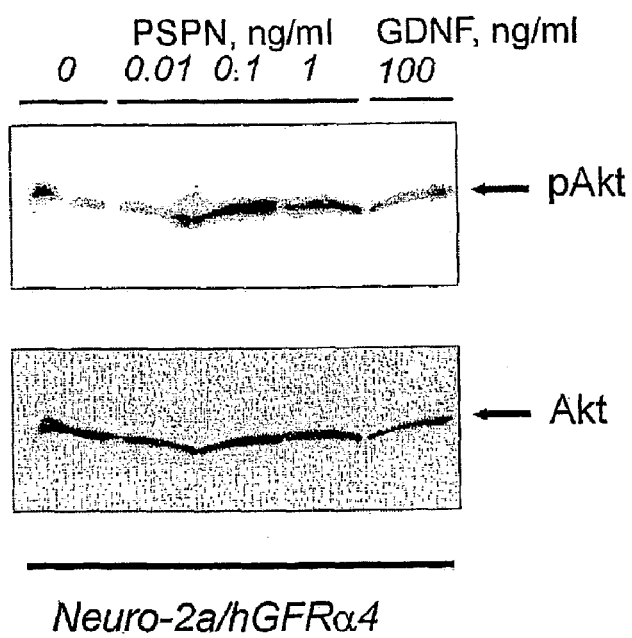
Fig. 15

17A
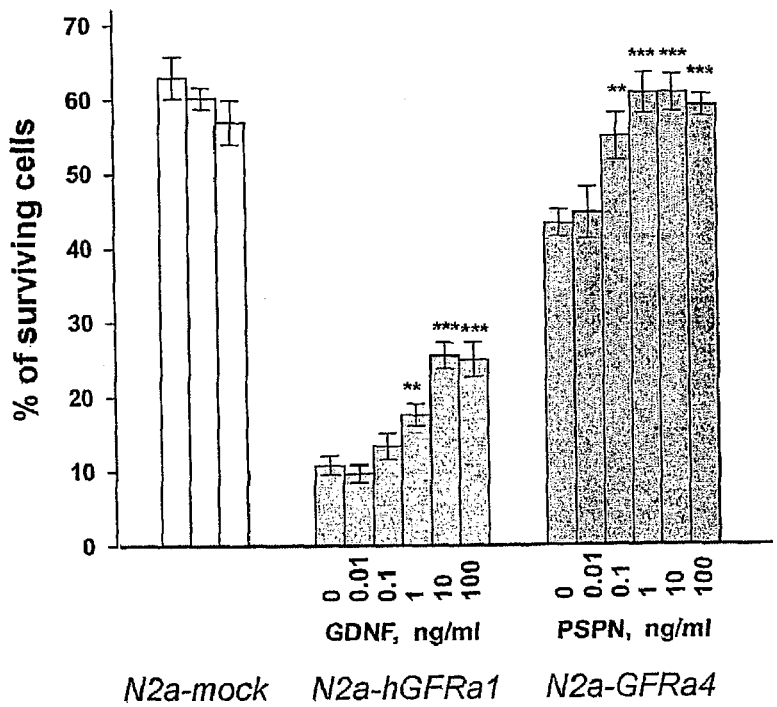
17B
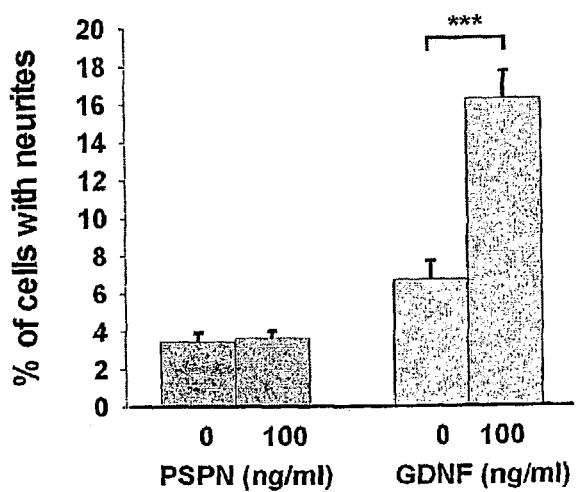
Fig. 17

Fig. 18A
Mouse Gfra4-[GPI]a1 cDNA sequence, length: 783

```
  1  atggcccact gcatggagtc tgcactgctg ctgttgttgc tgctggggtc
 51  tgcgagcttt accgacggga atcgctgcgt ggacgcggcc gaggcgtgta
101  cagcagacga gcggtgccag cagctgcgct ctgagtacgt ggcacgatgc
151  ctgggccggg cagcgcccgg gggcaggccg ggacccgggg gctgcgtgcg
201  ctcccgctgc cgccgagccc tgcgccgctt cttcgcgcgt gggcctccgg
251  cgctcacgca tgcgctgctc ttctgcggct gcgaaggctc cgcgtgcgcc
301  gagcgccggc gccagacttt cgcgcccgcc tgcgcgttct ccggcccggg
351  gttggtgccg ccctcttgcc tggagcccct ggagcgctgc gagcgcagcc
401  gcctgtgccg gccccgtctc cttgccttcc aggcctcatg cgctcccgcg
451  cccggctccc gcgaccgctg cccggaggag ggggccccgc gttgtctgcg
501  cgtctacgca ggcctcatag gcaccgtggt cacccccaac tacctggaca
551  acgtgagcgc gcgcgttgcg ccctggtgcg gctgtgcggc cagtggaaac
601  cggcgcgaag aatgcgaagc cttccgcaag ctctttacaa ggaacccctg
651  cttggatggt gccatacaag cctttgacag cttgcagcca tcagttctgc
701  aggaccagac tgctgggtgc tgtttcccgc gggtgtcctg gctgtatgca
751  ctcactgccc tggctctcca ggccctgctc tga
```

Fig. 18B
Mouse GFRα4 GPI-linked isoform a1 amino-acid sequence, length: 261

```
  1  MAHCMESALL LLLLLGSASF TDGNRCVDAA EACTADERCQ QLRSEYVARC
 51  LGRAAPGGRP GPGGCVRSRC RRALRRFFAR GPPALTHALL FCGCEGSACA
101  ERRQTFAPA CAFSGPGLVP PSCLEPLERC ERSRLCRPRL LAFQASCAPA
151  PGSRDRCPEE GGPRCLRVYA GLIGTVVTPN YLDNVSARVA PWCGCAASGN
201  RREECEAFRK LFTRNPCLDG AIQAFDSLQP SVLQDQTAGC CFPRVSWLYA
251  LTALALQALL*
```

Fig. 18

Fig. 19A
Mouse Gfra4 transcript a2 cDNA sequence, length:882

```
  1  atgcccact gcatggagtc tgcactgctg ctgttgttgc tgctggggtc
 51  tgcgagcttt accgacggga atcgctgcgt ggacgcggcc gaggcgtgta
101  cagcagacga gcggtgccag cagctgcgct ctgagtacgt ggcacgatgc
151  ctgggccggg cagcgcccgg gggcaggccg ggacccgggg gctgcgtgcg
201  ctcccgctgc cgccgagccc tgcgccgctt cttcgcgcgt gggcctccgg
251  cgctcacgca tgcgctgctc ttctgcggct gcgaaggctc cgcgtgcgcc
301  gagcgccggc gccagacttt cgcgccgcc tgcgcgttct ccggcccggg
351  gttggtgccg ccctcttgcc tggagcccct ggagcgctgc gagcgcagcc
401  gctgtgccg gccccgtctc cttgccttcc aggcctcatg cgctcccgcg
451  cccggctccc gcgaccgctg cccggaggag gggggcccgc gttgtctgcg
501  cgtctacgca ggcctcatag gcaccgtggt cacccccaac tacctggaca
551  acgtgagcgc gcgcgttgcg ccctggtgcg gctgtgcggc cagtggaaac
601  cggcgcgaag aatgcgaagc cttccgcaag ctctttacaa ggaacccctg
651  cttggatggt gccatacaag cctttgacag cttcagcca tcagttctgc
701  aggaccagac tgctgggtgc tgtttcccgc gggcaaggca cgagtggcct
751  gagaagagct ggaggcagaa acagtccttg ttttgtccta acgccaagg
801  tgtcctggct gtatgcactc actgcctgg ctctccaggc cctgctctga
851  ttaggaacat gaaccgtgga cgacacagct ga
```

Fig. 19B
Mouse GFRα4 putative TM-isoform a2 amino-acid sequence, length:294

```
  1  MAHCMESALL LLLLLGSASF TDGNRCVDAA EACTADERCQ QLRSEYVARC
 51  LGRAAPGGRP GPGGCVRSRC RRALRRFFAR GPPALTHALL FCGCEGSACA
101  ERRRQTFAPA CAFSGPGLVP PSCLEPLERC ERSRLCRPRL LAFQASCAPA
151  PGSRDCPEE GGPRCLRVYA GLIGTVVTPN YLDNVSARVA PWCGCAASGN
201  RREECEAFRK LFTRNPCLDG AIQAFDSLQP SVLQDQTAGC CFPRARHEWP
251  EKSWRQKQSL FCPNAQGVLA VCTHCPGSPG PALIRNMNRG RHS*
```

Fig. 19

Fig. 20A
Mouse Gfra4 transcript a3/a4 cDNA sequence, length:573

```
  1  ATGGCCCACT GCATGGAGTC TGCACTGCTG CTGTTGTTGC TGCTGGGGTC
 51  TGCGAGCTTT ACCGACGGGA ATCGCTGCGT GGACGCGGCC GAGGCGTGTA
101  CAGCAGACGA GCGGTGCCAG CAGCTGCGCT CTGAGTACGT GGCACGATGC
151  CTGGGCCGGG CAGCGCCCGG GGGCAGGCCG GGACCCGGGG GCTGCGTGCG
201  CTCCCGCTGC CGCCGAGCCC TGCGCCGCTT CTTCGCGCGT GGGCCTCCGG
251  CGCTCACGCA TGCGCTGCTC TTCTGCGGCT GCGAAGGCTC CGCGTGCGCC
301  GAGCGCCGGC GCCAGACTTT CGCGCCCGCC TGCGCGTTCT CCGGCCCGGG
351  GTTGGTGCCG CCCTCTTGCC TGGAGCCCCT GGAGCGCTGC GAGCGCAGCC
401  GCCTGTGCCG gtgcgtgcgt gcggggcggg ctgggccgct cacccgcgtc
451  cgggcgcgcg cagGCCCCGT CTCCTTGCCT TCCAGGCCTC ATGCGCTCCC
501  GCGCCCGGCT CCCGCGACCG CTGCCCGGAG GAGGGGGGCC CGCGTTGTCT
551  GCGCGTCTAC GCAGGCCTCA TAG
```

Fig. 20B
Mouse GFRα4 soluble isoform a3/4 amino-acid sequence, length: 191

```
  1  MAHCMESALL LLLLLGSASF TDGNRCVDAA EACTADERCQ QLRSEYVARC
 51  LGRAAPGGRP GPGGCVRSRC RRALRRFFAR GPPALTHALL FCGCEGSACA
101  ERRRQTFAPA CAFSGPGLVP PSCLEPLERC ERSRLCRCVR AGRAGPLTRV
151  RARAGPVSLP SRPHALPRPA PATAARRRGA RVVCASTQAS*
```

Fig. 20

Fig. 21A
Human GFRA4a cDNA sequence (GPI-linked splice form a), length: 810

```
  1 ATGGTCCGCT GCCTGGGGCC TGCGCTGCTG CTGCTGCTGT TACTGGGGTC
 51 GGCGAGCTCG GTCGGAGGGA ACCGATGTGT GGACGCGGCC GAAGCCTGCA
101 CGGCGGACGC GCGGTGCCAG CGTTTGCGCT CCGAGTATGT GGCGCAGTGC
151 CTGGGCCGGG CTGCGCAGGG GGGCTGTCCC CGCGCCCGCT GCCGCCGGGC
201 CCTGCGCCGC TTCTTCGCCC GCGGGCCGCC CGCGCTCACC CACGCACTGC
251 TCTTCTGCCC GTGCGCGGGC CCCGCGTGCG CCGAGCGTCG GCGCCAGACC
301 TTCGTGCCCT CCTGCGCCTT TTCGGGGCCC GGCCCCGCGC CGCCCTCCTG
351 CCTTGAGCCC TTAAACTTCT GCGAGCGCAG CCGGGTCTGC AGGCCTCGCC
401 TCCTGGCCTT TCAGGTCTCG TGCACCCCAG CGCCCAGCGC CCCCGACGGC
451 TGCCTGCTGG ACCAGGGCGC CCGCTGCCTG CGCGCCTACG CGGGCCTCGT
501 GGGCACCGCC GTCACCCCTA ACTACGTGGA CAACGTGAGC GCGCGCGTGG
551 CGCCCTGGTG CGACTGCGGA GCCAGCGGGA ACCGGCGTGA GGACTGCGAA
601 GCCTTCCGGG GGCTCTTTAC CAGGAACCGC TGCTTGGATG GTGCCATTCA
651 GGCCTTTGCC AGCGGGTGGC CCCAGTCCT GCTGGACCAG CTGAACCCCC
701 AGGGAGACCC GGAGCACAGC CTCCTGCAGG TGTCCTCCAC AGGCAGGGCC
751 CTGGAGAGAC GCTCCCTGCT CTCCATACTT CCTGTCCTGG CTCTCCCGGC
801 CCTGCTCTGA
```

Fig. 21B
Human GFRα4a amino-acid sequence (GPI-linked isoform a), length: 269

```
  1 MVRCLGPALL LLLLLGSASS VGGNRCVDAA EACTADARCQ RLRSEYVAQC
 51 LGRAAQGGCP RARCRRALRR FFARGPPALT HALLFCPCAG PACAERRRQT
101 FVPSCAFSGP GPAPPSCLEP LNFCERSRVC RPRLLAFQVS CTPAPSAPDG
151 CLLDQGARCL RAYAGLVGTA VTPNYVDNVS ARVAPWCDCG ASGNRREDCE
201 AFRGLFTRNR CLDGAIQAFA SGWPPVLLDQ LNPQGDPEHS LLQVSSTGRA
251 LERRSLLSIL PVLALPALL*
```

Fig. 21

Fig. 22A
Human GFRA4b splice form cDNA sequence, length: 900

ATGGTCCGCTGCCTGGGGCCTGCGCTGCTGCTGCTGCTGTTACTGGGGTCGGCGAGCTCGGTCGGAGGG
AACCGATGTGTGGACGCGGCCGAAGCCTGCACGGCGGACGCGCGGTGCCAGCGTTTGCGCTCCGAGTAT
GTGGCGCAGTGCCTGGGCCGGGCTGCGCAGGGGGGCTGTCCCCGCGCCCGCTGCCGCCGGGCCCTGCGC
CGCTTCTTCGCCCGCGGGCCGCCCGCGCTCACCCACGCACTGCTCTTCTGCCCGTGCGCGGGCCCCGCG
TGCGCCGAGCGTCGGCGCCAGACCTTCGTGCCCTCCTGCGCCTTTTCGGGGCCCGGCCCCGCGCCGCCC
TCCTGCCTTGAGCCCTTAAACTTCTGCGAGCGCAGCCGGGTCTGCAGGTGCGCGCGGGCGGCGGCGGGG
CCGTGGCGAGGGTGGGGACGGGGCCTCTCTCCGGCTCACCGCCCTCCCCGCCGCGCAGGCCTCGCCTCCT
GGCCTTTCAGGTCTCGTGCACCCCAGCGCCCAGCGCCCCGACGGCTGCCTGCTGGACCAGGGCGCCCG
CTGCCTGCGCGCCTACGCGGGCCTCGTGGgtccccgcaggcaccgccgtcacccctaactacgtggac
aacgtgagcgcgcgcgtggcgccctggtgcgactgcggagccagcgggaaccggcgtgaggactgcgaa
gccttccgggggctcttaccaggaaccgctgcttggATGGTGCCATTCAGGCCTTTGCCAGCGGGTGG
CCCCCAGTCCTGCTGGACCAGCTGAACCCCCAGGGAGACCCGGAGCACAGCCTCCTGCAGGTGTCCTCC
ACAGGCAGGGCCCTGGAGAGACGCTCCCTGCTCTCCATACTTCCTGTCCTGGCTCTCCCGGCCCTGCTC
TGA Fig. 22B
Human GFRα4b (putative GPI-anchored isoform b) amino-acid sequence,
length:299

The non-homologous part (from GFRα4a) is indicated in grey, this
corresponds to the translated intron 2, exon 3 (in other frame), and
four amino acids (GVPA) from intron 3.

MVRCLGPALLLLLLGSASSVGGNRCVDAAEACTADARCQRLRSEYVAQCLGRAAQGGCPRARCRRALR
RFFARGPPALTHALLFCPCAGPACAERRRQTFVPSCAFSGPGPAPPSCLEPLNFCERSRVCRCARAAAG
PWRGWGRGLSPAHRPPAAQASPPGLSGLVHPSAQRPRRLPAGPGRPLPARLRGPRGVPAGTAVTPNYVD
NVSARVAPWCDCGASGNRREDCEAFRGLFTRNRCLDGATQAFASGWPPVLLDQLNPQGDPEHSLLQVSS
TGRALERRSLLSILPVLALPALL*

Fig. 22

Fig. 23A
Human *GFRA4c* (putative soluble form) cDNA sequence, length: 549

```
  1 ATGGTCCGCT GCCTGGGGCC TGCGCTGCTG CTGCTGCTGT TACTGGGGTC
 51 GGCGAGCTCG GTCGGAGGGA ACCGATGTGT GGACGCGGCC GAAGCCTGCA
101 CGGCGGACGC GCGGTGCCAG CGTTTGCGCT CCGAGTATGT GGCGCAGTGC
151 CTGGGCCGGG CTGCGCAGGG GGGCTGTCCC CGCGCCCGCT GCCGCCGGGC
201 CCTGCGCCGC TTCTTCGCCC GCGGGCCGCC CGCGCTCACC CACGCACTGC
251 TCTTCTGCCC GTGCGCGGGC CCCGCGTGCG CCGAGCGTCG GCGCCAGACC
301 TTCGTGCCCT CCTGCGCCTT TTCGGGGCCC GGCCCCGCGC CGCCCTCCTG
351 CCTTGAGCCC TTAAACTTCT GCGAGCGCAG CCGGGTCTGC AGGCCTCGCC
401 TCCTGGCCTT TCAGGTCTCG TGCACCCCAG CGCCCAGCGC CCCCGACGGC
451 TGCCTGCTGG ACCAGGGCGC CCGCTGCCTG CGCGCCTACG CGGGCCTCGT
501 GGGGTCCCCG CAGGCACCGC CGTCACCCCT AACTACGTGG ACAACGTGA
```

Fig. 23B
Human GFRα4c (putative soluble isoform c) amino-acid sequence,
length: 182

```
  1 MVRCLGPALL LLLLLGSASS VGGNRCVDAA EACTADARCQ RLRSEYVAQC
 51 LGRAAQGGCP RARCRRALRR FFARGPPALT HALLFCPCAG PACAERRRQT
101 FVPSCAFSGP GPAPPSCLEP LNFCERSRVC RPRLLAFQVS CTPAPSAPDG
151 CLLDQGARCL RAYAGLVGSP QAPPSPLTTW TT*
```

Fig. 23

Human *GFRA4* locus genomic sequence

..CTATCAGACTAGGGCTCTGCCAGCCATCCTTCTCTGTTGAAGGTCCAGCATGGTCCGCTGCCTGG
GGCCTGCGCTGCTGCTGCTGCTGTTACTGGgt..longintron..agGGTCGGCGAGCTCG
GTCGGAGGGAACCGATGTGTGGACGCGGCCGAAGCCTGCACGGCGGACGCGCGGTGCCAGCG
TTTGCGCTCCGAGTATGTGGCGCAGTGCCTGGGCCGGGCTGCGCAGGGGGGCTGTCCCCGCG
CCCGCTGCCGCCGGGCCCTGCGCCGCTTCTTCGCCCGCGGGCCGCCCGCGCTCACCCACGCA
CTGCTCTTCTGCCCGTGCGCGGGCCCCGCGTGCGCCGAGCGTCGGCGCCAGACCTTCGTGCC
CTCCTGCGCCTTTTCGGGGCCCGGCCCCGCGCCGCCCTCCTGCCTTGAGCCCTTAAACTTCT
GCGAGCGCAGCCGGGTCTGCAGgtgcgcgcgggcggcggcggggccgtggcgagggtgggga
cggggcctctctccggctcaccgccctccgccgcgcagGCCTCGCCTCCTGGCCTTTCAGG
TCTCGTGCACCCCAGCGCCCAGCGCCCCCGACGGCTGCCTGCTGGACCAGGGCGCCCGCTGC
CTGCGCGCCTACGCGGGCCTCGTGGtacgcgcggccgggatccgggcgagggcgggggttc
tccaggggatatctccgcccgggtgggccgatgacttcgccctcagggtccccgcagGCACC
GCCGTCACCCCTAACTACGTGGACAACGTGAGCGCGCGCGTGGCGCCCTGGTGCGACTGCGG
AGCCAGCGGGAACCGGCGTGAGGACTGCGAAGCCTTCCGGGGGCTCTTTACCAGGAACCGCT
GCTTGGgtgaggggcccggggggagtggaggggagtggggcggcgcttactgccccctc
ccaagccgcctggctgggagccattttagaggggagaatggaagactgtacagttgagtcac
tctgtcacagctgtgcttattgttttgttattcctcaccacacaccttctgtccaaggagcc
agtctttgcagcaggggtctctcactttgtccctgtgctgagccctgtgctagggtttcc
cagctaagtccaccctggacccctcctccatagATGGTGCCATTCAGGCCTTTGCCAGCGG
GTGGCCCCCAGTCCTGCTGGACCAGCTGAACCCCCAGGGAGACCCGGAGCACAGCCTCCTGC
AGgtaggtgcagggaggggagggtgagctggcacctcccccactgtcaccttcacaccttc
cgtccctggtgggcctgggtggaggcatgaagggcctggggtgggggtgcaggcagagggca
gagacaggcttttgcctcaagtctgcacttggctcccaccccaagGTGTCCTCCACAGGCA
GGGCCCTGGAGAGACGCTCCCTGCTCTCCATACTTCCTGTCCTGGCTCTCCCGGCCCTGCTC
TGATTAGGACAGCGACCTCGGATAGCACAGCCAGCTACTCCACCCTGCCTGCCTGGGCCGCC
TCTGTGGCCTACTGGCCCCTTGAGAAGGGACTGGCTTACCCCCCAAGCCGGCCCTGGTGCTT
TCACTCCGCTGCCCTTTGTAGGTTTGGACACCCTGTGTGCCGTCCCCTGGGGCAAGGGATGT
AGGCTGGGGCCTGACTGTAAAGCCCCGTCTCCCTGTCAGGAGGCATCTTGGTTGTAAGTCC
CTTTATTCACAGACCTTGAGACCACTGGGGTCTCCCACAAGGTGGGGTCAGGAGAGGTCACT
TTTGTAGCTGAGACCTCTCTGGAGACCCAGATCCCCTAGAGCAGGTCAGAGACATCCAGAAT
CCCAGAATTCTAGGAAATTGTATCAGCCTCCCAAGCATATAACCCCCTAAGGAATCCATCGG
ACAAGACCCGTCTAACACTGCATCCTCCCAACTGGGGCATTACCCACCATTGTAGCCACCTG
TGCACCATGACATGCTGGGCAGAGTCTTTCCTGTTCCCCATATGCTGCCTGTGGAGGAAAAC
CTGCAAGGGGCA..

Fig. 24

SEQUENCE LISTING

<160> NUMBER OF SEQ ID NOS: 62

<210> SEQ ID NO 1
<211> LENGTH: 260
<212> TYPE: PRT
<213> ORGANISM: Mus musculus
<220> FEATURE:
<223> OTHER INFORMATION: GPI-linked isoform a1

<400> SEQUENCE: 1

```
Met Ala His Cys Met Glu Ser Ala Leu Leu Leu Leu Leu Leu Gly
  1               5                  10                  15

Ser Ala Ser Phe Thr Asp Gly Asn Arg Cys Val Asp Ala Ala Glu Ala
                 20                  25                  30

Cys Thr Ala Asp Glu Arg Cys Gln Gln Leu Arg Ser Glu Tyr Val Ala
             35                  40                  45

Arg Cys Leu Gly Arg Ala Ala Pro Gly Gly Arg Pro Gly Pro Gly Gly
         50                  55                  60

Cys Val Arg Ser Arg Cys Arg Arg Ala Leu Arg Arg Phe Phe Ala Arg
 65                  70                  75                  80

Gly Pro Pro Ala Leu Thr His Ala Leu Leu Phe Cys Gly Cys Glu Gly
                 85                  90                  95

Ser Ala Cys Ala Glu Arg Arg Arg Gln Thr Phe Ala Pro Ala Cys Ala
                100                 105                 110

Phe Ser Gly Pro Gly Leu Val Pro Pro Ser Cys Leu Glu Pro Leu Glu
            115                 120                 125

Arg Cys Glu Arg Ser Arg Leu Cys Arg Pro Arg Leu Leu Ala Phe Gln
        130                 135                 140

Ala Ser Cys Ala Pro Ala Pro Gly Ser Arg Asp Arg Cys Pro Glu Glu
145                 150                 155                 160

Gly Gly Pro Arg Cys Leu Arg Val Tyr Ala Gly Leu Ile Gly Thr Val
                165                 170                 175

Val Thr Pro Asn Tyr Leu Asp Asn Val Ser Ala Arg Val Ala Pro Trp
            180                 185                 190

Cys Gly Cys Ala Ala Ser Gly Asn Arg Arg Glu Glu Cys Glu Ala Phe
        195                 200                 205

Arg Lys Leu Phe Thr Arg Asn Pro Cys Leu Asp Gly Ala Ile Gln Ala
    210                 215                 220

Phe Asp Ser Leu Gln Pro Ser Val Leu Gln Asp Gln Thr Ala Gly Cys
225                 230                 235                 240

Cys Phe Pro Arg Val Ser Trp Leu Tyr Ala Leu Thr Ala Leu Ala Leu
                245                 250                 255

Gln Ala Leu Leu
            260
```

<210> SEQ ID NO 2
<211> LENGTH: 293
<212> TYPE: PRT
<213> ORGANISM: Mus musculus
<220> FEATURE:
<223> OTHER INFORMATION: Putative transmembrane anchored isoform a2

<400> SEQUENCE: 2

```
Met Ala His Cys Met Glu Ser Ala Leu Leu Leu Leu Leu Leu Gly
  1               5                  10                  15

Ser Ala Ser Phe Thr Asp Gly Asn Arg Cys Val Asp Ala Ala Glu Ala
```

```
                20                  25                  30
Cys Thr Ala Asp Glu Arg Cys Gln Gln Leu Arg Ser Glu Tyr Val Ala
         35                  40                  45
Arg Cys Leu Gly Arg Ala Ala Pro Gly Gly Arg Pro Gly Pro Gly Gly
     50                  55                  60
Cys Val Arg Ser Arg Cys Arg Arg Ala Leu Arg Arg Phe Phe Ala Arg
 65                  70                  75                  80
Gly Pro Pro Ala Leu Thr His Ala Leu Leu Phe Cys Gly Cys Glu Gly
                 85                  90                  95
Ser Ala Cys Ala Glu Arg Arg Gln Thr Phe Ala Pro Ala Cys Ala
             100                 105                 110
Phe Ser Gly Pro Gly Leu Val Pro Pro Ser Cys Leu Glu Pro Leu Glu
             115                 120                 125
Arg Cys Glu Arg Ser Arg Leu Cys Arg Pro Arg Leu Leu Ala Phe Gln
         130                 135                 140
Ala Ser Cys Ala Pro Ala Pro Gly Ser Arg Asp Arg Cys Pro Glu Glu
145                 150                 155                 160
Gly Gly Pro Arg Cys Leu Arg Val Tyr Ala Gly Leu Ile Gly Thr Val
                 165                 170                 175
Val Thr Pro Asn Tyr Leu Asp Asn Val Ser Ala Arg Val Ala Pro Trp
             180                 185                 190
Cys Gly Cys Ala Ala Ser Gly Asn Arg Arg Glu Glu Cys Glu Ala Phe
         195                 200                 205
Arg Lys Leu Phe Thr Arg Asn Pro Cys Leu Asp Gly Ala Ile Gln Ala
     210                 215                 220
Phe Asp Ser Leu Gln Pro Ser Val Leu Gln Asp Gln Thr Ala Gly Cys
225                 230                 235                 240
Cys Phe Pro Arg Ala Arg His Glu Trp Pro Glu Lys Ser Trp Arg Gln
                 245                 250                 255
Lys Gln Ser Leu Phe Cys Pro Asn Ala Gln Gly Val Leu Ala Val Cys
             260                 265                 270
Thr His Cys Pro Gly Ser Pro Gly Pro Ala Leu Ile Arg Asn Met Asn
         275                 280                 285
Arg Gly Arg His Ser
    290

<210> SEQ ID NO 3
<211> LENGTH: 190
<212> TYPE: PRT
<213> ORGANISM: Mus musculus
<220> FEATURE:
<223> OTHER INFORMATION: Putative secreted isoform a3/4

<400> SEQUENCE: 3

Met Ala His Cys Met Glu Ser Ala Leu Leu Leu Leu Leu Leu Leu Gly
 1               5                  10                  15
Ser Ala Ser Phe Thr Asp Gly Asn Arg Cys Val Asp Ala Ala Glu Ala
                 20                  25                  30
Cys Thr Ala Asp Glu Arg Cys Gln Gln Leu Arg Ser Glu Tyr Val Ala
         35                  40                  45
Arg Cys Leu Gly Arg Ala Ala Pro Gly Gly Arg Pro Gly Pro Gly Gly
     50                  55                  60
Cys Val Arg Ser Arg Cys Arg Arg Ala Leu Arg Arg Phe Phe Ala Arg
 65                  70                  75                  80
Gly Pro Pro Ala Leu Thr His Ala Leu Leu Phe Cys Gly Cys Glu Gly
```

```
                85                  90                  95
Ser Ala Cys Ala Glu Arg Arg Gln Thr Phe Ala Pro Ala Cys Ala
            100                 105                 110
Phe Ser Gly Pro Gly Leu Val Pro Pro Ser Cys Leu Glu Pro Leu Glu
            115                 120                 125
Arg Cys Glu Arg Ser Arg Leu Cys Arg Val Cys Arg Ala Gly Arg Ala
            130                 135                 140
Gly Pro Leu Thr Arg Val Arg Ala Arg Ala Gly Pro Val Ser Leu Pro
145                 150                 155                 160
Ser Arg Pro His Ala Leu Pro Arg Pro Ala Pro Thr Ala Ala Arg
            165                 170                 175
Arg Arg Gly Ala Arg Val Val Cys Ala Ser Thr Gln Ala Ser
            180                 185                 190

<210> SEQ ID NO 4
<211> LENGTH: 269
<212> TYPE: PRT
<213> ORGANISM: Homo sapiens
<220> FEATURE:
<223> OTHER INFORMATION: GPI-anchored isoform a

<400> SEQUENCE: 4

Met Val Arg Cys Leu Gly Pro Ala Leu Leu Leu Leu Leu Leu Gly
 1               5                  10                  15
Ser Ala Ser Ser Val Gly Gly Asn Arg Cys Val Asp Ala Ala Glu Ala
                20                  25                  30
Cys Thr Ala Asp Ala Arg Cys Gln Arg Leu Arg Ser Glu Tyr Val Ala
            35                  40                  45
Gln Cys Leu Gly Arg Ala Ala Gln Gly Gly Cys Pro Arg Ala Arg Cys
        50                  55                  60
Arg Arg Ala Leu Arg Arg Phe Phe Ala Arg Gly Pro Pro Ala Leu Thr
65                  70                  75                  80
His Ala Leu Leu Phe Cys Pro Cys Ala Gly Pro Ala Cys Ala Glu Arg
                85                  90                  95
Arg Arg Gln Thr Phe Val Pro Ser Cys Ala Phe Ser Gly Pro Gly Pro
            100                 105                 110
Ala Pro Pro Ser Cys Leu Glu Pro Leu Asn Phe Cys Glu Arg Ser Arg
            115                 120                 125
Val Cys Arg Pro Arg Leu Leu Ala Phe Gln Val Ser Cys Thr Pro Ala
            130                 135                 140
Pro Ser Ala Pro Asp Gly Cys Leu Leu Asp Gln Gly Ala Arg Cys Leu
145                 150                 155                 160
Arg Ala Tyr Ala Gly Leu Val Gly Thr Ala Val Thr Pro Asn Tyr Val
                165                 170                 175
Asp Asn Val Ser Ala Arg Val Ala Pro Trp Cys Asp Cys Gly Ala Ser
                180                 185                 190
Gly Asn Arg Arg Glu Asp Cys Glu Ala Phe Arg Gly Leu Phe Thr Arg
                195                 200                 205
Asn Arg Cys Leu Asp Gly Ala Ile Gln Ala Phe Ala Ser Gly Trp Pro
            210                 215                 220
Pro Val Leu Leu Asp Gln Leu Asn Pro Gln Gly Asp Pro Glu His Ser
225                 230                 235                 240
Leu Leu Gln Val Ser Ser Thr Gly Arg Ala Leu Glu Arg Arg Ser Leu
                245                 250                 255
Leu Ser Ile Leu Pro Val Leu Ala Leu Pro Ala Leu Leu
```

<210> SEQ ID NO 5
<211> LENGTH: 299
<212> TYPE: PRT
<213> ORGANISM: Homo sapiens
<220> FEATURE:
<223> OTHER INFORMATION: Putative GPI-anchored isoform b

<400> SEQUENCE: 5

Met Val Arg Cys Leu Gly Pro Ala Leu Leu Leu Leu Leu Leu Leu Gly
1               5                   10                  15

Ser Ala Ser Ser Val Gly Gly Asn Arg Cys Val Asp Ala Ala Glu Ala
            20                  25                  30

Cys Thr Ala Asp Ala Arg Cys Gln Arg Leu Arg Ser Glu Tyr Val Ala
        35                  40                  45

Gln Cys Leu Gly Arg Ala Ala Gln Gly Gly Cys Pro Arg Ala Arg Cys
    50                  55                  60

Arg Arg Ala Leu Arg Arg Phe Phe Ala Arg Gly Pro Pro Ala Leu Thr
65                  70                  75                  80

His Ala Leu Leu Phe Cys Pro Cys Ala Gly Pro Ala Cys Ala Glu Arg
                85                  90                  95

Arg Arg Gln Thr Phe Val Pro Ser Cys Ala Phe Ser Gly Pro Gly Pro
            100                 105                 110

Ala Pro Pro Ser Cys Leu Glu Pro Leu Asn Phe Cys Glu Arg Ser Arg
        115                 120                 125

Val Cys Arg Cys Ala Arg Ala Ala Gly Pro Trp Arg Gly Trp Gly
    130                 135                 140

Arg Gly Leu Ser Pro Ala His Arg Pro Ala Ala Gln Ala Ser Pro
145                 150                 155                 160

Pro Gly Leu Ser Gly Leu Val His Pro Ser Ala Gln Arg Pro Arg Arg
                165                 170                 175

Leu Pro Ala Gly Pro Gly Arg Pro Leu Pro Ala Arg Leu Arg Gly Pro
            180                 185                 190

Arg Gly Val Pro Ala Gly Thr Ala Val Thr Pro Asn Tyr Val Asp Asn
        195                 200                 205

Val Ser Ala Arg Val Ala Pro Trp Cys Asp Cys Gly Ala Ser Gly Asn
    210                 215                 220

Arg Arg Glu Asp Cys Glu Ala Phe Arg Gly Leu Phe Thr Arg Asn Arg
225                 230                 235                 240

Cys Leu Asp Gly Ala Ile Gln Ala Phe Ala Ser Gly Trp Pro Pro Val
                245                 250                 255

Leu Leu Asp Gln Leu Asn Pro Gln Gly Asp Pro Glu His Ser Leu Leu
            260                 265                 270

Gln Val Ser Ser Thr Gly Arg Ala Leu Glu Arg Arg Ser Leu Leu Ser
        275                 280                 285

Ile Leu Pro Val Leu Ala Leu Pro Ala Leu Leu
    290                 295

<210> SEQ ID NO 6
<211> LENGTH: 182
<212> TYPE: PRT
<213> ORGANISM: Homo sapiens
<220> FEATURE:
<223> OTHER INFORMATION: Putative secreted isoform c

<400> SEQUENCE: 6

```
Met Val Arg Cys Leu Gly Pro Ala Leu Leu Leu Leu Leu Leu Gly
 1               5                  10                  15

Ser Ala Ser Ser Val Gly Gly Asn Arg Cys Val Asp Ala Glu Ala
            20                  25                  30

Cys Thr Ala Asp Ala Arg Cys Gln Arg Leu Arg Ser Glu Tyr Val Ala
        35                  40                  45

Gln Cys Leu Gly Arg Ala Ala Gln Gly Gly Cys Pro Arg Ala Arg Cys
    50                  55                  60

Arg Arg Ala Leu Arg Arg Phe Phe Ala Arg Gly Pro Pro Ala Leu Thr
65                  70                  75                  80

His Ala Leu Leu Phe Cys Pro Cys Ala Gly Pro Ala Cys Ala Glu Arg
                85                  90                  95

Arg Arg Gln Thr Phe Val Pro Ser Cys Ala Phe Ser Gly Pro Gly Pro
                100                 105                 110

Ala Pro Pro Ser Cys Leu Glu Pro Leu Asn Phe Cys Glu Arg Ser Arg
            115                 120                 125

Val Cys Arg Pro Arg Leu Leu Ala Phe Gln Val Ser Cys Thr Pro Ala
    130                 135                 140

Pro Ser Ala Pro Asp Gly Cys Leu Leu Asp Gln Gly Ala Arg Cys Leu
145                 150                 155                 160

Arg Ala Tyr Ala Gly Leu Val Gly Ser Pro Gln Ala Pro Pro Ser Pro
                165                 170                 175

Leu Thr Thr Trp Thr Thr
            180
```

<210> SEQ ID NO 7
<211> LENGTH: 783
<212> TYPE: DNA
<213> ORGANISM: Mus musculus
<220> FEATURE:
<223> OTHER INFORMATION: Splice form (a1) for GPI linked protein

<400> SEQUENCE: 7

| | |
|---|---|
| atggcccact gcatggagtc tgcactgctg ctgttgttgc tgctggggtc tgcgagcttt | 60 |
| accgacggga atcgctgcgt ggacgcggcc gaggcgtgta cagcagacga gcggtgccag | 120 |
| cagctgcgct ctgagtacgt ggcacgatgc ctgggccggg cagcgcccgg ggcaggccg | 180 |
| ggacccgggg gctgcgtgcg ctcccgctgc cgccgagccc tgcgccgctt cttcgcgcgt | 240 |
| gggcctccgg cgctcacgca tgcgctgctc ttctgcggct gcgaaggctc gcgtgcgcc | 300 |
| gagcgccggc gccagacttt cgcgcccgcc tgcgcgttct ccggcccggg gttggtgccg | 360 |
| ccctcttgcc tggagcccct ggagcgctgc gagcgcagcc gcctgtgccg gccccgtctc | 420 |
| cttgccttcc aggcctcatg cgctcccgcg cccggctccc gcgaccgctg cccggaggag | 480 |
| gggggcccgc gttgtctgcg cgtctacgca ggcctcatag caccgtggt cacccccaac | 540 |
| tacctggaca cgtgagcgc gcgcgttgcg ccctggtgcg ctgtgccggc agtggaaac | 600 |
| cggcgcgaag aatgcgaagc cttccgcaag ctctttacaa ggaaccctg cttggatggt | 660 |
| gccatacaag cctttgacag cttgcagcca tcagttctgc aggaccagac tgctgggtgc | 720 |
| tgtttcccgc gggtgtcctg gctgtatgca ctcactgccc tggctctcca ggccctgctc | 780 |
| tga | 783 |

<210> SEQ ID NO 8
<211> LENGTH: 882
<212> TYPE: DNA
<213> ORGANISM: Mus musculus -continued

```
<220> FEATURE:
<223> OTHER INFORMATION: Splice form (a2) (for putative transmembrane
      anchored protein)

<400> SEQUENCE: 8
atggcccact gcatggagtc tgcactgctg ctgttgttgc tgctggggtc tgcgagcttt    60
accgacggga atcgctgcgt ggacgcggcc gaggcgtgta cagcagacga gcggtgccag   120
cagctgcgct ctgagtacgt ggcacgatgc ctgggccggg cagcgccggg ggcaggccg    180 ggacccgggg gctgcgtgcg ctcccgctgc cgccgagccc tgcgccgctt cttcgcgcgt   240
gggcctccgg cgctcacgca tgcgctgctc ttctgcggct gcgaaggctc cgcgtgcgcc   300
gagcgccggc gccagacttt cgcgcccgcc tgcgcgttct ccggcccggg gttggtgccg   360
ccctcttgcc tggagcccct ggagcgctgc gagcgcagcc gcctgtgccg gccccgtctc   420
cttgccttcc aggcctcatg cgctcccgcg cccggctccc gcgaccgctg cccggaggag   480
ggggggcccg gttgtctgcg cgtctacgca ggcctcatag gcaccgtggt cacccccaac   540
tacctggaca acgtgagcgc gcgcgttgcg ccctggtgcg gctgtgcggc cagtggaaac   600
cggcgcgaag aatgcgaagc cttccgcaag ctctttacaa ggaacccctg cttggatggt   660
gccatacaag ccttttgacag cttgcagcca tcagttctgc aggaccagac tgctgggtgc   720
tgtttcccgc gggcaaggca cgagtggcct gagaagagct ggaggcagaa acagtccttg   780
ttttgtccta acgcccaagg tgtcctggct gtatgcactc actgccctgg ctctccaggc   840
cctgctctga ttaggaacat gaaccgtgga cgacacagct ga                      882

<210> SEQ ID NO 9
<211> LENGTH: 573
<212> TYPE: DNA
<213> ORGANISM: Mus musculus
<220> FEATURE:
<223> OTHER INFORMATION: Splice form (a3/a4) (for secreted protein)

<400> SEQUENCE: 9
atggcccact gcatggagtc tgcactgctg ctgttgttgc tgctggggtc tgcgagcttt    60
accgacggga atcgctgcgt ggacgcggcc gaggcgtgta cagcagacga gcggtgccag   120
cagctgcgct ctgagtacgt ggcacgatgc ctgggccggg cagcgccggg ggcaggccg    180 ggacccgggg gctgcgtgcg ctcccgctgc cgccgagccc tgcgccgctt cttcgcgcgt   240
gggcctccgg ctcgcacgca tgcgctgctc ttctgcggct gcgaaggctc cgcgtgcgcc   300
gagcgccggc gccagacttt cgcgcccgcc tgcgcgttct ccggcccggg gttggtgccg   360
ccctcttgcc tggagcccct ggagcgctgc gagcgcagcc gcctgtgccg gtgcgtgcgt   420
gcggggcggg ctgggccgct caccgcgtc cgggcgcgcg caggccccgt ctccttgcct   480
tccaggcctc atgcgctccc gcgcccggct cccgcgaccg ctgcccggag gagggggggcc   540 cgcgttgtct gcgcgtctac gcaggcctca tag                                573

<210> SEQ ID NO 10
<211> LENGTH: 810
<212> TYPE: DNA
<213> ORGANISM: Homo sapiens
<220> FEATURE:
<223> OTHER INFORMATION: Coding sequence of the splice form a for
      GPI-anchored protein

<400> SEQUENCE: 10
atggtccgct gcctggggcc tgcgctgctg ctgctgctgt tactggggtc ggcgagctcg    60
```

-continued

```
gtcggaggga accgatgtgt ggacgcggcc gaagcctgca cggcggacgc gcggtgccag    120
cgtttgcgct ccgagtatgt ggcgcagtgc ctgggccggg ctgcgcaggg gggctgtccc    180
cgcgcccgct gccgccgggc cctgcgccgc ttcttcgccc gcgggccgcc cgcgctcacc    240
cacgcactgc tcttctgccc gtgcgcgggc cccgcgtgcg ccgagcgtcg gcgccagacc    300
ttcgtgccct cctgcgcctt tcggggccc ggccccgcgc cgccctcctg ccttgagccc    360
ttaaacttct gcgagcgcag ccgggtctgc aggcctcgcc tcctggcctt tcaggtctcg    420
tgcaccccag cgcccagcgc ccccgacggc tgcctgctgg accagggcgc ccgctgcctg    480
cgcgcctacg cgggcctcgt gggcaccgcc gtcaccccta actacgtgga caacgtgagc    540
gcgcgcgtgg cgccctggtg cgactgcgga ccagcggga accggcgtga ggactgcgaa    600
gccttccggg ggctctttac caggaaccgc tgcttggatg gtgccattca ggcctttgcc    660
agcgggtggc ccccagtcct gctggaccag ctgaaccccc agggagaccc ggagcacagc    720
ctcctgcagg tgtcctccac aggcagggcc ctggagagac gctccctgct ctccatactt    780
cctgtcctgg ctctcccggc cctgctctga                                    810
```

<210> SEQ ID NO 11
<211> LENGTH: 900
<212> TYPE: DNA
<213> ORGANISM: Homo sapiens
<220> FEATURE:
<223> OTHER INFORMATION: Splice form b

<400> SEQUENCE: 11

```
atggtccgct gcctggggcc tgcgctgctg ctgctgctgt tactggggtc ggcgagctcg    60
gtcggaggga accgatgtgt ggacgcggcc gaagcctgca cggcggacgc gcggtgccag   120
cgtttgcgct ccgagtatgt ggcgcagtgc ctgggccggg ctgcgcaggg gggctgtccc   180
cgcgcccgct gccgccgggc cctgcgccgc ttcttcgccc gcgggccgcc cgcgctcacc   240
cacgcactgc tcttctgccc gtgcgcgggc cccgcgtgcg ccgagcgtcg gcgccagacc   300
ttcgtgccct cctgcgcctt tcggggccc ggccccgcgc cgccctcctg ccttgagccc   360
ttaaacttct gcgagcgcag ccgggtctgc aggtgcgcgc gggcggcggc ggggccgtgg   420
cgagggtggg gacggggcct ctctccggct caccgccctc ccgccgcgca ggcctcgcct   480
cctggccttt caggtctcgt gcaccccagc gcccagcgcc cccgacggct gcctgctgga   540
ccagggcgcc cgctgcctgc gcgcctacg gggcctcgtg ggtcccgc aggcaccgcc   600 gtcacccta actacgtgga caacgtgagc gcgcgcgtgg cgccctggtg cgactgcgga   660
gccagcggga accggcgtga ggactgcgaa gccttccggg ggctctttac caggaaccgc   720
tgcttggatg gtgccattca ggcctttgcc agcgggtggc ccccagtcct gctggaccag   780
ctgaaccccc agggagaccc ggagcacagc ctcctgcagg tgtcctccac aggcagggcc   840
ctggagagac gctccctgct ctccatactt cctgtcctgg ctctcccggc cctgctctga   900
```

<210> SEQ ID NO 12
<211> LENGTH: 549
<212> TYPE: DNA
<213> ORGANISM: Homo sapiens
<220> FEATURE:
<223> OTHER INFORMATION: Splice form c encoding putative secreted
      protein

<400> SEQUENCE: 12

```
atggtccgct gcctggggcc tgcgctgctg ctgctgctgt tactggggtc ggcgagctcg    60
```

-continued

```
gtcggaggga accgatgtgt ggacgcggcc gaagcctgca cggcggacgc gcggtgccag    120
cgtttgcgct ccgagtatgt ggcgcagtgc ctgggcgggg ctgcgcaggg gggctgtccc    180
cgcgcccgct gccgcgggc cctgcgccgc ttcttcgccc gcgggccgcc cgcgctcacc    240
cacgcactgc tcttctgccc gtgcgcgggc cccgcgtgcg ccgagcgtcg gcgccagacc    300
ttcgtgccct cctgcgcctt tcggggccc ggccccgcgc cgccctcctg ccttgagccc    360
ttaaacttct gcgagcgcag ccgggtctgc aggcctcgcc tcctggcctt tcaggtctcg    420
tgcaccccag cgcccagcgc ccccgacggc tgcctgctgg accagggcgc ccgctgcctg    480
cgcgcctacg cgggcctcgt ggggtccccg caggcaccgc cgtcaccct aactacgtgg    540 acaacgtga                                                           549
```

<210> SEQ ID NO 13  
<211> LENGTH: 2047  
<212> TYPE: DNA  
<213> ORGANISM: Homo sapiens  
<220> FEATURE:  
<221> NAME/KEY: intron  
<222> LOCATION: (97)  
<223> OTHER INFORMATION: A genomic sequence containing an approximately 500 bp long intron between positions 97 and 98 (not shown)

<400> SEQUENCE: 13

```
ctatcagact agggctctgc cagccatcct tctctgttga aggtccagca tggtccgctg     60
cctggggcct gcgctgctgc tgctgctgtt actgggtagg gtcggcgagc tcggtcggag    120
ggaaccgatg tgtggacgcg ccgaagcct gcacggcgga cgcgcggtgc cagcgtttgc    180
gctccgagta tgtggcgcag tgcctgggcc gggctgcgca gggggggctgt ccccgcgccc    240 gctgccgccg ggccctgcgc cgcttcttcg cccgcgggcc gccgcgctc acccacgcac    300 tgctcttctg cccgtgcgcg ggccccgcgt gcgccgagcg tcggcgccag accttcgtgc    360
cctcctgcgc cttttcgggg cccggccccg cgccgccctc ctgccttgag cccttaaact    420
tctgcgagcg cagccgggtc tgcaggtgcg cgcgggcggc ggcggggccg tggcgagggt    480
ggggacgggg cctctctccg gctcaccgcc ctcccgccgc gcaggcctcg cctcctggcc    540
tttcaggtct cgtgcacccc agcgcccagc gccccgacg ctgcctgct ggaccagggc    600 gcccgctgcc tgcgcgccta cgcgggcctc gtgggtacgc gcggccggga tccgggcgag    660
ggcgggggtt ctccagggga tatctccgcc cgggtgggcc gatgacttcg ccctcagggt    720
ccccgcaggc accgccgtca cccctaacta cgtggacaac gtgagcgcgc gcgtggcgcc    780
ctggtgcgac tgcggagcca gcgggaaccg gcgtgaggac tgcgaagcct tccggggct    840 cttaccagg aaccgctgct ggtgaggg cccgggggg gagtggaggg ggagtggggg    900
cggcgcttac tgcccctcc caagccgcct ggctgggagc cattttagag gggagaatgg    960
aagactgtac agttgagtca ctctgtcaca gctgtgctta ttgtttgtt attcctcacc   1020 acacaccttc tgtccaagga gccagtcttt gcagcagggg gtctctcact ttgtcccctg   1080
tgctgagccc tgtgctaggg tttcccagct aagtccaccc tggacccctc cctccataga   1140
tggtgccatt caggcctttg ccagcgggtg gccccagtc ctgctggacc agctgaaccc   1200
ccagggagac ccggagcaca gcctcctgca ggtaggtgca gggaggggag ggtgagctgg   1260 cacctcccc actgtcacct tcacacccct ccgtccctgg tgggcctggg tggaggcatg   1320
aagggcctgg ggtggggtg caggcagagg gcagagacag gcttttgcct caagtctgca   1380
cttggctccc accccaagg tgtcctccac aggcagggcc ctggagagac gctccctgct   1440
```

-continued

```
ctccatactt cctgtcctgg ctctcccggc cctgctctga ttaggacagc gacctcggat    1500
agcacagcca gctactccac cctgcctgcc tgggccgcct ctgtggccta ctggcccctt    1560
gagaagggac tggcttaccc cccaagccgg ccctggtgct ttcactccgc tgcccttgt    1620 aggtttggac accctgtgtg ccgtcccctg gggcaaggga tgtaggctgg ggcctgactg    1680
taaagccccc gtctccctgt caggaggcat cttggttgta agtccctta ttcacagacc    1740 ttgagaccac tggggtctcc cacaaggtgg ggtcaggaga ggtcactttt gtagctgaga    1800
cctctctgga gacccagatc ccctagagca ggtcagagac atccagaatc ccagaattct    1860
aggaaattgt atcagcctcc caagcatata acccctaag gaatccatcg gacaagaccc     1920
gtctaacact gcatcctccc aactgggca ttacccacca ttgtagccac ctgtgcacca     1980
tgacatgctg ggcagagtct ttcctgttcc ccatatgctg cctgtggagg aaacctgca    2040 aggggca                                                              2047
```

```
<210> SEQ ID NO 14
<211> LENGTH: 24
<212> TYPE: PRT
<213> ORGANISM: Mus musculus
<220> FEATURE:
<223> OTHER INFORMATION: Putative signaling sequence from alternative
      exon 1B

<400> SEQUENCE: 14

Met Leu Arg Arg Ala His Leu Met Asp Glu Arg Pro Gly Gln Ala Ile
 1               5                  10                  15

Phe Leu Gly Leu Gly Ser Gln Arg
            20

<210> SEQ ID NO 15
<211> LENGTH: 53
<212> TYPE: PRT
<213> ORGANISM: Mus musculus
<220> FEATURE:
<223> OTHER INFORMATION: Unique region of the secreted isoform (a3/4)

<400> SEQUENCE: 15

Cys Val Arg Ala Gly Arg Ala Gly Pro Leu Thr Arg Val Arg Ala Arg
 1               5                  10                  15

Ala Gly Pro Val Ser Leu Pro Ser Arg Pro His Ala Leu Pro Arg Pro
            20                  25                  30

Ala Pro Ala Thr Ala Ala Arg Arg Gly Ala Arg Val Val Cys Ala
        35                  40                  45

Ser Thr Gln Ala Ser
    50

<210> SEQ ID NO 16
<211> LENGTH: 49
<212> TYPE: PRT
<213> ORGANISM: Mus musculus
<220> FEATURE:
<223> OTHER INFORMATION: Putative transmembrane anchor sequence

<400> SEQUENCE: 16

Ala Arg His Glu Trp Pro Glu Lys Ser Trp Arg Gln Lys Gln Ser Leu
 1               5                  10                  15

Phe Cys Pro Asn Ala Gln Gly Val Leu Ala Val Cys Thr His Cys Pro
            20                  25                  30

Gly Ser Pro Gly Pro Ala Leu Ile Arg Asn Met Asn Arg Gly Arg His
```

```
              35                  40                  45
Ser

<210> SEQ ID NO 17
<211> LENGTH: 16
<212> TYPE: PRT
<213> ORGANISM: Mus musculus
<220> FEATURE:
<223> OTHER INFORMATION: GPI anchor

<400> SEQUENCE: 17

Val Ser Trp Leu Tyr Ala Leu Thr Ala Leu Ala Leu Gln Ala Leu Leu
 1               5                  10                  15

<210> SEQ ID NO 18
<211> LENGTH: 23
<212> TYPE: DNA
<213> ORGANISM: Mus musculus
<220> FEATURE:
<223> OTHER INFORMATION: 5' RACE primer 1

<400> SEQUENCE: 18
ttcagctcag tgagcagtca tcg                                              23

<210> SEQ ID NO 19
<211> LENGTH: 20
<212> TYPE: DNA
<213> ORGANISM: Mus musculus
<220> FEATURE:
<223> OTHER INFORMATION: 5' RACE primer 2

<400> SEQUENCE: 19
caggttgtcc aggtagttgg                                                  20

<210> SEQ ID NO 20
<211> LENGTH: 20
<212> TYPE: DNA
<213> ORGANISM: Mus musculus
<220> FEATURE:
<223> OTHER INFORMATION: 5' RACE primer 3

<400> SEQUENCE: 20
catcgtgcca cgtactcaga                                                  20

<210> SEQ ID NO 21
<211> LENGTH: 24
<212> TYPE: DNA
<213> ORGANISM: Mus musculus
<220> FEATURE:
<223> OTHER INFORMATION: 3' RACE primer 1

<400> SEQUENCE: 21
tacaagcctt tgacagcttg cagc                                             24

<210> SEQ ID NO 22
<211> LENGTH: 23
<212> TYPE: DNA
<213> ORGANISM: Mus musculus
<220> FEATURE:
<223> OTHER INFORMATION: 3' RACE primer 2

<400> SEQUENCE: 22
agagctggag gcagaaacag tcc                                              23

<210> SEQ ID NO 23
```

```
<211> LENGTH: 25
<212> TYPE: DNA
<213> ORGANISM: Mus musculus
<220> FEATURE:
<223> OTHER INFORMATION: Exon 1a sense primer 1

<400> SEQUENCE: 23
ccaccatggc ccactgcatg gagtc                                              25

<210> SEQ ID NO 24
<211> LENGTH: 20
<212> TYPE: DNA
<213> ORGANISM: Mus musculus
<220> FEATURE:
<223> OTHER INFORMATION: Exon 1b sense primer 2

<400> SEQUENCE: 24
ccaccatgtt gagaagagca                                                    20

<210> SEQ ID NO 25
<211> LENGTH: 20
<212> TYPE: DNA
<213> ORGANISM: Mus musculus
<220> FEATURE:
<223> OTHER INFORMATION: Exon 2 sense primer 3

<400> SEQUENCE: 25
gtgtacagca gacgagcggt                                                    20

<210> SEQ ID NO 26
<211> LENGTH: 22
<212> TYPE: DNA
<213> ORGANISM: Mus musculus
<220> FEATURE:
<223> OTHER INFORMATION: Exon 5 sense primer 5

<400> SEQUENCE: 26
atacaagcct ttgacagctt gc                                                 22

<210> SEQ ID NO 27
<211> LENGTH: 21
<212> TYPE: DNA
<213> ORGANISM: Mus musculus
<220> FEATURE:
<223> OTHER INFORMATION: Exon 4 antisense primer 4

<400> SEQUENCE: 27
gttccttgta aagagcttgc g                                                  21

<210> SEQ ID NO 28
<211> LENGTH: 21
<212> TYPE: DNA
<213> ORGANISM: Mus musculus
<220> FEATURE:
<223> OTHER INFORMATION: Exon 6 antisense primer 6

<400> SEQUENCE: 28
tggacaagat gcctactgac g                                                  21

<210> SEQ ID NO 29
<211> LENGTH: 49
<212> TYPE: DNA
<213> ORGANISM: Homo sapiens
<220> FEATURE:
<223> OTHER INFORMATION: Exon1 (5' UTR)

<400> SEQUENCE: 29
```

```
ctatcagact agggctctgc cagccatcct tctctgttga aggtccagc           49
```

<210> SEQ ID NO 30
<211> LENGTH: 46
<212> TYPE: DNA
<213> ORGANISM: Homo sapiens
<220> FEATURE:
<223> OTHER INFORMATION: Exon1 (translated region)

<400> SEQUENCE: 30

```
atggtccgct gcctggggcc tgcgctgctg ctgctgctgt tactgg              46
```

<210> SEQ ID NO 31
<211> LENGTH: 346
<212> TYPE: DNA
<213> ORGANISM: Homo sapiens
<220> FEATURE:
<223> OTHER INFORMATION: Exon2

<400> SEQUENCE: 31

```
ggtcggcgag ctcggtcgga gggaaccgat gtgtggacgc ggccgaagcc tgcacggcgg    60
acgcgcggtg ccagcgtttg cgctccgagt atgtggcgca gtgcctgggc cgggctgcgc   120 agggggctg tccccgcgcc cgctgccgcc gggccctgcg ccgcttcttc gcccgcgggc    180
cgcccgcgct cacccacgca ctgctcttct gcccgtgcgc gggccccgcg tgcgccgagc   240
gtcggcgcca gaccttcgtg ccctcctgcg ccttttcggg gccggcccc gcgccgccct    300 cctgccttga gccttaaaac ttctgcgagc gcagccgggt ctgcag                   346
```

<210> SEQ ID NO 32
<211> LENGTH: 79
<212> TYPE: DNA
<213> ORGANISM: Homo sapiens
<220> FEATURE:
<223> OTHER INFORMATION: Intron 2

<400> SEQUENCE: 32

```
gtgcgcgcgg gcggcggcag ggccgtggcg agggtgggga cggggccttt ctccgggtca    60
ccgccctccc gccgcgcag                                                  79
```

<210> SEQ ID NO 33
<211> LENGTH: 110
<212> TYPE: DNA
<213> ORGANISM: Homo sapiens
<220> FEATURE:
<223> OTHER INFORMATION: Exon3

<400> SEQUENCE: 33

```
gcctcgcctc ctggcctttc aggtctcgtg cacccagcg cccagcgccc ccgacggctg     60
cctgctggac cagggcgccc gctgcctgcg cgcctacgcg ggcctcgtgg               110
```

<210> SEQ ID NO 34
<211> LENGTH: 94
<212> TYPE: DNA
<213> ORGANISM: Homo sapiens
<220> FEATURE:
<223> OTHER INFORMATION: Intron3 (83 bp for alternative spliced putative
      secreted form)

<400> SEQUENCE: 34

```
gtacgctcgg ccgggatccg gccgagggcg ggggttctcc aggggatata tccgcccggg    60
tgggccgatg acttcgccct cagggtcccc gcag                                 94
```

<210> SEQ ID NO 35
<211> LENGTH: 135
<212> TYPE: DNA
<213> ORGANISM: Homo sapiens
<220> FEATURE:
<223> OTHER INFORMATION: Exon4

<400> SEQUENCE: 35

```
gcaccgccgt caccccctaac tacgtggaca acgtgagcgc gcgcgtggcg ccctggtgcg    60
actgcggagc cagcgggaac cggcgtgagg actgcgaagc cttccggggg ctctttacca   120
ggaaccgctg cttgg                                                    135
```

<210> SEQ ID NO 36
<211> LENGTH: 276
<212> TYPE: DNA
<213> ORGANISM: Homo sapiens
<220> FEATURE:
<223> OTHER INFORMATION: Intron4

<400> SEQUENCE: 36

```
gtgaggggcc cggggggggag tggagggggga gtggggggcgg cgcttactgc ccccctcccaa    60
gccgcctggc tgggagccat tttagagggg agaatggaag actgtacagt tgagtcactc   120
tgtcacagct gtgcttattg ttttgttatt cctcaccaca caccttctgt ccaaggagcc   180
agtctttgca gcaggggggtc tctcactttg tcccctgtgc tgagccctgt gctagggttt   240
cccagctaag tccacccctgg accccctccct ccatag                           276
```

<210> SEQ ID NO 37
<211> LENGTH: 92
<212> TYPE: DNA
<213> ORGANISM: Homo sapiens
<220> FEATURE:
<223> OTHER INFORMATION: Exon5

<400> SEQUENCE: 37

```
atggtgccat tcaggccttt gccagcgggt ggcccccagt cctgctggac cagctgaacc    60
cccagggaga cccggagcac agcctcctgc ag                                  92
```

<210> SEQ ID NO 38
<211> LENGTH: 168
<212> TYPE: DNA
<213> ORGANISM: Homo sapiens
<220> FEATURE:
<223> OTHER INFORMATION: Intron5

<400> SEQUENCE: 38

```
gtaggtgcag ggaggggagg gtgagctggc acctcccccca ctgtcacctt cacacccttc    60
cgtccctggt gggcctgggt ggaggcatga agggcctggg gtgggggtgc aggcagaggg   120
cagagacagg ctttttgcctc aagtctgcac ttggctccca cccccaag                168
```

<210> SEQ ID NO 39
<211> LENGTH: 81
<212> TYPE: DNA
<213> ORGANISM: Homo sapiens
<220> FEATURE:
<223> OTHER INFORMATION: Exon6 (translated region)

<400> SEQUENCE: 39

```
gtgtcctcca caggcagggc cctggagaga cgctccctgc tctccatact tcctgtcctg    60
```

-continued

```
gctctcccgg ccctgctctg a                                               81
```

<210> SEQ ID NO 40
<211> LENGTH: 557
<212> TYPE: DNA
<213> ORGANISM: Homo sapiens
<220> FEATURE:
<223> OTHER INFORMATION: Exon6 (3' UTR)

<400> SEQUENCE: 40

```
ttaggacagc gacctcggat agcacagcca gctactccac cctgcctgcc tgggccgcct     60
ctgtggccta ctggcccctt gagaagggac tggcttaccc cccaagccgg ccctggtgct    120
ttcactccgc tgcccttttgt aggtttggac accctgtgtg ccgtcccctg gggcaaggga   180
tgtaggctgg ggcctgactg taaagccccc gtctccctgt caggaggcat cttggttgta    240
agtcccttta ttcacagacc ttgagaccac tggggtctcc cacaaggtgg ggtcaggaga    300
ggtcactttt gtagctgaga cctctctgga gacccagatc ccctagagca ggtcagagac    360
atccagaatc ccagaattct aggaaattgt atcagcctcc caagcatata acccccctaag   420
gaatccatcg gacaagaccc gtctaacact gcatcctccc aactgggggca ttacccacca   480
ttgtagccac ctgtgcacca tgacatgctg ggcagagtct ttcctgttcc ccatatgctg    540
cctgtggagg aaaacct                                                   557
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41

```
cacgttgtcc aggtagttgg                                                 20
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 42

```
gcactgcgcc acatactcgg a                                               21
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 43

```
gctccgagta tgtggcgcag t                                               21
```

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 44

```
gctcacccac gcactgctct tctg                                            24
```

```
<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
cctaactacg tggacaacgt gagc                                          24

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 46
atggtgccat tcaggccttt gccag                                         25

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 47
gcaggtgtcc tccacaggca g                                             21

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 48
gaagtatgga gagcagggag cgtc                                          24

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 49
ccaccatggt ccgctgcctg g                                             21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 50
gaggtcgctg tcctaatcag ag                                            22

<210> SEQ ID NO 51
<211> LENGTH: 468
<212> TYPE: PRT
<213> ORGANISM: Mus musculus
```

<400> SEQUENCE: 51

```
Met Phe Leu Ala Thr Leu Tyr Phe Val Leu Pro Leu Leu Asp Leu Leu
1               5                   10                  15
Met Ser Ala Glu Val Ser Gly Gly Asp Arg Leu Asp Cys Val Lys Ala
            20                  25                  30
Ser Asp Gln Cys Leu Lys Glu Gln Ser Cys Ser Thr Lys Tyr Arg Thr
        35                  40                  45
Leu Arg Gln Cys Val Ala Gly Lys Glu Thr Asn Phe Ser Leu Thr Ser
    50                  55                  60
Gly Leu Glu Ala Lys Asp Glu Cys Arg Ser Ala Met Glu Ala Leu Lys
65                  70                  75                  80
Gln Lys Ser Leu Tyr Asn Cys Arg Cys Lys Arg Gly Met Lys Lys Glu
                85                  90                  95
Lys Asn Cys Leu Arg Ile Tyr Trp Ser Met Tyr Gln Ser Leu Gln Gly
            100                 105                 110
Asn Asp Leu Leu Glu Asp Ser Pro Tyr Glu Pro Val Asn Ser Arg Leu
        115                 120                 125
Ser Asp Ile Phe Arg Ala Val Pro Phe Ile Ser Asp Val Phe Gln Gln
    130                 135                 140
Val Glu His Ile Ser Lys Gly Asn Asn Cys Leu Asp Ala Ala Lys Ala
145                 150                 155                 160
Cys Asn Leu Asp Asp Thr Cys Lys Lys Tyr Arg Ser Ala Tyr Ile Thr
                165                 170                 175
Pro Cys Thr Thr Ser Met Ser Asn Glu Val Cys Asn Arg Arg Lys Cys
            180                 185                 190
His Lys Ala Leu Arg Gln Phe Phe Asp Lys Val Pro Ala Lys His Ser
        195                 200                 205
Tyr Gly Met Leu Phe Cys Ser Cys Arg Asp Val Ala Cys Thr Glu Arg
    210                 215                 220
Arg Arg Gln Thr Ile Val Pro Val Cys Ser Tyr Glu Glu Arg Glu Arg
225                 230                 235                 240
Pro Asn Cys Leu Asn Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
            260                 265                 270
Ser Val Ser Asn Cys Leu Lys Glu Asn Tyr Ala Asp Cys Leu Leu Ala
        275                 280                 285
Tyr Ser Gly Leu Ile Gly Thr Val Met Thr Pro Asn Tyr Ile Asp Ser
    290                 295                 300
Ser Ser Leu Ser Val Ala Pro Trp Cys Asp Cys Ser Asn Ser Gly Asn
305                 310                 315                 320
Asp Leu Glu Asp Cys Leu Lys Phe Leu Asn Phe Phe Lys Asp Asn Thr
                325                 330                 335
Cys Leu Lys Asn Ala Ile Gln Ala Phe Gly Asn Gly Ser Asp Val Thr
            340                 345                 350
Met Trp Gln Pro Ala Pro Val Gln Thr Thr Thr Ala Met Thr Thr Thr
        355                 360                 365
Thr Ala Phe Arg Ile Lys Asn Lys Pro Leu Gly Pro Ala Gly Ser Glu
    370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Ser Thr His Leu Cys Leu Ser
                405                 410                 415
```

```
Asp Asn Asp Tyr Gly Lys Asp Gly Leu Ala Gly Ala Ser Ser His Ile
            420                 425                 430

Thr Thr Lys Ser Met Ala Ala Pro Pro Ser Cys Gly Leu Ser Ser Leu
            435                 440                 445

Pro Val Met Val Phe Thr Ala Leu Ala Ala Leu Leu Ser Val Ser Leu
        450                 455                 460

Ala Glu Thr Ser
465

<210> SEQ ID NO 52
<211> LENGTH: 463
<212> TYPE: PRT
<213> ORGANISM: Mus musculus

<400> SEQUENCE: 52

Met Ile Leu Ala Asn Ala Phe Cys Leu Phe Phe Leu Asp Glu Thr
  1               5                  10                  15

Leu Arg Ser Leu Ala Ser Pro Ser Ser Pro Gln Gly Ser Glu Leu His
                 20                  25                  30

Gly Trp Arg Pro Gln Val Asp Cys Val Arg Ala Asn Glu Leu Cys Ala
             35                  40                  45

Ala Glu Ser Asn Cys Ser Ser Arg Tyr Arg Thr Leu Arg Gln Cys Leu
         50                  55                  60

Ala Gly Arg Asp Arg Asn Thr Met Leu Ala Asn Lys Glu Cys Gln Ala
 65                  70                  75                  80

Ala Leu Glu Val Leu Gln Glu Ser Pro Leu Tyr Asp Cys Arg Cys Lys
                 85                  90                  95

Arg Gly Met Lys Lys Glu Leu Gln Cys Leu Gln Ile Tyr Trp Ser Ile
            100                 105                 110

His Leu Gly Leu Thr Glu Gly Glu Glu Phe Tyr Glu Ala Ser Pro Tyr
        115                 120                 125

Glu Pro Val Thr Ser Arg Leu Ser Asp Ile Phe Arg Leu Ala Ser Ile
    130                 135                 140

Phe Ser Gly Thr Gly Ala Asp Pro Val Val Ser Ala Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Ser
                245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
        275                 280                 285

Asn Tyr Gln Ala Cys Leu Gly Ser Tyr Ala Gly Met Ile Gly Phe Asp
    290                 295                 300

Met Thr Pro Asn Tyr Val Asp Ser Asn Pro Thr Gly Ile Val Val Ser
```

```
                 305                 310                 315                 320

Pro Trp Cys Asn Cys Arg Gly Ser Gly Asn Met Glu Glu Cys Glu
                325                 330                 335

Lys Phe Leu Lys Asp Phe Thr Glu Asn Pro Cys Leu Arg Asn Ala Ile
                340                 345                 350

Gln Ala Phe Gly Asn Gly Thr Asp Val Asn Met Ser Pro Lys Gly Pro
                355                 360                 365

Thr Phe Ser Ala Thr Gln Ala Pro Arg Val Glu Lys Thr Pro Ser Leu
            370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
                420                 425                 430

Ser Lys Lys Val Ile Lys Leu Tyr Ser Gly Ser Cys Arg Ala Arg Leu
                435                 440                 445

Ser Thr Ala Leu Thr Ala Leu Pro Leu Leu Met Val Thr Leu Ala
            450                 455                 460

<210> SEQ ID NO 53
<211> LENGTH: 397
<212> TYPE: PRT
<213> ORGANISM: Mus musculus

<400> SEQUENCE: 53

Met Gly Leu Ser Trp Ser Pro Arg Pro Leu Leu Met Ile Leu Leu
  1               5                  10                  15

Leu Val Leu Ser Leu Trp Leu Pro Leu Gly Ala Gly Asn Ser Leu Ala
                 20                  25                  30

Thr Glu Asn Arg Phe Val Asn Ser Cys Thr Gln Ala Arg Lys Lys Cys
             35                  40                  45

Glu Ala Asn Pro Ala Cys Lys Ala Ala Tyr Gln His Leu Gly Ser Cys
         50                  55                  60

Thr Ser Ser Leu Ser Arg Pro Leu Pro Leu Glu Glu Ser Ala Met Ser
 65                  70                  75                  80

Ala Asp Cys Leu Glu Ala Ala Glu Gln Leu Arg Asn Ser Ser Leu Ile
                 85                  90                  95

Asp Cys Arg Cys His Arg Arg Met Lys His Gln Ala Thr Cys Leu Asp
            100                 105                 110

Ile Tyr Trp Thr Val His Pro Ala Arg Ser Leu Gly Asp Tyr Glu Leu
        115                 120                 125

Asp Val Ser Pro Tyr Glu Asp Thr Val Thr Ser Lys Pro Trp Lys Met
    130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
                165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
        195                 200                 205

Ala Gln Gly Leu Leu Leu Cys Pro Cys Ala Pro Glu Asp Ala Gly Cys
    210                 215                 220
```

-continued

```
Gly Glu Arg Arg Arg Asn Thr Ile Ala Pro Ser Cys Ala Leu Pro Ser
225                 230                 235                 240

Val Thr Pro Asn Cys Leu Asp Leu Arg Ser Phe Cys Arg Ala Asp Pro
            245                 250                 255

Leu Cys Arg Ser Arg Leu Met Asp Phe Gln Thr His Cys His Pro Met
        260                 265                 270

Asp Ile Leu Gly Thr Cys Ala Thr Glu Gln Ser Arg Cys Leu Arg Ala
    275                 280                 285

Tyr Leu Gly Leu Ile Gly Thr Ala Met Thr Pro Asn Phe Ile Ser Lys
290                 295                 300

Val Asn Thr Thr Val Ala Leu Ser Cys Thr Cys Arg Gly Ser Gly Asn
305                 310                 315                 320

Leu Gln Asp Glu Cys Glu Gln Leu Glu Arg Ser Phe Ser Gln Asn Pro
            325                 330                 335

Cys Leu Val Glu Ala Ile Ala Ala Lys Met Arg Phe His Arg Gln Leu
        340                 345                 350

Phe Ser Gln Asp Trp Ala Asp Ser Thr Phe Ser Val Val Gln Gln Gln
    355                 360                 365

Asn Ser Asn Pro Ala Leu Arg Leu Gln Pro Arg Leu Pro Ile Leu Ser
370                 375                 380

Phe Ser Ile Leu Pro Leu Ile Leu Leu Gln Thr Leu Trp
385                 390                 395

<210> SEQ ID NO 54
<211> LENGTH: 431
<212> TYPE: PRT
<213> ORGANISM: Gallus gallus

<400> SEQUENCE: 54

Met Arg Gly Ile Leu Tyr Phe Cys Thr Leu Ile Leu Leu Glu Gly Met
1               5                   10                  15

Ala Glu Ala Val Ser Ser Ser Arg Asp Cys Leu Gln Ala Gly Glu Ser
            20                  25                  30

Cys Thr Asn Asp Pro Ile Cys Ser Ser Lys Phe Arg Thr Leu Arg Gln
        35                  40                  45

Cys Ile Ala Gly Asn Gly Ala Asn Lys Leu Gly Pro Asp Ala Lys Asn
    50                  55                  60

Gln Cys Arg Ser Thr Val Thr Ala Leu Leu Ser Ser Gln Leu Tyr Gly
65                  70                  75                  80

Cys Lys Cys Lys Arg Gly Met Lys Lys Glu Lys His Cys Leu Ser Val
                85                  90                  95

Tyr Trp Ser Ile His His Thr Leu Met Glu Gly Met Asn Val Leu Glu
            100                 105                 110

Ser Ser Pro Tyr Glu Pro Phe Ile Arg Gly Phe Asp Tyr Val Arg Leu
        115                 120                 125

Ala Ser Ile Thr Ala Gly Ser Glu Asn Glu Val Thr Gln Val Asn Arg
    130                 135                 140

Cys Leu Asp Ala Ala Lys Ala Cys Asn Val Asp Glu Met Cys Gln Arg
145                 150                 155                 160

Leu Arg Thr Glu Tyr Val Ser Phe Cys Ile Arg Arg Leu Ala Arg Ala
                165                 170                 175

Asp Thr Cys Asn Arg Ser Lys Cys His Lys Ala Leu Arg Lys Phe Phe
            180                 185                 190

Asp Arg Val Pro Pro Glu Tyr Thr His Glu Leu Leu Phe Cys Pro Cys
        195                 200                 205
```

-continued

```
Glu Asp Thr Ala Cys Ala Glu Arg Arg Gln Thr Ile Val Pro Ala
    210                 215                 220
Cys Ser Tyr Glu Ser Lys Glu Lys Pro Asn Cys Leu Ala Pro Leu Asp
225                 230                 235                 240
Ser Cys Arg Glu Asn Tyr Val Cys Arg Ser Arg Tyr Ala Glu Phe Gln
                245                 250                 255
Phe Asn Cys Gln Pro Ser Leu Gln Thr Ala Ser Gly Cys Arg Arg Asp
            260                 265                 270
Ser Tyr Ala Ala Cys Leu Leu Ala Tyr Thr Gly Ile Ile Gly Ser Pro
        275                 280                 285
Ile Thr Pro Asn Tyr Ile Asp Asn Ser Thr Ser Ser Ile Ala Pro Trp
    290                 295                 300
Cys Thr Cys Asn Ala Ser Gly Asn Arg Gln Glu Glu Cys Glu Ser Phe
305                 310                 315                 320
Leu His Leu Phe Thr Asp Asn Val Cys Leu Gln Asn Ala Ile Gln Ala
                325                 330                 335
Phe Gly Asn Gly Thr Tyr Leu Asn Ala Ala Thr Ala Pro Ser Ile Ser
            340                 345                 350
Pro Thr Thr Gln Met Tyr Lys Gln Glu Arg Asn Ala Asn Arg Ala Ala
        355                 360                 365
Ala Thr Leu Ser Glu Asn Ile Phe Glu His Leu Gln Pro Thr Lys Val
    370                 375                 380
Ala Gly Glu Glu Arg Leu Leu Arg Gly Ser Thr Arg Leu Ser Ser Glu
385                 390                 395                 400
Thr Ser Ser Pro Ala Ala Pro Cys His Gln Ala Ala Ser Leu Leu Gln
                405                 410                 415
Leu Trp Leu Pro Pro Thr Leu Ala Val Leu Ser His Phe Met Met
            420                 425                 430

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: a, c, t, g, other or unknown

<400> SEQUENCE: 55
tyyyyyyyyy ncag                                                     14

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccgcccttca ccagg                                                    15

<210> SEQ ID NO 57
<211> LENGTH: 15
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 57
ccgcccttca ccagg                                                      15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccgggcgcgc gcagg                                                      15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggggtccccc gcagg                                                      15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tctgcactcc gcaga                                                      15

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tcctaacgcc caagg                                                      15

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cttacccttc ctagg                                                      15
```

COMPOUNDS RELATED TO OR DERIVED FROM GFR α4 AND THEIR USE

CROSS-REFERENCE TO RELATED APPLICATION

This application is a National Stage entry of International Application No. PCT/FI00/00994, filed on Nov. 14, 2000, the entire specification claims and drawings of which are incorporated herewith by reference.

THE TECHNICAL FIELD OF THE INVENTION

The present invention discloses compounds related to, derived from or interacting with mammalian GFRα4, a glycosyl-phosphatidylinositol (GPI)-linked GDNF family α-receptor. The invention relates to the mammalian protein as such or derivatives (homologs) thereof, nucleic acid sequences encoding said protein or derivatives thereof as well as modulators or specific binding substances of said GFRα4 or GFRα4-related substances. The compounds are useful especially for diagnosing and treating neuronal or neurological disorders, endocrine cell related diseases as well as tumours by recording GFRα4-mediated signalling on said cells. The GFRα4 or GFRα4-like molecules or compounds interacting with said compounds are also useful for screening mimetics potentially useful as drugs.

THE BACKGROUND OF THE INVENTION

The GDNF family of neurotrophic factors includes four members: glial cell line-derived neurotrophic factor (GDNF), neurturin, artemin, and persephin (PSPN). GDNF family ligands signal through receptors consisting of a GPI-linked GFRα subunit and the transmembrane receptor tyrosine kinase RET. In order to activate the transmembrane receptor tyrosine kinase Ret, each of the GDNF family neurotrophic factors binds preferentially to one of the glycosyl-phosphatidylinositol (GPI)-linked GDNF family α-receptors (GFRα1-4) (Airaksinen et al., 1999). GFRα4, the preferential receptor for persephin (PSPN), has so far been described only from chicken (Enokido et al., 1998; Thompson et al., 1998). GDNF signals via GFRα1, neurturin via GFRα2, artemin via GFRα3, whereas the mammalian GFRα receptor for persephin (PSPN) and the biological role of GFRα4 has so far remained unclear.

RET-mutations are known to be related with inherited cancer syndrome (MEN2), characterized by medullary thyroid carcinoma (MTC) and with sporadic forms of MTC and pheochromocytoma, but it is not clear why different specific RET mutations associate with the different disease phenotypes, for example, why hyperparathyroidism and familial MTC associate with certain types of mutations whereas sporadic MTC is associated with other types of mutations. For example Ret is expressed in malignant thyroid C-cells and adrenal chromaffin cells but also in normal cells non-affected in MEN2, leaving the cause for the cell specificity of the MEN2 cancer syndrome unclear.

Studies of expression and splicing patterns with mouse and human GFRα4, surprisingly provided a response to the previous unclarities.

THE SUMMARY OF THE INVENTION

The novel cDNA sequences encoding GFRα4 and corresponding to the mammalian splicing forms of mRNA enable the manufacture of new useful tools for diagnosis and/or treatment of certain endocrine tumours and other diseases related to endocrine cells and/or neurons in mammals, especially humans as well as for identifying and producing new products mimicking the compounds of the present invention.

The present invention is related to an isolated and purified nucleic acid sequence, which is a cDNA encoding a splicing isoform of mammalian GFRα4 having the amino acid sequence (SEQ ID NO:1:), (SEQ ID NO:2:), (SEQ ID NO:3:), which are mouse derived or (SEQ ID NO:4:), (SEQ ID NO:5:) or (SEQ ID NO:6:), which are human derived. More specifically the cDNA sequences encoding human GFRα4 molecules are characterized by comprising the nucleic acid sequence (SEQ ID NO:10:), (SEQ ID NO:11:), (SEQ ID NO:12:) or (SEQ ID NO:13:). The genomic sequence (SEQ ID NO:13:) and fragments thereof including at least one of the exons (SEQ ID NO:29:), (SEQ ID NO:30:), (SEQ ID NO:31:), (SEQ ID NO:33:), (SEQ ID NO:35:), (SEQ ID NO:37:) or (SEQ ID NO:39:) or any combination thereof with or without introns or parts of the introns (SEQ ID NO:32:), (SEQ ID NO:34:), (SEQ ID NO:36:) or (SEQ ID NO:38:) still encoding a polypeptide having a functional activity substantially similar to that of human GFRα4.

The present invention is also related to the use of said nucleic acid sequence according to claims 1-5 for recording GFRα4-mediated signalling in neurons or endocrine cells.

The present invention is related to the use of nucleic acid sequence according to claim 1-3 for manufacturing polypeptides useful for diagnosing and/or treating tumours in parathyroid gland cells, adrenal chromaffin cells, cells of pituitary intermediate lobe, neoplasia, endocrine tumours, medullary thyroid carcinoma and pheochromocytoma or for treating neuronal or neurological disorders.

The present invention is also related to purified and/or isolated polypeptides having the amino acid sequence (SEQ ID NO:1:), (SEQ ID NO:2:), (SEQ ID NO:3:), (SEQ ID NO:4:), (SEQ ID NO:5:) or (SEQ ID NO:6:) or other peptides, which have a structure substantially similar to an isoform of mouse GFRα4 or of human GFRα4.

The present invention is related to the use of said polypeptides for determining GFRα4-mediated signalling in neurons or endocrine cells and for the use of said polypeptides for treating disorders and disease in the endocrine cells, such as thyroid calcitonin-producing C-cells, parathyroid gland cells, adrenal chromaffin cells or cells of pituitary intermediate lobe, such as medullary thyroid carcinoma including pheochromocytoma and parathyroid hyperplasia, as well as neuronal disorders.

The present invention also include the use of said polypeptides for manufacturing a composition for diagnosing and/or treating neuronal or neuronic disorders, osteoporosis, cancer in parathyroid gland cells, adrenal chromaffin cells and cells of pituitary intermediate lobe, in neoplasia, including treatment of endocrine tumours, including medullary thyroid carcinoma, pheochromocytoma and parathyroid hyperplasia.

The nucleic acid sequences and polypeptides of the present invention are also useful for recognizing substances which are mimetics of said sequences and are potentially useful as medicines for the diseases mentioned above.

Naturally the present invention is also related to methods for obtaining a cell-line (clone) useful in the production of cells, cell-lines and transgenic non-human animal.

The characteristics of the present invention are as defined in the claims.

DEPOSITION

The sequences reported in this paper have been deposited in the GenBank database and the accession numbers are listed below. Mus: AJ276870, AJ276871, AJ276872, AJ276514, AJ276515, AJ276516. Human: AJ291673, AJ291674, AJ291675

THE DETAILED DESCRIPTION OF THE INVENTION

Abbreviations

ARTN, artemin; FTA, follicular thyroid adenoma; FTC, follicular thyroid carcinoma; GDNF, glial cell line-derived neurotrophic factor; GFR, GDNF family receptor; MEN, multiple endocrine neoplasia; MTC, medullary thyroid carcinoma; NRTN, neurturin; PSPN, persephin; PTC, papillary thyroid carcinoma, SCG, superior cervical ganglion

DEFINITIONS

In the present invention the terms used have the meaning they generally have in the fields of biochemistry, pharmacology, recombinant DNA technology, including production of transgenic animal but some terms are used with a somewhat deviating or broader meaning than in the normal context. Accordingly, in order to avoid uncertainty caused by terms with unclear meaning some of the terms used in this specification and in the claims are defined in more detail below.

As used herein, "a neurotrophic factor" refers to a protein that modulates a biological activity of a cell, particularly neurons, but also other cells, through a neurotrophic factor signalling pathway, such as the RET signalling pathway, serine/threonine kinase Akt-mediated pathway or the RAS/MEK/MAPK pathway. Examples of biological activities in the present invention include, but are not limited to persephin.

As used herein, "RET signalling pathway" includes a cell, e.g., neural cell signalling pathway which involves the tyrosine kinase receptor RET. Said pathway includes the GDNF, neurturin, artemin and persephin signalling pathways, which neurotrophic factors bind specific GFRα coreceptors, GFRα1-GFRα4, which in turn bind and activate RET. As used herein "neurotrophic factor signalling pathway" includes a ligand, e.g. persephin (PSPN) independent signalling by GFRα4/RET or GFRα4 without RET.

As used herein, "a neurotrophic factor responsive cell" includes a cell which has a biological activity that can be modulated (e.g., stimulated or inhibited) by a neurotrophic factor. Examples of such functions include mobilization of intracellular molecules, which participate in a signal transduction pathway, production or secretion of molecules, alteration in the structure of a cellular component, cell proliferation, cell migration, cell differentiation, and cell survival. Cells responsive to neurotrophic factors preferably express a neurotrophic factor receptor, e.g., a GFRα receptor, such as GFRα4, and/or tyrosine kinase receptor, e.g., the tyrosine kinase receptor RET. Examples of neurotrophic factor responsive cells of the present invention include neurons, endocrine cells, such as thyroid C-cells and cells in adrenal medulla expressing GFRα4.

Depending on the type of cell, the response elicited by neurotrophic factors is different. For example, in neuronal cells, neurotrophic factors regulate neuron survival and neuronal function. Abnormal or aberrant activity of proteins involved in specific trophic signalling pathways, can lead to a variety of disorders, for example in the endocrine system, e.g., abnormal growth (dysplasia or hyperplasia) as well as abnormal development, differentiation or function of the cells.

Abnormal or aberrant activity of a GFRα4-protein (or abnormal or aberrant nucleic acid expression of the nucleic acid encoding said protein in a neurotrophic signalling factor pathway, in the nervous system or the endocrine system includes the above mentioned disorders in cells expressing or missexpressing GFRα4.

In addition, neurotrophic factors, as such or combined with GDNF, artemin and neurturin and the interaction with GFRα-receptors also promote proper development of a variety of cell types. For example, neurotrophic factor/receptor interactions promote development, differentiation or function of certain peripheral organs and cells of the nervous system, innervation associated with said organs, tissues or cells. Activity of GFRα4 signalling pathway in endocrine systems can lead to disorders including tumours associated with cellular development of cells of these organs as shown in the present RET invention. For example, axonal sprouting in epilepsy due to compensatory neurotrophic factor production after seizures may aggravate the disease process. Augmenting GFRα4 type of signaling in such conditions could be useful by preventing neuronal death without producing aberrant sprouting.

The term "GFRα4" in the present invention means mammalian GFRα4 and/or GFRα4-like or GFRα4-derived protein molecules or polypeptides, i.e. soluble receptor analogues expressed by and being substantially homologous to GFRα4 at amino acid level. Said GFRα4-like or GFRα4-derived molecules defined in the claims are obtainable by isolation from natural mammalian, e.g. human or murine sources as different splicing forms. Said splicing forms lack the first Cys-rich domain characteristic of other GFRα receptors or said domain is easily spliced off during transcription or translation. The GFRα4-like molecules of the present invention can also be produced by synthetic, semisynthetic, enzymatic and other biochemical or chemical methods including recombinant DNA techniques.

The amino acid sequences of the splicing isoforms or variants of mammalian GFRα4 are listed below:
(SEQ ID NO:1:) murine GPI-anchored isoform a1 FIG. 18B;
(SEQ ID NO:2:) murine putative transmembrane isoform a2 FIG. 19B;
(SEQ ID NO:3:) murine secreted isoform a3/4 FIG. 20B;
(SEQ ID NO:4:) human GPI-anchored isoform a FIG. 21B;
(SEQ ID NO:5:) human putative GPI-anchored isoform b FIG. 22B;
(SEQ ID NO:6:) human putative soluble isoform c FIG. 23B.

Polypeptide fragments useful for identifying and isolating nucleotide sequences encoding the above amino acid sequences are (SEQ ID NO:14:), (SEQ ID NO:15:), (SEQ ID NO:16:) and (SEQ ID NO:17:).

The "GFRα4-like or GFRα4-derived molecules" are substantially homologous with the amino acid sequences of mouse origin (SEQ ID NO:1:), (SEQ ID NO:2:), (SEQ ID NO:3:) as well as of human origin (SEQ ID NO:4:), (SEQ ID NO:5:) or (SEQ ID NO:6:). They all lack the first Cys-rich domain characteristic of other GFRα receptors and chicken GFRα4. The "GFRα4-like or GFRα4-derived molecules" are characterized by comprising polypeptides such as the amino acid sequences (SEQ ID NO: 24:), (SEQ ID NO:15:), (SEQ ID NO:16:) and/or (SEQ ID NO:17:) or amino acid sequences being truncated at the N-terminal or C-terminal end of the murine or human amino acid sequences (SEQ ID NO:1:), (SEQ ID NO:2:), (SEQ ID NO:3:), (SEQ ID NO:4:), (SEQ ID NO:5:), (SEQ ID NO:6:), but still covering the contagious and/or overlapping regions of the mammalian sequences (SEQ ID NO:1:), (SEQ ID NO:2:), (SEQ ID NO:3:), (SEQ ID NO:4:), (SEQ ID NO:5:), (SEQ ID NO:6:).

The term "substantially homologous" at amino acid level means that the GFRα4-like protein molecules have a significant similarity or identity of at least 80%, preferably 85%, most preferably more than 90% with proteins encoded by human genomic sequence GFRα4 (SEQ ID NO:13:)

In the present invention "homology" is determined e.g. using BLAST analysis combined with database searches matching the above defined expressed sequence tags (ESTs) with known sequences in the data bases. Nucleotide and amino acid sequence comparisons are also performed with (BestFit), alignment (PileUp), and phylogenetic tree (GrowTree). Also used are as signal sequence and transmembrane hydrophobicity plots (PeptideStructure) with the SeqWeb program package (Genetics Computer Group, Inc.).

The term "GFRα4-like molecules and derivatives thereof" comprise polypeptides having the structure, properties and functions characteristic of GFRα4-like molecules. Thus, the term "GFRα4-like molecules and derivatives thereof" includes GFRα4-like molecules, wherein one or more amino acid residues are replaced by another amino acid residue. Also truncated, complexed or chemically substituted, forms of said GFRα4-like molecules are included in the term "GFRα4-like molecules and derivatives thereof". Chemically substituted forms include for example, alkylated, esterified, etherified or amidized forms preferably with a low substitution degree. Especially, useful are substitutions with small molecules, such as methyl or ethyl and a low substitution degree, because said small molecules and/or low substitution degrees, while stabilizing and modifying the GFRα4-molecules of the present invention, are not prone to change or disturb the properties and functions of the GFRα4-like molecules. The truncated, complexed and/or substituted variants of said GFRα4-like polypeptides can be produced by synthetic or semisynthetic methods, including enzymatic and recombinant DNA techniques. The only other prerequisite is that the derivatives still are substantially homologous with and have the properties and/or express the functions of the domains of GFRα4 and can be used for screening compounds mimicking the binding substances of GFRα4.

The isolated GFRα4 molecules should preferably comprise amino acid sequences which are at least about 70-80% or more homologous to the murine and human amino acid sequences defined above and should be characterized by at least one but preferably several of the following activities:

1) it can interact with (e.g. bind to) a neurotrophic factor, e.g. PSPN.

2) it can interact (e.g. bind to) a tyrosine kinase receptor, e.g., the tyrosine kinase receptor RET;

3) it can modulate the activity of a tyrosine kinase receptor, e.g., the tyrosine kinase receptor RET; and 4) it can bind a neurotrophic factor and modulate a response in endocrine cells, e.g., thyroid C-cells The term "GFRα4-like molecules" otherwise covers all possible splice variants of GFRα4 expressed by mammalian tissues possibly excluding certain rat sequences, which are the thyroid, especially thyroid C-cells, and parathyroid glands and cells in adrenal medulla and the pituitary intermediate lobe, and possibly cells of the nervous system.

As a conclusion "GFRα4-like molecules" in its broadest aspect in the present invention, covers not only GFRα4-like molecules derived from nature, including their isoforms of different origin, but also synthetically, semisynthetically, enzymatically produced GFRα4-like molecules including molecules produced by recombinant DNA techniques. Said GFRα4-like molecules can be used either as separate entities or in any combinations.

The term "isoform" refers to the different forms of the same protein, which originate from different sources, e.g. different mammalian species, e.g. human and murine sources in the present case. In the present invention the term, thus, includes fragments, complexes and their derivatives. For example, GFRα4-like molecules can be generated by the cleavage of the corresponding preproprotein. Different reactions, including different enzymatic and non-enzymatic reactions, proteolytic and non-proteolytic, are also capable of creating truncated, derivatized or complexed forms of the GFRα-molecules.

Preferably, all "GFRα4-like molecules and their derivatives" should be recognizable using binding substances capable of recognizing the native mammalian, including human and murine GFRα4 or GFRα4-like molecules. Such binding substances are for example the neurotrophic factor PSPN and/or fragments thereof and antibodies specifically recognizing GFRα4.

In the present invention the term "nucleic acid sequence" means any isolated and purified nucleic acid sequences encoding mammalian GFRα4 and/or GFRα4-like substances or nucleic acid sequences with substantial similarity still encoding GFRα4-like molecules having an amino acid sequence substantially homologous with the murine sequences (SEQ ID NO:1:), (SEQ ID NO:2:) or (SEQ ID NO:3:) and/or the human sequences (SEQ ID NO:4:), (SEQ ID NO:5:) or (SEQ ID NO:6:), lacking the first Cys-rich domain characteristic of other GFRα receptors (GFRα1, GFRα2, GFRα3). Preferably the nucleic acid sequence should encode or express a polypeptide having the characteristics described above and at least one contiguous amino acid sequence (SEQ ID NO:14:), (SEQ ID NO:15:), (SEQ ID NO:16:) and/or (SEQ ID NO:17:).

The nucleic acids sequences of the present invention belong to the functionally active GFRα4-related compounds of the present invention and they can be used as such or they can be introduced into suitable transformation or expression vectors, which in turn can be introduced into suitable host organisms to provide procaryotic, eukaryotic organisms capable of expressing altered levels of GFRα4 as well as transgenic animals, e.g. knockout mice useful as test animals.

The "nucleic acid sequences" are selected from a group consisting of murine and human cDNAs listed below:

(SEQ ID NO:7:) murine cDNA a1 FIG. 18A (SEQ ID NO:8:) murine cDNA a2 FIG. 19A (SEQ ID NO:9:) murine cDNA a3/4 FIG. 20A (SEQ ID NO:10:) human cDNA (GPIa) FIG. 21A (SEQ ID NO:11:) human cDNA (GPIb) FIG. 22A (SEQ ID NO:12:) human cDNA c FIG. 23A (SEQ ID NO:13:) human genomic FIG. 24

Nucleotide fragments useful as probes or primers in hybridization or PCR-techniques and for identifying and synthetically preparing the human genomic sequence are (SEQ ID NO:18:), (SEQ ID NO:19:), (SEQ ID NO:20:), (SEQ ID NO:21:), (SEQ ID NO:22:), (SEQ ID NO:23:), (SEQ ID NO:24:), (SEQ ID NO:25:), (SEQ ID NO:26:), (SEQ ID NO:27:), (SEQ ID NO:28:), (SEQ ID NO:29:), (SEQ ID NO:30:), (SEQ ID NO:31:), (SEQ ID NO:33:), (SEQ ID NO:35:), (SEQ ID NO:37:), (SEQ ID NO:39:), (SEQ ID NO:40:). The introns of the human genomic sequence include 5 introns, the first being an unsequenced about 500 bp long sequence situated between the nucleotides 97 and 98 in (SEQ ID NO:13:), (SEQ ID NO:41:), (SEQ ID NO:42:), (SEQ ID NO:43:), (SEQ ID NO:44:), (SEQ ID NO:45:), (SEQ ID NO:46:), (SEQ ID NO:47:), (SEQ ID NO:48:), (SEQ ID NO:49:) and/or (SEQ ID NO:50:). The second intron has the sequence (SEQ ID NO:32:), the third intron has the sequence (SEQ ID NO:34:), the forth intron has the sequence (SEQ ID NO:36:) and the fifth intron has the sequence (SEQ ID NO:38:). It is to be noted that the splicing variants may comprise introns or parts thereof.

The "nucleic acid sequences" of the present invention are not in their natural state but are isolated from their natural environment as transiently expressed mRNAs from different mammalian tissue. Thereafter, the mRNAs are purified and multiplied in vitro in order to provide by technical means new copies, which are capable of encoding said mammalian GFRα4 or substantially homologous "GFRα4-like molecules" of the present invention. Also the genomic sequence (SEQ ID NO:13:) and its complementary sequence are reprosuced by copying the original strand or overlapping fragments thereof.

The isolated nucleic acid sequences of the present invention also include the human GFRα4 encoding nucleic acid sequences SEQ ID NO:10:, SEQ ID NO:11: or SEQ ID NO:12:, which are a cDNAs identified by aid of the mRNAs from cDNA libraries from human thyroid and adrenal tissues as well as the genomic sequence (SEQ ID NO:13:) encoding and expressing a GFRα4 protein or fragments thereof, which act as a receptor of the corresponding ligand, e.g. persephin.

The term "genomic sequence" means the corresponding sequence present in the nucleus of the mammalian cells and comprising introns as well as exons. In the present invention the genomic sequence is included as such and/or as separate exons or introns or combinations thereof. The splicing variants for example may contain exons and part of introns as shown in the examples.

In the present context the term "cDNA" means a DNA sequence obtainable by reversed transcription of mRNA transcribed from the genomic DNA sequence. In the present invention the term cDNA also include the complementary strand of the original cDNA. Thus, nucleotide sequences hybridizing with the cDNA include both sequences substantially identical with the cDNA made as a copy of the respective mRNA but also the complementary strands and/or antisense strands. Genomic sequences copied are also included in the term cDNA.

The term "nucleic acid sequence encoding or expressing GFRα4-like molecules" means nucleic acid sequences as well as substantially homologous nucleic acid sequences, which comprise at least one contiguous nucleic acid sequence selected from a group consisting of murine sequences (SEQ ID NO:7:), (SEQ ID NO:8:) or (SEQ ID NO:9:) as well as the human sequences (SEQ ID NO:10:), (SEQ ID NO:11:), (SEQ ID NO:12:) or (SEQ ID NO:13:)

Among especially preferred nucleic acid sequences the contiguous sequences (SEQ ID NO:10:), (SEQ ID NO:11:) or (SEQ ID NO:12:) deduced from human cDNA can be mentioned. This sequence or their complementary sequences or nucleic acid sequences comprising parts thereof, e.g. fragments of said nucleotide sequences truncated at the 3'-terminal or 5'-terminal end, as well as sequences containing point mutations or SNPs caused by single nucleotide polymorphism are especially useful as probes for detecting nucleic acid sequences of the present invention.

Specific nucleic acid sequences useful as primers and/or probes are the nucleotide sequences (SEQ ID NO:18:), (SEQ ID NO:19:), (SEQ ID NO:20:), (SEQ ID NO:21:), (SEQ ID NO:22:), (SEQ ID NO:23:), (SEQ ID NO:24:), (SEQ ID NO:25:), (SEQ ID NO:26:), (SEQ ID NO:27:) and/or (SEQ ID NO:28:), (SEQ ID NO:29:), (SEQ ID NO:30:), (SEQ ID NO:31:), (SEQ ID NO:33:), (SEQ ID NO:35:), (SEQ ID NO:37:), (SEQ ID NO:39:), (SEQ ID NO:40:), (SEQ ID NO:41:), (SEQ ID NO:42:), (SEQ ID NO:43:), (SEQ ID NO:44:), (SEQ ID NO:45:), (SEQ ID NO:46:), (SEQ ID NO:47:), (SEQ ID NO:48:), (SEQ ID NO:49:) or (SEQ ID NO:50:).

It is, however, clear for those skilled in the art that other nucleic acid sequence capable of encoding GFRα4-like molecules and useful for their production can be prepared based on this information. The nucleic acid sequences encoding GFRα4-like molecules should be capable of hybridizing under stringent condition varying e.g between 58° C., 2×SSC and 65° C., 0.1×SSC (Sambrook, J., et al., Molecular Cloning: A Laboratory Manual., Cold Spring Harbor, N.Y.: Cold Spring Harbor Laboratory, 1989) with sequence encoding the domain of the GFRα4 or parts thereof.

The nucleic acid sequences of the present invention should have a substantial similarity with the SEQ ID NO:10:, SEQ ID NO:11: or SEQ ID NO:12. "Substantial similarity" in this context means that the nucleotide sequences fulfill the prerequisites defined above and have a significant similarity, i.e. a sequence identity of at least 60%, preferably 70', most preferably more than 80% with the nucleotide sequences encoding the murine amino acid sequences (SEQ ID NO:1:), (SEQ ID NO:2:) or (SEQ ID NO:3:) as well as the human amino acid sequences (SEQ ID NO:4:), (SEQ ID NO:5:) or (SEQ ID NO:6:).

The term "nucleic acid sequences encoding human GFRα4 or GFRα4-like molecules" include their truncated or complexed forms as well as point mutations of said nucleic acid sequences as long as the GFRα4-like molecules are capable of encoding amino acid sequences having the essential structural features as well as the properties and/or functions of GFRα4-like molecules. The functions of the GFRα4 or GFRα4-like molecules or the compounds interacting with said compounds can be measured with methods generally used for measuring the GDNF family receptor-GFRα mediated signalling including the method disclosed in the example(s) below.

The nucleic acid sequences are useful as such, for preparing transformation vectors and/or expression vectors as well as host cells carrying nucleic acid sequences capable of expressing the desired protein. They are capable of encoding/expressing GFRα4 or GFRα4-like proteins or fragments thereof. The GFRα4 or GFRα4-like molecules or compounds interacting with said molecules are useful for identifying or recognizing compounds mimicking said compounds, respectively. Binding substances are for example antibodies, receptors as well as shorter binding peptides, which specifically bind and recognize GFRα4 or GFRα4-like molecules or compounds interacting with said compounds. Said substances are useful especially for screening mimetics which may be useful in therapeutic or diagnostic applications. Such methods are well known to those skilled in the art. Examples of such methods it is referred to the following patent applications EP 639 584, WO 9638553, U.S. Pat. No. 5,571,506, WO 200018790, WO 9950439, WO 9945930, U.S. Pat. No. 6,030,619 and/or WO 9906599 which by reference are incorparated into the specification of the present invention.

The GFRα4-like molecules can be identified and their amounts can be measured using "binding substances". The term "binding substance" means any substances capable of specifically recognizing and binding the GFRα4-like molecule or derivatives thereof or at least one specific portion of said GFRα4 molecules. Such substances are, ligands of the GFRα4 receptor or other binding proteins or peptides, comprising e.g. specific portions of the GDNF family neurotrophic factor, especially persephin (PSPN), capable of specifically binding GFRα4-like molecules and taking part in the signalling specific for GFRα4. Above all binding substances mean antibodies capable of specifically recognizing one or more GFRα4-like molecules alone or in any combination. The antibodies include both polyclonal and/or monoclonal antibodies as well as fragments thereof. Preferably, such binding substances recognize and bind to specific epitopes or active sites of the GFRα4-like molecules.

Said binding substances can be produced using specific domains of GFRα4 or any GFRα4-like molecules, their isoforms as well as their fragments, derivatives or complexes with the prerequisite that they are capable of acting as "antigens". The antigens include any compositions or materials capable of eliciting an antibody response specific to said GFRα4 or GFRα4-like molecules or compounds interacting with said molecules. Ligands of GFRα4-receptors, in other words specific neurotrophic factors are also included in the term binding substances. Said binding substances, preferably antibodies can be produced by conventional techniques for producing polyclonal antibodies as well as monoclonal antibodies. The methods for preparing monoclonal antibodies include hybridoma techniques. Fragments of antibodies or other binding proteins such as specific binding peptides can be developed by phage display techniques and produced by recombinant DNA techniques. All methods are well known by those skilled in the art and described in laboratory handbooks.

The term "screening" means that arrays of substances produced or recognized e.g. by combinatorial chemistry, with genomics or proteomics can be screened against the GFRα4 compounds of the present invention or their binding substances in order to find compounds mimicking the properties or effects of said GFRα4 or GFRα4-like molecules and/or their binding substances are potentially useful as drugs or as models for developing further compounds. The results can be analyzed by methods provided by efficient tools in modern bioinformatics.

The term "diagnosing" means judging, predicting, assessing and/or evaluating as well as identifying and characterizing, including screening, whether a person is susceptible of or suffers from endocrine cell related diseases or disorders in neurons, e.g. neurite outgrowth leading to neuronal death or aberrant sprouting. The diagnoses also enable evaluation of the severity of the condition, therapy required as well as the efficacy of treatment modalities or medical treatments needed. Especially, early identification of the disease, e.g. neuronal or neurological disorders in order to start prophylactic and/or other treatments before the onset of the actual disease is a desirable feature, enabled by the present invention.

The results are recordable with means for performing immunoassays using GFRα4-like molecules and/or their binding substances as well as parts thereof. Means for performing amplification and hybridization methods using sequence specific probes or primers, which can be selected from the parts of the nucleic acid sequence fragments encoding suitable domains of mammalian, especially human GFRα4.

The term "screening" may also mean the screening of a population for the presence or absence e.g. of autoantibodies. This screening means that based on the fact that people or subjects susceptible of or suffering from complications related to a certain said disease caused by GFRα4 or GFRα4-like molecules or compounds interacting with said compounds suffer from aberrant expression patterns which may elicit antibody production not occurring in subjects not suffering from the disorder. These so called autoantibodies can be determined using GFRα4-like molecules. It is easy to screen a large population for the susceptibility of a certain diseases from blood or serum samples obtained from inflowing serum samples taken during routine diagnostic tests. If such autoantibodies can be detected in the serum of a person, it is a clear indication that the person in question is a potential patient and might be susceptible also to endocrine cell-related diseases or neurologic disorders and should be treated appropriately.

The term "immunoassay" refers to a immunochemical method or procedure capable of detecting and/or measuring at least one substance, either GFRα4 or GFRα4-like molecules or compounds interacting with said molecules or autoantibodies against said molecules using per se known means for performing an immunoassay, which means include a substance capable of specifically recognizing the substance to be determined, i.e. either at least one binding substance or a GFRα4 or GFRα4-like molecules or compounds interacting with said molecules or fragments thereof, for the desired application, respectively.

Well known examples of immunoassays are radioimmunoassays (RIA), radioimmunometric assays (IRMA), fluoroimmunometric assays (IFMA) enzyme immunoassays (EIA), enzyme-linked immunosorbent assays (ELISA), fluoroimmmunoassays (FIA), luminescence immunoassays, immunoagglutination assays, turbidimetric immunoassays, nephelometric immunoassays, etc. All methods are well known by those skilled in the art and described in laboratory handbooks.

The preparation and development of methods and means for measuring different antigens and antibodies, which can be applied also to the determination of GFRα4-like molecules and their autoantibodies have been described for example in the following patent publications applicable as convenient kits U.S. Pat. No. 5,591,645, U.S. Pat. No. 5,712,170, U.S. Pat. No. 5,602,040, U.S. Pat. No. 5,622,871, U.S. Pat. No. 5,656,503, EP 149 168, U.S. Pat. No. 4,552,839, U.S. Pat. No. 4,361,537, U.S. Pat. No. 4,373,932, WO 86/04683, EP 154 749, EP 7654, WO 86/03839, EP 191 640, EP 212 599, U.S. Pat. No. 4,552,839, EP 158 746, EP 225 054 and which are herewith incorporated by reference. Even if said patents are restricted to the development of test kits for diagnosing other diseases by aid of binding substance recognizing the respective active molecule, the man skilled in the art can use the information for developing corresponding test kits for measuring GFRα4-like molecules of the present invention.

Any immunochemical test methods can in principle be used for diagnosing endocrine diseases as well as for longitudinal or latitudinal screening of the progress of disease and effect of medical treatment. However, visual agglutination, flow-through and immunochromatographic methods are best suited for rapid assays or tests.

The term "prophylactic treatment" includes specific measures and/or precautions, e.g. control including possible medication, before the onset of disease. After the on-set of disease, prophylactic treatment requires therapeutic treatment as a precaution in order to avoid further complications.

The term "therapeutic treatment" includes methods for treating persons by administrating a compositions comprising GFRα4 or GFRα4-like molecules or compounds interacting with said compounds, including GFRα4-like polypeptides or GFRα4-binding substances. Nucleic acid sequences encoding the same are useful in gene therapy or for preventing the genes causing the disease from expressing the gene products causing the diseases.

The term "preparation or compositions" means the active ingredients of the present invention including the nucleic acid molecules encoding GFRα4, GFRα4-like proteins and/or polypeptides, GFRα4 modulators and antiGFRα4 antibodies in combination with at least one pharmaceutically acceptable carrier, which is compatible with the active ingredient, i.e. GFRα4 or GFRα4-like molecules or compounds interacting with said compounds and the route of administration. The nucleic acid molecules of the present invention can be used in gene therapy by introducing the molecules to suitable vectors or other per se known delivery systems. The pharmaceutical compositions can be included in a container, pack or dispenser together with instructions for use.

The nucleic acid molecules, proteins, protein homologues, modulators and antibodies described can be used in drug-screening assay, diagnostic assays, methods of treatment, pharmacogenomics, proteonomics, bioinformatics and/or monitoring of effects during clinical trials.

The nucleic acids of the present invention can be used to provide mammalian vectors which in turn can be introduced into mammalian cells. Suitable expression systems for pro- and eukaryotic cells are described in Sambrook et al., 1989. The host cells can be used for expressing the GFRα4-like proteins of the present invention.

The DNA constructs, vector construct and/or host cells of the present invention can also be used to produce non-human transgenic animals useful in screening assays designed to identify agents or compounds, drugs, pharmaceuticals, etc., which are capable of ameliorating detrimental systems related to specific neurons and/or endocrine cells. Especially useful are knockout mice capable of expressing altered levels of GFRα4.

The molecules, including nucleic acid sequences, GFRα4 or GFRα4-like molecules interacting with said compounds and the products developed, characterized and/or produced based on said molecules or compounds of the present invention are useful for studying the role of GFRα4-mediated signalling in neurons, in neoplasia, in endocrine cells and in thyroid calcitonin-producing C-cells (correlated with osteoporosis), parathyroid gland cells, adrenal chromaffin cells, cells of pituitary intermediate lobe, endocrine tumours, medullary thyroid carcinoma, pheochromocytoma, parathyroid hyperplasia and association with specific mutations in the RET oncogene as well as in nervous system and testis.

THE GENERAL DESCRIPTION OF THE INVENTION

The present invention is related to GFRα4 or GFRα4-like molecules or compounds interacting with said molecules which GFRα4-molecules are members of the GDNF protein family including glial-cell derived neurothrophic factor (GDNF), neurturin, artemin and persephin signal through receptors consisting of GPI-linked GFRα subunits and the transmembrane tyrosine kinase Ret, but also other signalling pathways.

The present invention is based on preliminary studies made with mouse Gfra4 which was characterized and shown to undergo developmentally regulated alternative splicing in several tissues. The results also indicated that mammalian GFRα4 receptor lacked the first Cys-rich domain characteristic of the other GFRα receptors.

The glial cell line-derived neurotrophic factor (GDNF) family ligands GDNF, neurturin (NRTN), artemin (ARTN) and persephin (PSPN) are structurally related neurotrophic factors that signal through a multicomponent receptor composed of the transmembrane receptor tyrosine kinase RET and high affinity glycosyl-phosphatidylinositol (GPI)-anchored proteins, the GDNF family alpha receptors 1-4 reviewed by Airaksinen, et al., 1999 and Baloh, et al., 2000. GFRα4 was first described from chicken and shown to be the preferential receptor for PSPN (Enokido, et al., 1998; Thompson, et al., 1998).

The mouse GFRα4 receptor described herein was also disclosed by Lindahl, et al., 2000 after the filing of the priority application. It differs from all other GFRα receptors, including chicken GFRα4 by being smaller in size and lacking the first Cys-rich domain. Mouse Gfra4 transcripts were shown to be expressed in many embryonic and adult tissues but efficient splicing leading to a functional GPI-linked isoform, as well as putative transmembrane and soluble isoforms, occurred only in thyroid and adrenal medulla and in pituitary intermediate lobe. In mouse, Gfra4 and Ret were co-expressed only in the thyroid C-cells and adrenal chromaffin cells. In chicken, Gfra4 mRNA was broadly expressed during embryonic development, including the spinal motoneurons and kidney (Thompson, et al., 1998). Chicken GFRα4 has been shown to bind mouse PSPN and to confer a survival response to PSPN in the presence of Ret (Enokido, et al. (1998). However, due to different structures of chicken and mammalian GFRα4, as well as the lack of information about the existence of chicken GFRα3, ligand-specificity of mammalian GFRα4 cannot be directly extrapolated from experiments with chicken GFRα4.

It is known that PSPN mRNA is expressed at low levels in many rat tissues, where two transcripts, an unspliced and a functional spliced form are produced (Milbrandt, et al., 1998; Jaszai, et al., 1998). PSPN is known to promote the survival of embryonic motor neurons in vitro and to rescue nigral dopamine neurons following neurotoxic injury in vivo but not to support the survival of any peripheral neurons tested (Milbrandt, et al., 1998). However, unlike GDNF and NRTN, PSPN does not induce neurite outgrowth of rat P8 motor axons in organotypic cultures (Ho, et al., 2000).

Somatic rearrangements were known to cause chromosomal inversions which activate the oncogenic potential of RET in human papillary thyroid carcinomas, whereas germ-line point mutations are known to be responsible of multiple endocrine neoplasia type 2 (MEN2; reviewed in Edery, et al., 1997; Eng, et al., (1999); Ponder, et al., 1999).

The malignancies associated with these syndromes are known to arise in several neural crest-derived cell populations. MEN2A is characterized by medullary thyroid carcinoma (MTC), pheochromocytomas and parathyroid hyperplasia, whereas MEN2B is characterized by MTC associated with pheochromocytomas, enteric ganglioneuromas, skeletal abnormalities and mucosal neuromas. MTC is the only phenotype in familial medullary thyroid carcinoma (FMTC). In MEN2A, cysteine substitutions in the extracellular domain of RET cause aberrant homodimerization and ligand-independent constitutive activation of RET (Santoro, et al., 1995; Iwashita, et al., 1996), which alone or together with unknown factors cause the malignant proliferation of cells. FMTC mutations are more evenly distributed among the extracellular cysteines but are also found in the intracellular part of RET. It is known that most cases of MEN2B are caused by a specific mutation in the tyrosine kinase domain, which is also frequently found in sporadic MTC. MEN2B is caused by constitutive activation of RET with altered substrate specificity in downstream signalling pathway (Santoro, et al., 1995); Iwashita, et al., 1996).

However, in MEN2B-RET transfected cells, ligand binding has been reported to increase the intensity of RET signalling (Carlomangno, et al., 1998; Bongarzone, et al., 1998). It has been shown that transgenic mouse models of these mutations cause some of the malignant phenotypes found in human MEN2 syndrome (Michiels, et al., 1997; Smith-Hicks, et al., 2000). Phenotypic variability within the same MEN2 family and between different families carrying the same mutation in RET, suggests that further genetic events or modifier genes are required to induce the tumor phenotype in MTC.

The mouse Gfra4 cDNA and genomic DNA sequence described in the present invention was characterized by having an unusual structure. The Gfra4 pre-mRNA was alternatively spliced in tissue-specific manner that was developmentally regulated. A splice variant of Gfra4 encoding GPI-linked isoform of GFRα4 was selectively expressed in juvenile thyroid C-cells and parathyroid gland. In contrast, newborn and adult thyroid, parathyroid, pituitary and adrenal glands produced another Gfra4 mRNA species, which encodes a putative transmembrane-anchored isoform. Ret-deficient mice were shown to have significantly less C-cells than their wild type littermates suggesting that thyroid C-cells and possibly adrenal chromaffin cells require GFRα4-Ret-signalling, which may specify tissues affected by the MEN2 cancer syndromes.

The nucleic acid sequences of the present invention encode an isoform of mouse or human GFRα4 comprising the murine amino acid sequence (SEQ ID NO:1:), (SEQ ID NO:2:) or (SEQ ID NO:3:) as well as the human amino acid sequences (SEQ ID NO:4:), (SEQ ID NO:5:) or (SEQ ID NO:6:). Preferably, the sequences are cDNAs of murine origin having the sequence (SEQ ID NO:7:), (SEQ ID NO:8:) or (SEQ ID NO:9:) as well as the cDNAs of human origin (SEQ ID NO:10:), (SEQ ID NO:11:) or (SEQ ID NO:12:) encoding isoforms of mammalian GFRα4. Also included among the nucleic acid sequences of the present invention are the genomic sequence of human GFRα4 locus (SEQ ID NO:13:).

Originally, a murine GFRα4 nucleic acid sequences was identified by the aid of available genomic sequences in formation of mouse mahogany gene locus (Gunn et al., 1999, Genebank AF155960). Within this genomic region, an "open reading frame" was identified that encoded a protein that showed sequence homology to chicken GFRα4. Probes were generated based on portions of the genomic sequence and cDNA libraries were screened with said probes. Nucleotide sequences were determined and assembled and various methods such as RACE and genomic sequence analysis were used to extend the 5' sequence. Examples of the mammalian nucleotide sequences which were found and which encoded GFRα4 were the mouse cDNAs (SEQ ID NO:7:), (SEQ ID NO:8:), (SEQ ID NO:9:) as well as the human cDNAs (SEQ ID NO:10:), (SEQ ID NO:11:), (SEQ ID NO:12:) or (SEQ ID NO:13:) and the predicted amino acid-sequences were the mouse originated sequences (SEQ ID NO:1:), (SEQ ID NO:2:) or (SEQ ID NO:3:) as well as the human originated sequences (SEQ ID NO:4:), (SEQ ID NO:5:) or (SEQ ID NO:6:) also shown in FIGS. 18-24.

The present inventors also isolated and characterized the human GFRα4 receptor and showed that it is a functional co-receptor for PSPN, which mediates RET activation. Selective co-expression of GFRA4 and RET in normal and malignant C-cells and developing adrenal gland suggested that GFRA4 is a candidate modifier gene in medullary thyroid carcinoma and pheochromocytoma associated with the MEN syndromes.

The present invention is based on the amino acid and/or nucleic acid sequence defined above and in the claims, especially, the GFRα4 cDNA, that encodes a specific member of the Glial Derived Neurotrophic Factor-Alpha Family of Receptors, i.e. the GFRα4 protein, which functions in neurotrophic factor signalling pathways.

The first mammalian members of the GFRα4 subfamily were identified, as described herein. Gfra4 was expressed in many mouse tissues including nervous system, where intron retention leads to a putative secreted GFRα4 protein. Efficient splicing was shown to occur only in thyroid, parathyroid, pituitary, and less in adrenal glands. A splice form leading to a GPI-linked GFRα4 receptor was shown to be expressed in juvenile thyroid as well as in parathyroid and pituitary glands.

Significant loss of thyroid C-cells in Ret-deficient mice suggested that C-cells, and cells in adrenal medulla also express Ret and may require signalling via GFRα4-Ret receptor. Finally, GFRα4 expression may restrict the inherited cancer syndrome multiple endocrine type 2, associated with mutations in RET, to these cells. These preliminary hypothesis were supported by further observations as disclosed below.

The first GFRα4 proteins isolated were expected to bind to neurotrophic factors, especially GDNF-family ligands, and mediate signals within cells expressing the GFRα4 protein. As expected, it was shown that the GFRα4 protein transmitted a signal to the interior of the cell by activation of the RET protein tyrosine kinase signalling pathway. Neurotrophic factors are known to promote survival and function of neural cells of both the central and peripheral nervous systems. Thus, modulation of the activity of a molecule involved in transmitting a neurotrophic factor signal to a cell results in modulation of the neurotrophic factor initiated cell function. Consequently, the ability of GFRα4 to modulate neurotrophic factor initiated cell functions were tested. It was shown that GFRα4 can be used to modulate neurotrophic factor action and/or activity and thereby GFRα4 is useful for treating disorders associated with such functions (or lack thereof).

In addition, GFRα4 mRNAs were expressed in a variety of tissues, especially, during embryogenesis, including, for example, cells of the pituitary gland and the intermediate lobe. Thus, modulators of GFRα4 can be used to modulate development of these tissues and thereby to treat disorders associated with abnormal or aberrant development of these various tissues.

The molecular mechanisms by which the mutated Ret alleles contribute to the development of neuroendocrine neoplasms in MEN-2 syndromes is largely unknown. The effects of tyrosine kinase receptors are known to be mediated by the concerted activation of several signalling pathways including those of phospholipase C—, phosphatidylinositol 3-kinase, and the Ras/mitogen-activated protein (MAP) kinase (also known as ERK) (Kazlauskas, et al., 1994). In a rat pheochromocytoma cell line, PC12, activation of the Ras signalling cascade is a prerequisite for nerve growth factor (NGF)-induced cell differentiation (D' Arcangelo, et al., 1993).

Although Ras is implicated in Ret-induced neuronal differentiation, little is known about the contribution of this pathway to the biological effects triggered by Ret mutants in neuroectodermal cells (Rossel et al., 1997). For instance, the expression of active Ret mutants and their causal function in neuroendocrine tumors, associated with MEN-2 syndromes, are difficult to reconcile with the dramatic differentiating effects observed when the same mutants are overexpressed either in PC12 or in human neuroblastoma cells (Borrello et al., 1995); Califano et al., 1995; Rossel et al., 1997). In PC12 cells, the Ret-induced molecular and morphological changes leading to differentiation are both mediated by Ras-dependent pathways (Califano et al., 2000). The studies of the present inventors using the claimed GFRα4 molecules provided useful new information to this field.

It was generally believed that the serine/threonine kinase Akt-mediated pathway is responsible for most of the neurotrophin-regulated cell survival (for review see Kaplan and Miller, 2000). The evidence for the contribution of Ras/MEK/MAPK pathway to neuronal survival is rather conflicting. While neurotrophins induce a strong and sustained activation of MAPK in sympathetic neurons and PC12 cells, most studies have found that inhibition of MEK has minimal effects on neurotrophin-dependent neuronal survival. The major role for MAPK-induced survival pathways may be to protect neurons from death due to injury or toxicity, rather than from trophic factor withdrawal (Kaplan and Miller, 2000). Recent work of Ashcroft et al., 1999) has shown that while PI-3 kinase can contribute in part to neurite initiation processes, its selective activation and subsequent signalling to downstream effectors such as Akt, functions mainly to promote cell survival in PC12 cells. The Ras/MAPK pathway, on the other hand, is mainly responsible for neurite outgrowth and differentiation (Perron and Bixby, 1999), Ashcroft et al., 1999). Also in this respect the results of the present invention provided new information as regards GFRα4s.

The transforming ability of several viral and cellular oncoproteins depends on their capacity to activate PI3-K.

a) Ret-MEN2A and MEN2B mediate enhanced PI3-K activity and high phosphorylation state of its downstream signalling molecules;

b) Ret-mediated cell-transforming effect is known to be critically dependent on the activation of PI3-K/Akt pathway (Murakami et al., 1999; Segouffin-Cariou and Billaud 2000). In medullary thyroid carcinoma cell line TT, which carries Ret-MEN2A mutation, introduction of v-Ha-ras oncogene or activation of exogenous Raf (a kinase of MEK) leads to TT cell differentiation, a process opposite to oncogenic transformation (Nakagawa, et al., 1987; Carson-Walter, et al., 1998). Also as regards to these articles the present invention provides new useful data.

All members of GDNF family have shown to protect against excitotoxic motor neuron degeneration. In contrast, only GDNF and NRTN but not PSPN are able to induce neurite outgrowth in the organotypic culture of the same motoneuronal population. A specific inhibitor of MAP kinase, PD98059, inhibits the motor axon outgrowth-promoting activity of the GDNF but not the neuroprotective activity. (Ho, et al., 2000). Also as regards neurite outgrowth new data is provided by the present invention.

Because Ret in vivo is never expressed alone but always with a GFRα co-receptor (Golden, J. et al., 1999) it has been suggested that there is a difference in the activation of Ret signalling cascades depending on Ret interaction with one of the GFRα co-receptors. The signalling events might be different also when constitutively activated oncogenic Ret acts alone, without a co-receptor. This difference may lead to the predominance of either differentiating or surviving/proliferating cellular response. The present invention provides information suggesting that the Ras/MAPK pathway, being responsible mostly for cells differentiation in this paradigm, may undermine the action of PI3-K/Akt cascade, which can lead to the oncogenic transformation. The absence or inhibition of Ras/MAPK pathway on top of PI3-K/Akt activation might be causative in the development of Ret-mediated MEN2 cancer syndrome, which is also shown below in the present invention.

The present inventor showed that unlabelled PSPN displaces [$^{125}$I] PSPN from GFRA4-transfected Neuro-2a cells, which express endogenous Ret. PSPN can be specifically cross-linked to mammalian GFRα4 and Ret, and is able to promote autophosphorylation of Ret in GFRA4-transfected cells. PSPN, but not other GDNF family ligands, promotes the survival of cultured sympathetic neurons microinjected with GFRA4 and RET. Three different splice forms of human GFRA4 mRNA encoding for two GPI-linked and one putative soluble isoform identified by the present inventors were expressed exclusively in the thyroid gland. Overlapping expression of RET and GFRA4 but not other GFRA mRNAs in normal and malignant thyroid medullary cells suggests that GFRα4 may restrict the MEN2 syndrome to these cells.

As already described above the present inventors in their preliminary studies identified from a putative mouse the Gfra4 gene localized near the mahogany locus (Gunn et al., 1999) putative exons of the Gfra4 gene homologous with other Gfra receptor genes and identical to several expressed sequence tags (see the Examples). The present inventors used RACE-cloning and RT-PCR of Gfra4 cDNA from various tissues to identify the 5' and 3' sequences and splice variants of mouse Gfra4 mRNA. All 5'RACE clones from the thyroid (including parathyroid) glands contained the signal sequence encoded by exon Ia (FIGS. 1A, 1C).

One 5'RACE clone contained an alternatively spliced exon Ib (FIG. 1C), which would be translated into a weak putative signal sequence. All cDNA clones isolated from brain included a 53 bp intron between exons II and III, and the 5' extended up to 100 bp into the first intron upstream of exon II (FIG. 1C). Translation of these mRNAs gave rise to a protein without a signal sequence (not shown) (FIG. 18, SEQ ID NO:1: and SEQ ID NO:7:).

The predicted amino-acid sequence of full-length mouse GFRα4 from juvenile thyroid gland consisted of 263 aminoacids with a hydrophobic signal and C-terminal sequences typical for a putative GPI-anchored protein (Udenfriend and Kodukula, 1994). Mouse GFRα4 showed higher amino-acid identity with chicken GFRα4 (53%) than with chicken GFRα1 (40%) and GFRα2 (40%). However, the identity between mouse and chicken GFRα4 was lower than the identity between mouse and chicken GFRα1 (80%) or between the mouse and chicken GFRα2 (75%). The alignment of mouse GFRα1, GFRα2, GFRα3 and GFRα4, as well as chicken GFRα4 is shown FIG. 1A.

The sequence of the GPI-anchored isoform of human GFRα4 (FIGS. 21B and 22B, SEQ ID NO:4: or SEQ ID NO:5:) showed 79% amino-acid identity with the mouse GFRα4 (SEQ ID NO:1:). Phylogenetic comparison indicated that the mouse GFRα4 is more closely related to mouse GFRα1 and GFRα2 than to GFRα3 (FIG. 1B). Amino-acid sequence alignment (FIG. 1A) showed that mouse GFRα4 protein is smaller than the other GFRα-receptors. The mouse Gfra4 gene (FIG. 1C) contains at least six exons but it lacks the sequences corresponding to exons 2 and 3 of the other Gfra genes (Angrist, et al., 1998; Baloh, et al., 1998), which encode for the first Cys-rich domain (D1) and the hinge region in the putative GFRα domain structure (Airaksinen et al., 1999). Thus in contrast to other GFRα-receptors including chicken GFRα4 that have three domains, mouse and human GFRα4 has only two Cys-rich domains (FIG. 1D).

Northern blot analysis of Gfra4 expression in different tissues showed high mRNA levels in the developing and mature nervous system, thyroid gland and testis (FIG. 2A). Moderate expression was seen in the adrenal gland and in several embryonic tissues (FIG. 2A and not shown). The size of the major Gfra4 transcripts in testis (approx. 1.2 kb) shorter than in other tissues, such as 1-week-old brain (approx. 1.4 kb). Longer transcripts (approx. 2.5 kb) were also present. (FIG. 2A). Gfra4 mRNA levels were low or not detectable in developing and adult kidney, muscle, spleen, liver, and salivary gland (FIG. 2A and not shown).

RT-PCR was used to analyse Gfra4 expression and to distinguish between the different splice forms in various tissues using primers spanning different exons. Gfra4 mRNA comprising exon Ia was prominently expressed in the thyroid, parathyroid, and pituitary glands, and less in adrenal gland (FIGS. 2B,C). The expression pattern of transcripts containing exon Ib was similar to those containing exon Ia. In testis and brain, in contrast transcripts containing exon Ia or Ib were barely detectable or undetectable, respectively (FIGS. 2B,C). This suggests that other exons encoding the N-terminal part of GFRα4 protein are used in brain and testis.

Of all tissue examined, only thyroid, parathyroid and pituitary glands expressed major subset of Gfra4 transcripts in which the short 53 bp intron separating exons II and III was correctly spliced (FIG. 2B). Splicing of this intron occurred also in the adrenal gland but not in the brain or the testis. Gfra4 transcripts with inclusion of the short 53 bp intron separating exons II and III were present in all tissues examined, including thyroid, pituitary and adrenal glands (FIGS. 2B and 2C). Translation of this intron causes a frame shift and premature stop codon producing a truncated protein with domain-2 (D2, FIG. 1D) followed by a 53 amino-acid hydrophilic tail (SEQ ID NO:15:). This suggests that, regardless of possible signal sequence, testis and brain tissues examined would produce little, if any, membrane anchored GFRα4. These results were confirmed by RNAse protection assay using a probe that spans from exon II to exon IV (see Experimental Methods, data not shown). Translation of the transcripts that contain exon Ia and the intron (a3 and a4 in FIG. 2C) would lead to production of a putative truncated isoform of GFRα4 with 190 amino acids and strong signal sequence (SEQ ID NO:3:). In contrast, possible translation products of Gfra4 transcripts that contain exon Ib and the intron (b3 and b4 in FIG. 2C) might be poorly secreted.

Another alternative splicing event, which was shown to be developmentally regulated, involved the last exon (exon IV). A splice form that encodes the putative GPI-linked receptor was selectively expressed in the thyroid and parathyroid gland of juvenile 3-week-old animals (FIG. 2B, transcripts a1 and b1 in FIG. 2C.) Surprisingly, in newborn and 6-week-old mice, the thyroid and parathyroid glands preferably produced a longer splice form of Gfra4 mRNA with an alternative usage of splice acceptor site in exon IV (FIG. 2B, transcript a2 and b2 in FIG. 2C). This exon IVb would translate into a putative transmembrane (TM) isoform of GFRα4 (SEQ ID NO:2:) with and over 20 amino-acid hydrophobic strech followed by a nine amino acid hydrophobic tail (SEQ ID NO:16:) instead of a putative GPI-anchor signal sequence (SEQ ID NO:17:) encoded by exon VIa. This TM splice variant was also expressed in adrenal and pituitary glands (FIG. 2B). In conclusion, the splicing of Gfra4 gene is both tissue-specific (with splicing of the short intron between exons II and III, and use of the signal sequence exon Ia) and also developmentally regulated (with alternative usage of different 5' splice sites of exon VI).

Splice site sequences of the short 53 bp intron are weak (FIG. 3) with sub-optimal 3' polypyrimidine tract of the intron between exons V and VIa is also non-canonical. Weak splice sites are typically found at alternatively spliced sites, for example, in the calcitonin/CGRP gene that produces calcitonin in thyroid C-cells and CGRP in neuronal tissue. According to one model, additional RNA processing factors that help to recognize weak splicing sequences in calcitonin/GCRP gene are present in the C-cells (Lou and Gagel, 1998). It is possible that the tissue-specific and developmentally regulated splicing of the Gfra4 gene uses these same factors. However, although highly specific alternative splicing factors cannot be ruled out, the evidence found suggested the developmental and tissue specificity may arise from different ratios of general antagonistic and cooperating splicing factors as discussed by Lopez, 1998; Grabowski, 1998.

In situ hybridization was used to study the distribution of Gfra4 and Ret mRNAs in mouse tissues (summarized in Table 1). Gfra was highly expressed in the intermediate lobe of developing (E14, E16 and P0) and mature pituitary gland (FIG. 4A and Table 1), while Ret was expressed in the neurohypophysis and not in the intermediate lobe (FIG. 4B). Moderate levels of Gfra4 transcripts were found in several tissues at different embryonic and postnatal stages examined such as the condensing mesenchyme of developing bones (FIG. 4C) and developing nervous system (Table 1). In adult spinal cord, Gfra4 mRNA was present in most principal neurons including motor neurons (FIG. 4D). In adult brain, Gfra4 was expressed in neurons, with higher levels in the cerebral cortex and hippocampus than in the brainstem and cerebellum (FIG. 4E). This expression pattern was strikingly different from that of Ret (FIG. 4F). Moderate Gfra4 expression was seen in the gut circular muscle and myenteric ganglia (FIGS. 4G,H), as well as in other peripheral ganglia, including the sensory doral root and trigeminal as well as superior cervical and sympathetic chain ganglia (Table 1). In testis, Gfra4 mRNA was expressed in seminiferous tubules (FIGS. 4I and 4J). Gfra4 and Ret were co-expressed in the neural crest-derived ultimobranchial body at E12 (FIGS. 5A-5C), E14, and also E16, when it starts to fuse with the thyroid diverticulum (Table 1).

In newborn mouse, highest expression of Gfra4 was detected in distinct cells in thyroid medulla where calcitonin-producing C-cells are located (FIG. 5D). Hybridization of adjacent sections with Ret probe (FIGS. 5E and 5F) showed a similar pattern to Gfra4. Thus, the thyroid C-cells, which express Ret (Tsuzuki et al., 1995; Belluardo et al., 1999), co-express Gfra4. In contrast, other Gfra (Gfra1-2) mRNAs were not detected in the thyroid C-cells (data not shown) consistent with previous data) (Belluardo, et al., 1999; Golden, et al., 1999).

In postnatal thyroid gland, Gfra4 (FIG. 5G) and Ret (FIGS. 5H and 5I) co-expression continued in the C-cells. Gfra4 mRNA levels remained abundant at least up to 17 weeks while Ret levels appeared to decrease (Table 1). Interestingly, the parathyroid gland, which expressed little if any Gfra4 at birth (FIG. 5D), expressed highly in 3- and 6-week old mice (FIG. 5G and Table 1). However, we could not detect Ret expression in the parathyroid gland by in situ hybridization at any developmental stage examined (FIGS. 5E and 5I as well as and Table 1).

Gfra4 and Ret were also expressed by newborn, postnatal and adult adrenal medulla (FIGS. 5J-5L and Table 1) at P8 while all cells in the medulla appeared to express Gfra4 (FIG. 5J), only a subpopulation of them, presumably chromaffin cells (Nakamura, et al., 1994; Tsuzuki, et al., 1995), contained Ret mRNA (FIG. 5L).

The tissue-specific splicing, leading to putative GFRα4 isoforms with either GPI- or transmembrane anchor, and co-expression of Gfra4 and Ret in embryonic and postnatal thyroid C-cells suggested a physiological role for GFRα4 in the development of these tissues. To test this possibility, we studied the number of C-cells in thyroid glands from Ret-deficient (−/−) mice. The number of calcitonin-immunoreactive cells in E18 Ret −/− mice appeared clearly reduced compared to control (wild-type or heterozygous) littermates (FIGS. 6A and 6B). Counting of immunoreactive profiles from serial reactions throughout the thyroid gland indicated a significant loss of about 37% (control 2540±240, Ret −/−1600±100, n=4 littermate pairs, P<0.005 using t-test). Thus, some thyroid C-cells seem to require Ret-signalling already during embryonic development. The selective expression of Gfra4 in these cells suggests that GFRα4 mediates the Ret-signalling in C-cell development. Other C-cells may require GFRα4/Ret-signalling postnatally, as Gfra4 and Ret are co-expressed in these cells up to adulthood. The adrenal gland has been reported to be unaffected in newborn Ret-deficient mice (Durbec, et al., 1996). However, the expression of Gfra4 and Ret in postnatal adrenal medulla suggests that signalling via GFRα4-Ret receptor complex may be important in postnatal development of adrenal medullary cells. Finally, the expression of Gfra4 and Ret in chromaffin and C-cells suggests that the putative ligand PSPN should have trophic or other biological effects on these cells.

Efficiently spliced Gfra4 transcripts in mouse are expressed in thyroid, parathyroid and adrenal glands, that is, in tissues affected in humans with MEN2 syndromes, suggesting a causal link. GFRA4 is expressed and efficiently spliced also in human thyroid gland. In MEN2 cancer cells, deregulated RNA processing (Lou and Gagel, 1998) could lead to altered expression of Gfra4 mRNA splice forms. GFRα4-receptors may bind and modulate specific Ret mutants and could be essential for their oncogenic activity.

In the present invention the structure and expression patterns of human GFRα4 are described as well as the cloning of human GFRα4 cDNAs encoding three different isoforms of human GFRα4, two GPI-linked and one putative soluble isoform, from adult human thyroid gland. The cloning and expression of various mouse GFRα4 cDNAs encoding different protein isoforms have been described above. As in mouse, all human GFRα4 isoforms lack the first Cys-rich domain (D1) common for all known GFRα-receptors, including chicken GFRα4 (Thompson, et al., 1998).

Of 25 different adult and two fetal tissues studied, GFRA4 transcripts were detected only in the adult thyroid gland. However, it cannot be excluded that GFRA4 could be expressed in other tissues (such as pituitary intermediate lobe, which expresses high levels of Gfra4 in mouse) or at earlier developmental stages (such as developing adrenal medulla) not analyzed here. However, this apparently exclusive expression of human GFRA4 in thyroid suggests a more tissue-specific transcriptional regulation and possibly a more restricted role for GFRα4 in human, than in chicken and rodents, where Gfra4 is expressed in many tissues (Thompson, et al., 1998). For example, the lack of GFRA4 in developing and adult human nervous system does not support a physiological role for PSPN as dopamine or motor neuron survival factor as was initially suggested using rat neurons (Milbrandt, et al., 1998).

Consistent with previous results disclosed by Nakamura, et al., 1994, Lorenzo, et al., 1995; Tsuzuki, et al., 1995) RET mRNA was expressed at variable levels in many adult human tissues, including the thyroid and adrenal glands. According to Milbrandt, et al., 1998 functional spliced PSPN mRNA is not present in humans. However, the present inventors found unspliced transcript of PSPN in all human tissues examined, whereas only low levels of spliced mRNA were detected in human adrenal gland, cerebellum, spinal cord and testis. In contrast, similar levels of both PSPN transcripts are present in most tissues in rat (Milbrandt, et al., 1998; Jaszai, et al., 1998). Although the spliced transcript encoding functional PSPN is expressed in the rat thyroid (not shown), its expression in either adult human (FIG. 10) or postnatal mouse (not shown) thyroid gland could not be detected. Adrenal gland was the only tissue where the spliced PSPN transcript was detected in all three species analyzed (mouse, rat and human). The source of ligand for GFRα4 in human thyroid remains elusive, although secretion of PSPN (from an unknown source) into the blood circulation can be speculated because PSPN triggered Ret autophosphorylation in cells was detected only after serum deprivation (Poteriaev, D., unpublished data). It is also possible that functional PSPN is expressed in the thyroid region at earlier developmental stages not analyzed here.

Masure, et al., 2000 have reported a Gfra4 cDNA encoding a different GFRα4 isoform. It was cloned from rat brain and reported as a GPI-linked receptor for PSPN. However, the signal sequence encoded by the rat Gfra4 cDNA in that report is very weak and differs from the GFRα4 signal sequence disclosed in the present invention.

Sequence information from the preliminary research works using mouse Gfra4 cDNA and gene was used to identify human GFRA4 cDNA and genomic clones which is the main subject of the present invention. First, the genomic region covering putative exon 2 to exon 4 was cloned by PCR from human genomic DNA. Next, the structure of GFRA4 cDNAs and gene were characterized by 5' and 3'RACE of adult human thyroid cDNA and PCR of genomic DNA using primers corresponding to different regions of the putative exons of human GFRA4 as disclosed in the examples above. The sequence of human GFRA4 exon 1 encoding the signal sequence showed high homology to the mouse Gfra4 exon 1a. cDNAs encoding proteins with an alternative signal sequence homologous to the 1b signal sequence found in mouse, or putative transmembrane and soluble isoforms found in mouse, were not identified from human thyroid. Instead, three different alternatively spliced GFRA4 cDNAs were identified (GFRA4a, GFRA4b and GFRA4c, (SEQ ID NO:10), (SEQ ID NO:11) (SEQ ID NO:12), FIG. 9B):

(i) GFRA4a (810 bp) corresponds to the mouse Gfra4 transcript a1. The predicted protein (GFRα4a, 290 amino acids, FIG. 9C) contains a putative N-terminal hydrophobic signal, one N-linked glycosylation site (NVSA) at position 178, and a hydrophobic stretch of amino acids in the C-terminus, preceded by a hydrophilic linker region, consistent with a GPI-anchor signal sequence (Udenfried, et al., 1995). The amino acid identity between mouse and human GFRα4a is 76%, whereas the identity between human and chicken GFRα4 is 54% (covering amino acids 143-340 in chicken GFRα4). The other alternative human GFRα4 transcripts are:

(ii) GFRA4b (900 bp), in which the small intron (79 bp) separating exons 2 and 3 (FIG. 9A) is included in the transcript, and the 3'splice site of exon 4 is located 11 bp upstream of the respective splice site used in the GFRA4a transcript. The small intron between exons 2 and 3 is also inefficiently spliced in majority of mouse tissues. Inclusion of this intron in mouse Gfra4 transcripts with exon 1a or exon 1b leads to putative soluble protein isoform. In contrast, translation of the transcript GFRA4b in human would lead to a GPI-linked protein of 299 amino acids. In this protein isoform, the N- and C-terminal ends are identical to the respective regions of GFRA4a, but the middle region consists of a stretch of 66 amino acids translated in different frame from intron 2 and exon 3. This sequence is not homologous to any protein in public databases.

(iii) GFRA4c (867 bp), in which the introns between exons 2 and 3, and between exons 3 and 4 are included in the transcript. These introns would lead to a frameshift with a stop codon located inside exon 5 and production of a putative soluble isoform of 236 amino acids. It is interesting to note that the sequences of the 3' splice sites of both mouse and human exon 3 and exon 4 contain a short polypyrimidine-tract interrupted with purines, which is characteristic to alternatively spliced exons (Lou, et al., 1994).

The present invention is also related to expression of GFRA4, PSPN and RET in different human tissues. Expression of GFRA4, PSPN and RET was analyzed by RT-PCR in 25 different adult and two fetal tissues (FIG. 10). Expression of GFRA4 was only detected in the adult thyroid gland (FIG. 10) using primers P2 and P3 (see FIG. 9). Similar results were obtained using different combinations of primers (data not shown). The smallest band of 699 bp corresponds to the GFRA4a cDNA where all introns are spliced out, whereas the 789 bp band corresponds to the intron 2-containing GFRA4b transcript. The 863 bp PCR fragment corresponds to the cDNA containing both introns 2 and 3 encoding the putative soluble isoform (GFRA4c, FIG. 9B). The unspliced transcript (approx. 589 bp) of PSPN was expressed in all human tissues examined using primers detecting the full-length PSPN transcript (FIG. 10, row 2). No transcripts were observed when RNA was used as a template for PCR, which shows that the cDNA samples did not contain chromosomal DNA. Low levels of spliced PSPN transcripts (476 bp) encoding the functional protein were present in human adrenal gland, cerebellum, spinal cord and testis, and were not detected in the thyroid gland. RET mRNA was expressed at variable levels in most tissues examined (FIG. 10, row 3).

The present invention is related to activation of human GFRα4/Ret receptor complex, which is unique for PSPN. To study the binding of human PSPN to human GFRα4, we used GFRA4a-transfected mouse neuroblastoma Neuro-2a cells (hGFRα4/Neuro-2a), which endogenously express Ret. These cells strongly bound [$^{125}$I]PSPN, while mock-transfected Neuro-2a cells did not (FIG. 11C). Low concentrations (Approx. 1 nM) of unlabeled PSPN effectively displaced [$^{125}$I]PSPN from the GFRA4-expressing cells, whereas GDNF (up to 300 nM), NRTN (up to 200 nM) and ARTN (up to 200 mM) were ineffective (FIG. 11A). Thus, in the presence of Ret human GFRα4 binds specifically PSPN, but not the other GDNF family ligands. PSPN binds to human GFRα4 with IC50 of 1 nM, and a dissociation constant (KD) of approximately 100 pM (FIG. 11A).

Next we studied the binding of PSPN to GFRA4a-transfected CHO cells, which do not express Ret. Treatment of the cells with [$^{125}$I]PSPN, followed by chemical cross-linking and analysis by SDS-PAGE, resulted in a major band of approx. 46 kDa and minor bands of approx. 62 and 92 kDa (FIG. 11B). The approx. 46 kDa band corresponds a PSPN monomer (approx. 14 kDa) cross-linked to monomeric GFRα4 (30 kDa). The approximately 62 and 92 kDa bands most probably correspond to PSPN dimer cross-linked to GFRα4 monomer and dimer, respectively. Additional 16 and 32 kDa bands represent PSPN monomer and dimer, respectively (FIG. 11B, lane 6). No specific bands were detected from mock-transfected cells (FIG. 11B, lanes 1 and 2). The amount of cell-bound complexes was greatly reduced by adding unlabeled PSPN or by removal of the GPI-anchored proteins by phosphoinositide-specific phospholipase C (PI-PLC) after cross-linking (FIG. 11B, lane 4 and 5). Combination of these two treatments further reduced the yield of cross-linked products to undetectable levels (FIG. 11B, lane 3). Thus, the human GFRα4 protein, encoded by the GFRA4a transcript indeed contains a GPI anchor. Cross-linked complexes of the same sizes were also identified from hGFRα4/Neuro-2a cells (FIG. 1C). In addition, a minor band of about 200 kDa was observed (FIG. 1C) that could be a complex of PSPN/GFRα4 with Ret.

To study the interaction of PSPN with Ret, proteins cross-linked to [$^{125}$I]PSPN in hGFRα4/Neuro-2a cells were precipitated with Ret antibodies (FIG. 11D, lanes 2 and 4). The major cross-linked complexes of approximately 196 and 232 kDa, as well as minor complexes of about 62 and 92 kDa (same size as bands in FIG. 11C), and also of approx. 400 kDa were obtained under reducing conditions (FIG. 11D, lane 2). Under non-reducing conditions, the approx. 400 kDa band was greatly intensified, which indicates the presence of S-S-bound complexes. No cross-linked cell-bound products were detected using parental Neuro-2a cells (FIG. 1D, lanes 1 and 3). The bands of about 196 and 232 kDa correspond to the complexes of PSPN/Ret (186 kDa) and PSPN/GFRα4/Ret (216 kDa), respectively. The components of the complex of about 400 kDa could be a dimer of the 186 kDa PSPN/Ret complex.

To determine whether PSPN binding to human GFRα4 mediates Ret autophosphorylation, hGFRα4/Neuro-2a cells treated with PSPN were used. Gfra1 expressing Neuro-2a cells treated with GDNF served as a positive control. PSPN induced Ret tyrosine autophosphorylation in hGFRα4/Neuro-2a cells, which showed a phosphorylated band of 170 kDa, corresponding to the active form of Ret (FIG. 11E). No phosphorylation of Ret was observed in vector-transfected Neuro-2a cells (FIG. 11E, mock). Stimulation of Ret phosphorylation was dose-dependent starting at 0.1 ng/ml of PSPN (FIG. 11F).

Figure 12:
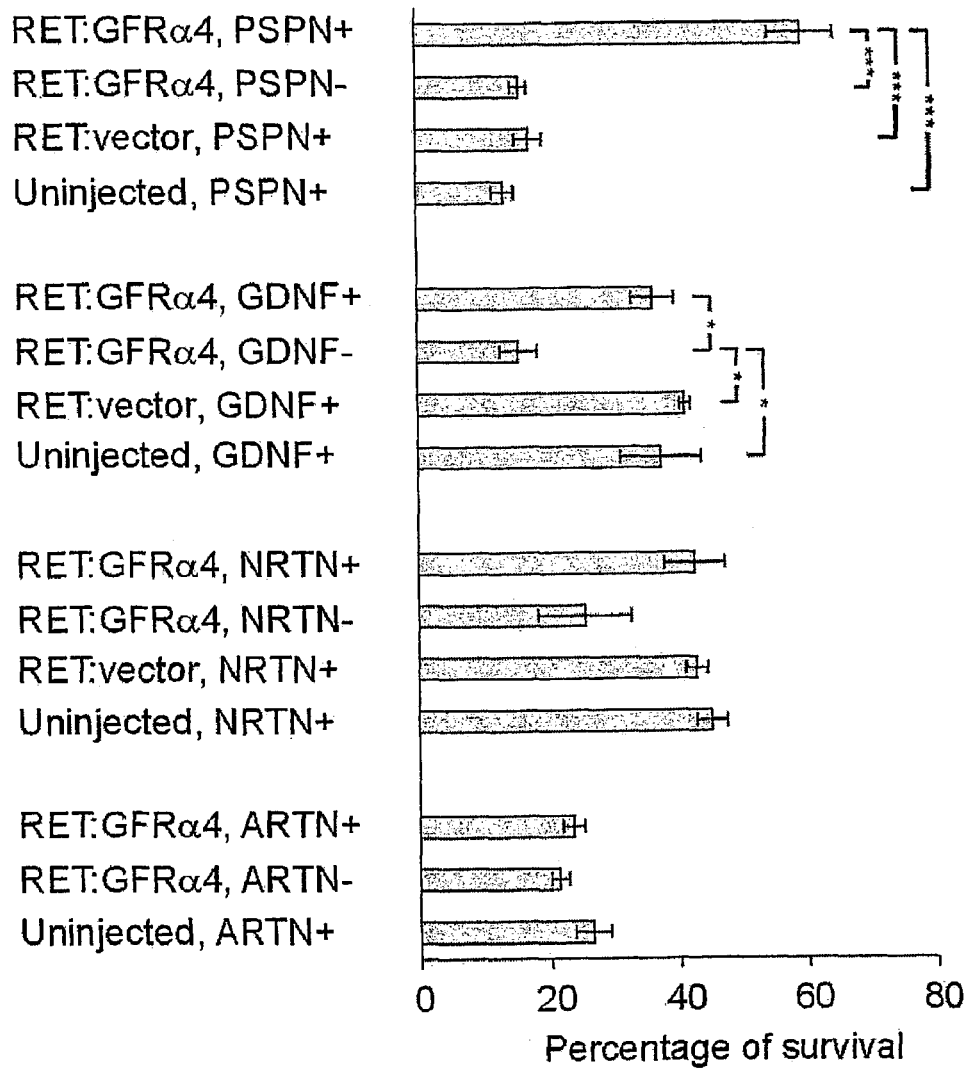

The present invention is related to PSPN which specifically promotes survival of neurons ectopically expressing GFRα4 and RET. In order to study whether binding of PSPN to mammalian GFRα4/Ret complex triggers functional cellular programs, as described for chick GFRα4 (Enokido, et al., 1998). The present inventors expressed the GPI-linked mouse Gfra4 or human GFRA4a together with human RET in neonatal mouse SCG neurons and maintained the neurons further with PSPN for three days. SCG neurons are trophically dependent on NGF, do not express full-length Gfra4 (not shown) and cannot be trophically supported by PSPN (Enokido, et al., 1998; Lindahl, et al., 1999; Milbrandt, et al., 1998). Significant portion of neurons expressing mouse GFRα4 and RET was maintained by PSPN (60% versus 16% without PSPN, p<0.001), whereas omission of GFRα4 abolished this trophic effect (FIG. 12). Similar results were obtained with human GFRA4a (not shown). Also GDNF and NRTN maintained part of neurons expressing RET and Gfra4, but these effects were not reduced by omission of Gfra4 (FIG. 12). Moreover, both factors maintained also uninjected neurons similarly to receptor-injected neurons (FIG. 12). ARTN promoted survival of neither GFRα4/RET injected nor uninjected mouse SCG neurons (FIG. 12). Thus, GFRα4/RET complex requires PSPN, but not other GDNF family members, to activate a survival-promoting program in SCG neurons.

Figure 13:
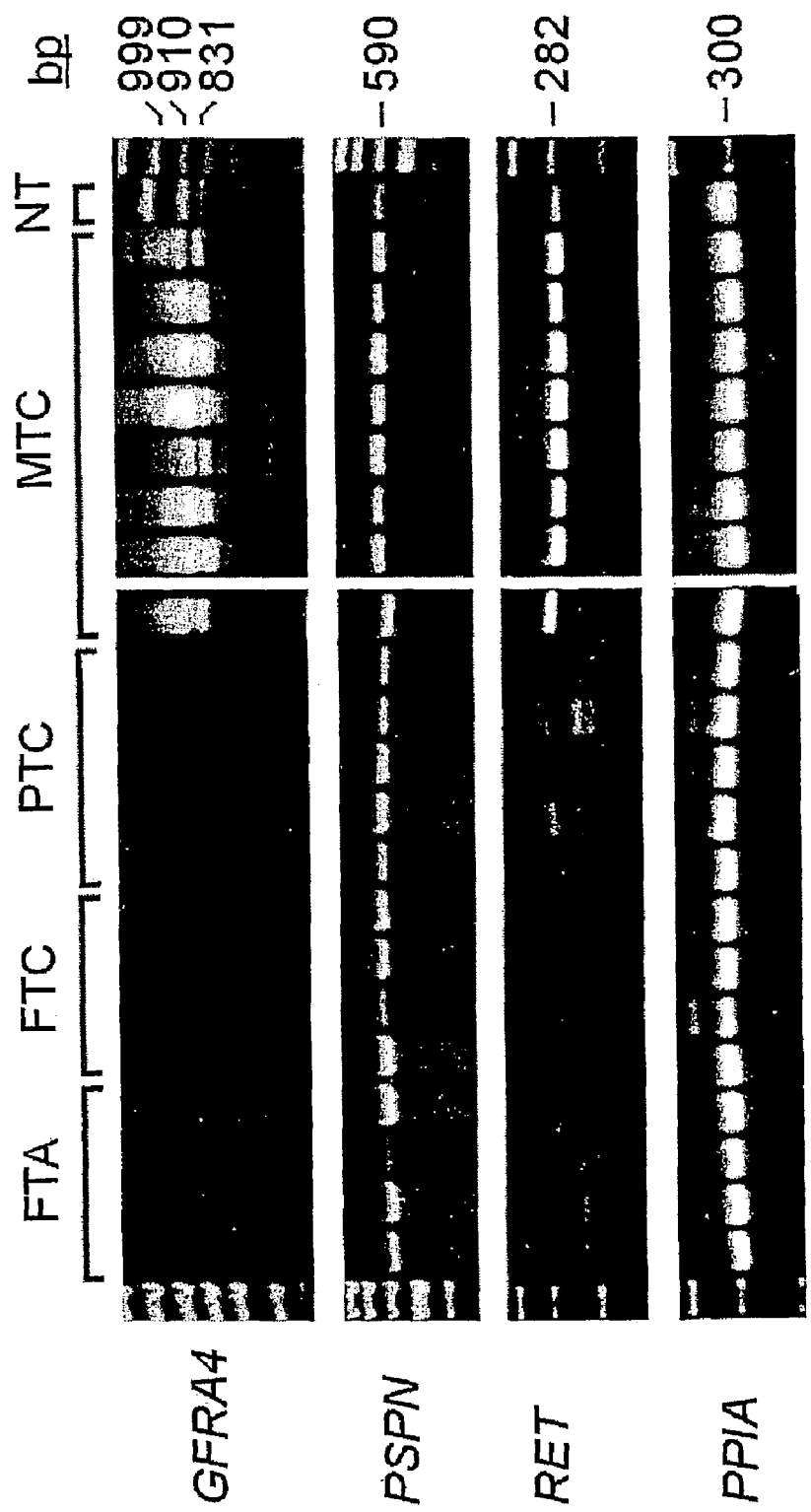
Figure 14:
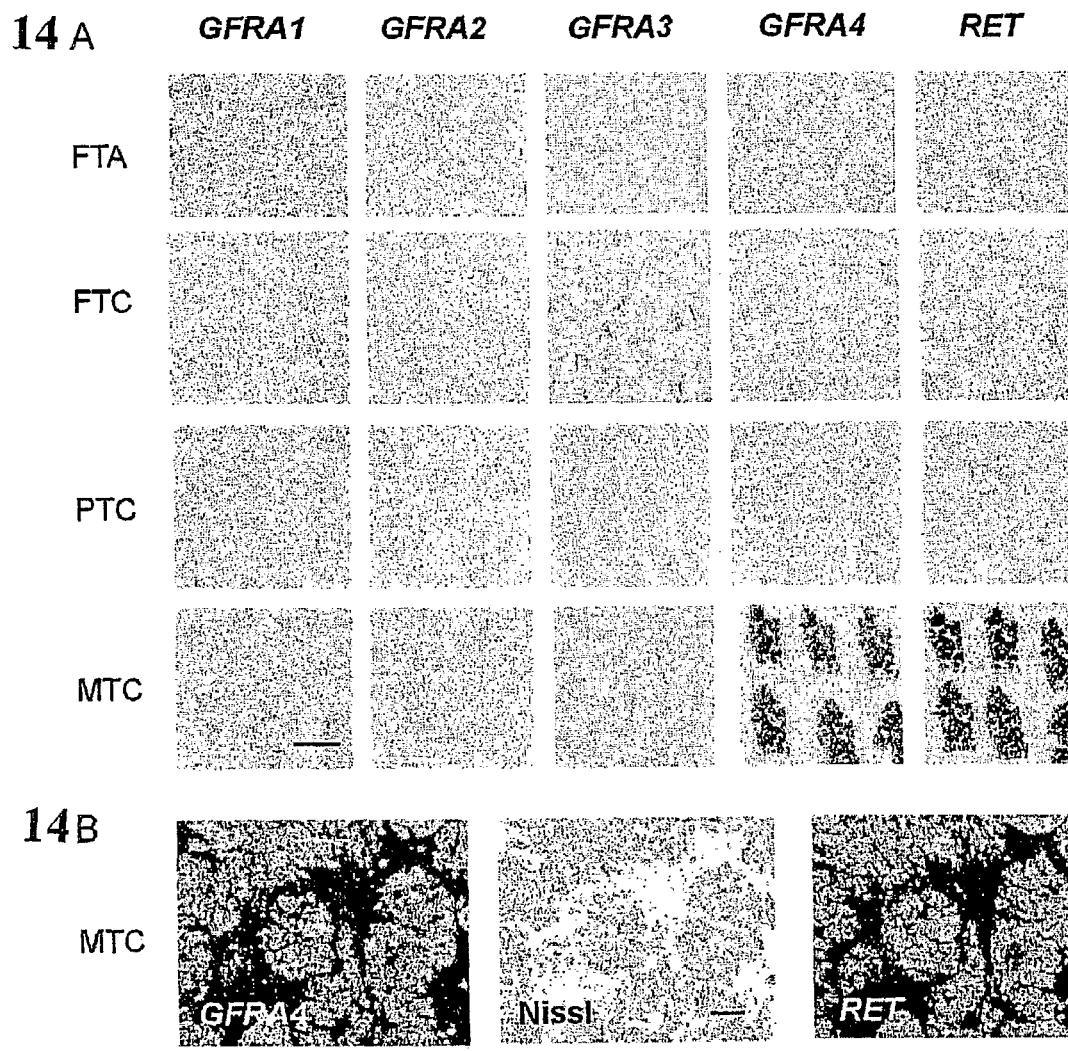

The present invention is related to selective expression of GFRA4 and RET mRNAs solely in medullary thyroid tumours. Co-localization of Gfra4 and Ret in developing and mature mouse thyroid C-cells and their co-expression in adult human thyroid tissue (FIG. 10), prompted us to study the expression of GFRA4, RET and PSPN mRNAs in human primary thyroid tumors. RT-PCR analysis of GFRA4 expression, using primers generating full-length transcript, showed that similar levels of GFRA4 mRNAs encoding the two GPI-linked isoforms and lower levels of transcripts encoding the soluble isoform, are expressed in all eight MTC samples analyzed (FIG. 13, row 1). GFRA4 mRNA was not detected in any of the follicular thyroid adenomas (FTA), follicular thyroid carcinomas (FTC) or papillary thyroid carcinomas (PTC) analyzed. Cellular localization of GFRA4 mRNA was studied by in situ hybridization in the same thyroid tumor samples (FIGS. 14A and 14B). GFRA4 was highly expressed by virtually all the malignant C-cells in the MTC samples analyzed, but not in the accompanying connective tissue and blood vessels. No expression of GFRA4 was detected in the adjacent apparently normal follicle cells found in some samples. Other thyroid tumors, including FTA, FTC and PTC did not express GFRA4. None of the thyroid tumors expressed detectable levels of spliced PSPN mRNA, whereas the unspliced form of PSPN transcript was present in all tumor samples analyzed (FIG. 13, row 2). High levels of RET expression was seen in all MTC tumors (FIG. 13, row 3 and FIG. 14).

Tumor samples were further analyzed for GFRA1, GFRA2 and GFRA3 mRNA expression by RT-PCR and in situ hybridization (FIG. 14A and Table 2). In some tumor samples, low levels of GFRA1, GFRA2 and GFRA3 mRNAs were present in subsets of the tumor cells. To study if GFRA4 gene is mutated in the MTC tumors, full-length GFRA4 cDNA clones from eight MTC samples, the TT cell-line, and normal thyroid were sequenced. Except for a few polymorphisms in the coding region, which do not change the amino acid composition of GFRα4, no mutations were found in the MTC samples or in the TT cell-line. Thus, the coding region of GFRA4 gene is not mutated in MTC tumors.

The present invention is related to a PSPN-GFRα4-Ret complex inducing only the PI3-K/Akt pathway. To test the possible difference between GDNF-GFRα1-Ret and PSPN-GFRα4-Ret signalling mouse neuroblastoma Neuro-2a cell lines stable transfected with either GFRα1 or hGFRα4. Neuro-2a cells express endogenous Ret. Stimulation of Neuro-2a/GFRα1 cells with GDNF lead to the activation of MAP (FIG. 16A) as well as Akt kinases (FIG. 15A). Stimulation of Neuro-2a/hGFRα4 cells with PSPN also lead to the Akt activation (FIG. 15B), however, the level of MAPK phosphorylation remained unchanged (FIG. 16B). This difference between GDNF/GFRα1 and PSPN/hGFRα4 evoked responses appeared also at the physiological level. GDNF and PSPN, acting via their respective co-receptors, both were able to stimulate Neuro-2a cell survival in serum-free conditions (FIG. 17A). In another assay, GDNF but not PSPN was able to induce the neurite outgrowth from the Neuro-2a cells transfected with either GFRα1 or hGFRα4, respectively (FIG. 17B). These results suggest that while GDNF-GFRα1-Ret system activates both Ras/MAPK and PI3-K/Akt cascades, the PSPN-GFRα4-Ret complex can induce only the PI3-K/Akt pathway. PSPN-GFRα4-Ret signalling may be unable to activate the MAPK activity or it may be suppressed during this signalling. Consequently, GFRα1- and GFRα4-specific pathways lead to either mainly differentiation or survival.

In the present invention it was also shown that unlabelled PSPN displaces [$^{125}$I] PSPN from GFRA4-transfected Neuro-2a cells, which express endogenous Ret. PSPN can be specifically cross-linked to mammalian GFRα4 and Ret, and is able to promote autophosphorylation of Ret in GFRA4-transfected cells. Furthermore, it is shown that PSPN, but not other GDNF family ligands, promotes the survival of cultured sympathetic neurons microinjected with GFRA4 and RET.

In the present invention it has further been shown that GFRα4 is the functional receptor for PSPN. The binding and cross-linking studies demonstrated that association of PSPN with the Ret receptor protein tyrosine kinase is mediated by GFRα4. Ligand displacement binding showed that in the presence of Ret, only PSPN but not GDNF, NRTN or ARTN was effective in displacing [$^{125}$I]PSPN from GFRA4-expressing Neuro-2a cells. The dissociation constant (KD) of about 100 pM found here is ten times lower than the KD of about 1 nM reported for mouse PSPN binding to chicken GFRα4 (Enokido, et al., 1998), and 60 times lower than the about 6 nM reported for rat PSPN binding to immobilized rat GFRα4 fusion protein reported by Masure, et al., 2000, but similar to those reported for GFRα1, GFRα2 and GFRα3 and their cognate ligands (Klein, et al., 1997; Trupp, et al., 1998; Baloh, et al., 2000). The lower binding of mammalian PSPN to chicken GFRα4 probably reflects the species difference in GFRα4 structure. PSPN has not yet been characterized from chicken and, if it exists, might differ significantly from the mammalian PSPN.

The cross-linking studies show that PSPN is able to bind GFRα4 also in the absence of Ret. This is consistent with the model that a GDNF family ligand first binds to the corresponding GFRα receptor and subsequently the ligand-GFRα complex binds to Ret (Jing, et al., 1996) However, our results also agree with the alternative model in which the ligand binds a preformed GFRα/Ret complex (Sanicola, et al., 1997). Although PSPN binding to chicken GFRα4 has been shown earlier (Enokido, et al., 1998).

In the present invention it is demonstrated for the first time that the association of PSPN with GFRα4 results in activation of the Ret tyrosine kinase. PSPN treatment of cells expressing GFRα4 rapidly induced Ret autophosphorylation in a dose-dependent manner. PSPN is unable to stimulate Ret autophosphorylation in cells that do not express GFRα4. Thus, the GFRα4a isoform characterized in the present invention is a functional receptor for PSPN in triggering Ret activation. In contrast to this, the rat GFRα4 isoform with a poor signal sequence described by Masure et al., 2000 bound PSPN only as soluble fusion protein and did not lead to Ret activation.

In the present invention it has also been demonstrated that PSPN but not other GDNF family ligands, can promote the survival of cultured SCG neurons ectopically expressing Gfra4 and RET. In our assay, neurons co-expressing RET plus GFRα4 showed an elevated response to GDNF and NRTN but not to ARTN, however, also the uninjected neurons responded to GDNF and NRTN. Therefore, it seems that GDNF and NRTN maintain these neurons via activation of endogenous binding sites and not via GFRα4. Taken together, the binding of PSPN to GFRα4/Ret complex triggers functional cellular responses.

In the present invention the putative role for GFRα4 in medullary thyroid carcinoma is demonstrated. As the RET proto-oncogene plays an important role in the oncogenesis of MTC, a logical step was to examine GFRα4 expression in these tumors. GFRA4 transcripts encoding the two GPI-anchored isoforms were expressed at high level in all MTC samples, whereas no GFRA4 expression was detected in any other type of thyroid tumor analyzed. In addition, moderate levels of GFRA4c encoding the putative soluble form of GFRα4 were found in all MTC samples. Taken together, the data provided by the present inventors suggest that MTC-specific expression of GFRA4 could have diagnostic value.

Strong RET expression was also localized to the malignant C-cells consistent with previous reports (Nakamura, et al., 1994; Santoro, et al., 1990). Low levels of GFRA1, GFRA2 and GFRA3 transcripts were present in subsets of tumor cells, indicating that their expression is not specific to particular thyroid tumor cell type. This result is in line with a recent report showing GFRA1 and GFRA2 expression in some MTC tumor cells (Frisk, et al., 2000). However, our results showing low GFRA1 and GFRA2 expression also in normal thyroid, in other thyroid tumor types, and not in all MTC samples, does not support the idea that GFRα1 or GFRα2 play a role in the primary pathogenesis of MTC. Phenotypic variability within the same MEN2 family or between different families carrying the same mutation in RET suggest that further genetic events or modifier genes are required to induce the tumor phenotype in MTC. The results of the present invention indicate that co-expression of GFRα4 with mutated RET may be necessary for the initial hyperplasia of C-cells occurring in MTC. It should be possible to test this hypothesis by examining whether the development of C-cell hyperplasia and subsequently MTC, pheochromocytoma and ganglion-euromas are suppressed in Gfra4-deficient mice crossed with MEN2 transgenic mice (Smith-Hicks, et al., 2000; Acton, et al., 2000; Laurikainen, et al., 2000).

Further studies with metastases derived from MTC tumors and other endocrine tumors such as GFRα4 expressing pheocromocytomas provide more evidence as regards these questions. Further in vitro studies on cell lines and primary thyroid C-cells should also be informative to reveal the roles for PSPN-signalling via different GFRα4 isoforms through normal and mutant RET.

Similar results were obtained from all thyroid tumours analyzed: GFRA4 was highly expressed in all tumour cells of 6 medullary carcinoma samples but not detectable in cells from other thyroid tumours including tissue samples from 4 follicular adenomas, 4 follicular carcinomas and 5 papillary carcinomas. samples. The six medullary carcinomas analyzed included both sporadic MTC, as well as tumors from patients with inherited MEN2 syndrome (carrying different mutations in RET).

As a conclusion the present invention is related to mammalian, but especially human GFRα4 and GFRα-like molecules and/or compounds interacting with said compounds, where GFRα4 is the ligand-binding subunit required together with RET for PSPN signalling.

The invention provides isolated and purified nucleic acid sequences (e.g. cDNAs) comprising a nucleotide sequence encoding a GFRα4 protein or a fragment thereof. Also described are fragments of said nucleotide sequences, which are suitable as primers or hybridization probes for the detection of GFRα4-encoding nucleic acid sequences (e.g. mRNA). The isolated nucleic acid sequences encode the murine amino acid sequences (SEQ ID NO:1:), (SEQ ID NO:2:) or (SEQ ID NO:3:) and the human amino acid sequences (SEQ ID NO:4:), (SEQ ID NO:5:) or (SEQ ID NO:6:), particularly the murine nucleotide sequences (SEQ ID NO:7), (SEQ ID NO:8:) or (SEQ ID NO:9:) and the human nucleotide sequences (SEQ ID NO:10:), (SEQ ID NO:11:), (SEQ ID NO:12:), (SEQ ID NO:13:).

The isolated nucleic acid sequences of the present invention hybridize under stringent conditions to sequences which are at least about 60%, 65, 70%, 75%, 80%, 85%, 90%, 98% or more homologous to the nucleic acid sequences defined in the claims.

The GFRα4 protein or polypeptide fragments or a biologically active portion thereof can be operatively linked to a non-GFRα4 polypeptide to form a fusion protein.

The isolated and purified nucleic acid sequences encode proteins or fragments thereof including amino acid sequences which are sufficiently homologous to a protein comprising the murine amino acid sequences (SEQ ID NO:1:), (SEQ ID NO:2:) or (SEQ ID NO:3:) as well as the human amino acid sequences (SEQ ID NO:4:), (SEQ ID NO:5:) or (SEQ ID NO:6:) as long as the protein or the fragment thereof maintains the specific GFRα4 activities described above. Preferably, the GFRα4-protein or fragments should maintain the ability to bind to a neurotrophic factor and modulate a cellular response in the way defined in the claims and as described above. The protein encoded by the nucleic acid sequences should be at least about 60%, 65%, 70%, 75%, 80%, 85%, 90%, 98% or more homologous to the murine amino acid sequences (SEQ ID NO:1:), (SEQ ID NO:2:) or (SEQ ID NO:3:) or the human amino acid sequences (SEQ ID NO:4:), (SEQ ID NO:5:) or (SEQ ID NO:6:) or the fragments (SEQ ID NO:14:), (SEQ ID NO:15:), (SEQ ID NO:16:) or (SEQ ID NO:17:).

The protein should preferably be a full length protein which is substantially homologous to the entire murine amino acid sequences (SEQ ID NO:1:), (SEQ ID NO:2:) or (SEQ ID NO:3:) or the entire human amino acid sequences (SEQ ID NO:4:), (SEQ ID NO:5:), (SEQ ID NO:6:) or the fragments (SEQ ID NO:14:), (SEQ ID NO:15:), (SEQ ID NO:16:) or (SEQ ID NO:17:) and includes all naturally occurring full length proteins and allelic variants and splice variants of human or murine GFRα4.

The isolated GFRα4s should preferably comprise amino acid sequences which are at least about 70-80% or more homologous to the murine and human amino acid sequences defined above and should be characterized by at least one but preferably several of the following activities as well as those described in the discussion of the experiments disclosed above:

1) it can interact with (e.g. bind to) a neurotrophic factor.

2) it can interact (e.g. bind to) a tyrosine kinase receptor, e.g., the tyrosine kinase receptor RET;

3) it can modulate the activity of a tyrosine kinase receptor, e.g., the tyrosine kinase receptor RET; and 4) it can bind a neurotrophic factor and modulate a response in endocrine cells, e.g., thyroid C-cells.

The isolated nucleic acid sequence should comprise at least 15-20 nucleotides capable of hybridizing under stringent conditions to a nucleic acid sequence comprising the one of the murine nucleotide sequences (SEQ ID NO:7:), (SEQ ID NO:8:) or (SEQ ID NO:9:) or the human nucleotide sequences (SEQ ID NO:10:), (SEQ ID NO:11:), (SEQ ID NO:12:) or (SEQ ID NO:13:) or parts thereof.

Preferably, the isolated and/or purified nucleic acid sequence corresponds to the naturally occurring nucleic acid sequence. More preferably, the isolated or purified nucleic acid sequences should encode naturally-occurring alleles and splice variants of human GFRα4. Moreover, the GFRα4-encoding murine cDNA sequences (SEQ ID NO:7:), (SEQ ID NO:8:) or (SEQ ID NO:9:) or the human cDNA sequences (SEQ ID NO:10:), (SEQ ID NO:11:) or (SEQ ID NO:12:) or (SEQ ID NO:13:) or cDNA fragments (SEQ ID NO:18:), (SEQ ID NO:19:), (SEQ ID NO:20:), (SEQ ID NO:21:), (SEQ ID NO:22:), (SEQ ID NO:23:), (SEQ ID NO:24:), (SEQ ID NO:25:), (SEQ ID NO:26:), (SEQ ID NO:27:), (SEQ ID NO:28:), (SEQ ID NO:29:), (SEQ ID NO:30:), (SEQ ID NO:31:), (SEQ ID NO:33:), (SEQ ID NO:35:), (SEQ ID NO:37:), (SEQ ID NO:39:), (SEQ ID NO:40:), (SEQ ID NO:41:), (SEQ ID NO:42:), (SEQ ID NO:43:), (SEQ ID NO:44:), (SEQ ID NO:45:), (SEQ ID NO:46:), (SEQ ID NO:47:), (SEQ ID NO:48:), (SEQ ID NO:48:) or (SEQ ID NO:50:), as well as strands which are complementary to the coding strand of the GFRα4 cDNA sequences.

The invention is also related to recombinant transformation or expression vectors or constructs as well as procaryotic or eucaryotic, including mammal host cells comprising one or more of the nucleic acid sequences defined in the claims. Such host cells may be used to produce GFRα4 proteins by culturing the host cell in a suitable medium. If desired, the GFRα4-protein can then be isolated from the host cell.

The invention is also related to transgenic non-human animals in which a GFRα4 gene has been introduced or altered. In such cases the genome of the non-human animal, e.g. a mouse, rat, guinea pig, etc., can be altered by introduction of a nucleic acid sequences of the invention encoding GFRα4 as a transgene. An endogenous GFRα4 gene within the genome of the non-human animal can be altered or made functionally incompetent by homologous recombination or by using the knock-out technique.

The invention is further related to isolated GFRα4 or GFRα4-like molecules or compounds interacting with said molecules, e.g. biologically active fragments thereof. The isolated GFRα4s or fragments can bind to a specific neurotrophic factor and stimulate a response in a neurotrophic factor responsive cell.

The invention also provides preparations or compositions of GFRα4s which comprise amino acid sequences of the GFRα4s defined above in combination with carriers or diluents which can be pharmaceutically acceptable or not depending upon the application.

The GFRα4s of the present invention can be used to prepare anti-GFRα4 antibodies. Accordingly, the invention also provides antigenic peptides of GFRα4. These should preferably comprise at least 8 amino acid residues of the murine or human amino acid sequences defined above and in the claims. These should encompass at least one epitope of GFRα4 against which an antibody may be raised.

The peptide may form a specific immune complex with GFRα4. Preferably, the antigenic peptide comprises at least 10, more preferably 15, at least 20 or more amino acid residues providing a sufficiently high antigenicity index. Thus the present invention provides antibodies which specially bind GFRα4 or GFRα4-like molecules or compounds interacting with said molecules. The antibody is preferably monoclonal, but naturally polyclonal antibodies may be used. The antibody may be coupled to a detectable or recordable substance and it may be incorporated into a pharmaceutical composition comprising the antibody and a pharmaceutically acceptable carrier.

Furthermore, the invention pertains to methods for modulating the GFRα4 mediated cell activity or signalling including cell proliferation and/or differentiation. Such methods include contacting the cell with a compound or agent capable of modulating the activity of a GFRα4 protein or the expression of GFRα4 nucleic acid sequence in such a way that a cell associated activity is measurably altered in relation to the cell associated activity in the absence of the agent. The cell, e.g. a neuron or endocrine cell should be capable or responding to a neurotrophic factor through a specific signalling pathway involving the GFRα-4 protein, as described in the examples.

The agents, which modulate GFRα4 protein can be agonists, which stimulate GFRα4 activity or the expression of the GFRα4 nucleic acid sequences or antagonists, which inhibit GFRα4 protein activity or expression of GFRα4 nucleic acid sequence.

Examples of agents which stimulate GFRα4 protein activity or GFRα4 nucleic acid expression include small molecules and nucleic acid sequences encoding GFRα4 which can be or have been introduced into the cell. Examples of agents which inhibit GFRα4 activity or expression include small molecules, antisense GFRα4 nucleic acid sequences, antibodies specifically binding to GFRα4. The agent is administered to a cell, such as a neuron or an endocrine cell present in the subject.

The present invention also pertains to methods for making diagnoses and/or treating subjects having disorders mediated by abnormal GFRα4 activity and/or expression. For example, the invention pertains to methods for treating a subject having a disorder characterized by aberrant GFRα4 protein activity or nucleic acid expression. Examples of such disorders are neuronal disorders, endocrine system disorders, e.g., multiple endocrine neoplasia type 2 (MEN2) syndrome, disorders associated with abnormal or aberrant cell development, differentiation and function. For example, axonal sprouting in epilepsy due to compensatory neurotrophic factor production after seizures may aggravate the disease process. Augmenting GFRα4 type of signaling in such conditions could be useful by preventing neuronal death without producing aberrant sprouting.

The methods of treatment include administering to the subject GFRα4 or GFRα4-like molecules or compounds interacting (modulators or mimetics) with said molecules in such amounts that treatment of the subject occurs.

The invention also pertains to methods for detecting genetic mutations in a GFRα4 gene, thereby determining if a subject with a mutated gene is at risk of having or is predisposed to have a disorder characterized by aberrant or abnormal GFRα4 nucleic acid expression or GFRα4 activity, such as an endocrine system disorder, rare types of MEN2-like syndromes without Ret mutations or MEN2-like syndromes with additional phenotype, e.g., pituitary tumours. Activity of GFRα4 signalling pathway in endocrine systems can lead to disorders including tumours associated with cellular development of cells of these organs as shown in the present RET invention. For example, axonal sprouting in epilepsy due to compensatory neurotrophic factor production after seizures may aggravate the disease process. Augmenting GFRα4 type of signaling in such conditions could be useful by preventing neuronal death without producing aberrant sprouting.

The methods include detecting, in a sample of cells from the subject, the presence or absence of a genetic mutation characterized by an alteration affecting the integrity of a gene encoding a GFRα4 protein, or the misexpression of the GFRα4 gene.

The invention further pertains to methods for detecting the presence of GFRα4 or fragment thereof, in a biological sample. The methods involve contacting a biological sample, e.g. any (metastatic) tumour sample, with a compound or an agent capable of detecting GFRα4 protein or GFRα4 encoding mRNA in such away that the presence or absence of GFRα4 can be detected in the biological sample. The compound or agent can be, for example, a nucleic acid probe which is or can be labelled and is capable of hybridizing to GFRα4 encoding mRNA or an antibody which is labelled or can be labelled with a suitable detectable marker and is capable of binding to a GFRα4 protein. The invention further provides methods for diagnosing the subject with, for example, an endocrine system disorder or neuron outgrowth disorder based on detection of GFRα4 protein or its mRNA as well as the GFRα4 mediated signalling.

The method involves for example the contacting of a cell, tissue, or fluid sample (e.g., a tumour sample) from the subject with an agent capable of detecting GFRα4 protein or its mRNA and thereafter determining the amount of GFRα4 protein or mRNA expressed in the sample to a control sample and forming a diagnosis based on the amount of GFRα4 protein or mRNA expressed in the sample or its signalling as compared to the control sample. Kits for detecting GFRα4, or fragments thereof by immunoassays or hybridization or microarray techniques from a biological sample are thus also within the scope of the invention.

The present invention also relates to methods, especially, screening assays for identifying compounds or identifying disorders characterized by aberrant GFRα4 nucleic acid expression or protein activity. Activity of GFRα4 signalling pathway in endocrine systems can lead to disorders including tumours associated with cellular development of cells of these organs as shown in the present RET invention. For example, axonal sprouting in epilepsy due to compensatory neurotrophic factor production after seizures may aggravate the disease process. Augmenting GFRα4 type of signaling in such conditions could be useful by preventing neuronal death without producing aberrant sprouting.

These methods typically include assaying the ability of a compound or agent to modulate the expression of the GFRα4 gene or the activity of the GFRα4 mediated signalling and thereby identifying compounds which are useful for treating a disorder characterized by aberrant GFRα4 nucleic acid expression or protein activity. The method involves contacting a biological sample obtained from a subject having the disorder with the compound or agent, determining the amount of GFRα4 protein expressed and/or measuring the activity of the GFRα4 protein in the biological sample, comparing the amount of GFR4 protein expressed in the biological sample and/or the measurable GFR4 biological activity in the cell to that of a control sample. An alteration in the GFRα4 expression or GFRα4 mediated signalling in a cell exposed to a compound or agent in comparison to the control is indicative of a modulation of GFRα4 expression and/or GFRα4 activity.

The invention also pertains to methods for identifying compounds or agents which interacts with (e.g., binds to) or mimics a compound binding to or vice versa a GFRα4 protein. These methods can include the steps of contacting the GFRα4 protein or fragments thereof or alternatively a cell expressing GFRα4 with the compound or agent under conditions which allow binding of the compound to the GFRα4 protein to form a complex. Thereafter, the formation of the complex comprising the GFRα4 protein and the compound having the ability of specifically binding to the GFRα4 protein is measured. The formation of the complex is an indication of the presence of a potentially useful interacting compound. Applicable methods are described in the following patents and patent applications EP 639 584, WO 9638553, U.S. Pat. No. 5,571,506, WO 200018790, WO 9950439, WO 9945930, U.S. Pat. No. 0,630,619 and WO 9906599.

The invention further pertains to methods for identifying a compound or agent which can modulate, stimulate or inhibit the interaction of the GFRα4 protein with a target molecule, such as persephin or other neurotrophic factors and the tyrosine kinase receptor RET or other components of signalling pathways and their complexes. In these methods, the GFRα4 protein is contacted, in the presence of the compound or agent, with the target molecule under conditions which allow binding of the target molecule to the GFRα4 protein to form a complex. An alteration, e.g., an increase or decrease, in complex formation between the GFRα4 protein and the target molecule as compared to the amount of the complex formed in the absence of the compound or agent is indicative of the ability of the compound or agent to modulate the interaction of the GFRα4 protein with a target molecule.

The invention is also related to substances capable of specifically recognizing the GFRα4 polypeptides defined in above and in the claims. Such substances are for example antibodies, including polyclonal, monoclonal antibodies produced by recombinant DNA techniques or hybridoma techniques as well as ligands capable of binding specifically to the mammalian GFRα4-receptor. Fragments of antibodies and receptors are also useful as specifically binding substances.

The present invention also enables the production of transgenic non-human animal lacking a functional GFRα4 receptor and which is useful as a test animal obtainable from a genetically modified compatible cell-line (clone) containing a genomic gene coding for a functional GFRα4 receptor, which genomic gene may be functionally inactivated or conditionally inactivatable. Said transgenic non-human animal is useful as a test animal or model for studying GFRα4-mediated signalling in neuronal cells, endocrine cells, especially in thyroid calcitonin-producing C-cells, parathyroid gland cells, adrenal chromaffin cells, cells of pituitary intermediate lobe, nervous system and testis, neoplasia, endocrine tumours, medullary thyroid carcinoma, pheochromocytoma and parathyroid hyperplasia and for diagnosing and/or treating osteoporosis, endocrine tumours, cancer in parathyroid gland cells, adrenal chromaffin cells, cells of pituitary intermediate lobe, neoplasia, endocrine tumours, medullary thyroid carcinoma, pheochromocytoma and parathyroid hyperplasia. Activity of GFRα4 signalling pathway in endocrine systems can lead to disorders including tumours associated with cellular development of cells of these organs as shown in the present RET invention. For example, axonal sprouting in epilepsy due to compensatory neurotrophic factor production after seizures may aggravate the disease process. Augmenting GFRα4 type of signalling in such conditions could be useful by preventing neuronal death without producing aberrant sprouting.

The present invention also provides a method for obtaining a cell-line (clone) useful in the production of the transgenic non-human animal characterized by having the genomic gene encoding a functional GFRα4 receptor inactivated by introducing into stem cells a nucleic acid sequence, which is capable of integrating to said genomic Gfra4 gene and by said integration functionally inactivating said genomic gene or making it conditionally inactivatable.

The cell-line (clone) lacking a functional GFRα4 receptor is obtainable by established gene targeting methods, by:

(a) providing a nucleic acid sequence defined in the claims, which sequence is capable of being integrated into the genomic gene coding for a functional GFRα4 receptor;

(b) preparing a targeting construct by combining the nucleic acid sequence according to step (a), with a selectable nucleic acid sequence acting as a marker which is capable of functionally inactivating and by said integration functionally inactivating the genomic gene or making it conditionally inactivatable;

(c) introducing the targeting construct or vector of step (b) into stem cells or cell lines (clones) of the selected animal;

(d) selecting a cell line (clone) containing the nucleic acid sequence or part thereof according to step (a) which has been integrated into the genomic gene of said stem cell or cell line (clone) using a probe, which is capable of recognizing the selectable nucleic acid sequence acting as a marker.

A cell line (clone) obtained by the method described above is lacking a functional GFRα4 receptor and produces consequently altered levels of GFRα4. The cell lines (clones) of the present invention are useful not only for producing a transgenic non-human animal but also for studying the effect of different compounds, e.g. obtained by combinatorial chemistry, on GFRα4-mediated signalling in neurons, endocrine cells, especially in thyroid calcitonin-producing C-cells, parathyroid gland cells, adrenal chromaffin cells, cells of pituitary intermediate lobe, nervous system and testis, neoplasia, endocrine tumours, medullary thyroid carcinoma, pheochromocytoma and parathyroid hyperplasia and for diagnosing and/or treating osteoporosis, endocrine tumours, cancer in parathyroid gland cells, adrenal chromaffin cells, cells of pituitary intermediate lobe, neoplasia, endocrine tumours, medullary thyroid carcinoma, pheochromocytoma and parathyroid hyperplasia.

The invention is described in more detail in the following examples which are intended to illustrate the invention not to limit its scope.

EXAMPLE 1

Sequence Analysis

Several putative exon sequences homologous to known Gfra genes were identified by BLAST analysis of a 47887 bp sequence containing the putative mouse Gfra4 locus (Gunn et al., 1999) (Genebank accession number AF155960). Database search using these sequences as query detected three mouse expressed sequence tags (ESTs) matching the 3' end of the putative Gfra4 gene (AA823200 or AI1553571, a spliced EST from mammary gland; AU035938, an unspliced one from the brain; and AI845209 a short one from the spinal cord). Nucleotide and amino acid sequence comparisons (BestFit), alignment (PileUp), and phylogenetic tree (GrowTree), as well as signal sequence and transmembrane hydrophobicity plots (PeptideStructure) were analyzed using the SeqWeb program package (Genetics Computer Group, Inc.).

EXAMPLE 2

RACE Cloning cDNA clones representing the 5'-region of Gfra4 transcript were isolated from adult mouse brain, testis and thyroid gland, as well as from E17 embryo, using the 5'-RACE System (Life Technologies) and the GC-RICH PCR kit (Roche) according to the manufacturer's instructions. Total RNA was extracted with Trizol reagent (Life Technologies). The antisense Gfra4 specific primers used in 5' RACE were: 5'-TTC AGC TCA GTG AGC AGT CAT CG-3' (SEQ ID NO:18:) and second nested primer 5'-CAG GTT GTC CAG GTA GTT GG-3' (SEQ ID NO:19:) or 5'-CAT CGT GCC ACG TAC TCA GA-3' (SEQ ID NO:20:). The 3' region of the Gfra4 was cloned with 3'RACE method using Clontech Marathon Ready cDNA from E15 mouse embryos according to the manufacturer's instructions. The primers used in 3'-RACE were: 5'-TAC AAG CCT TTG ACA GCT TGC AGC-3' (SEQ ID NO:21:) and a nested one 5'-AGA GCT GGA GGC AGA AAC AGT CC-3' (SEQ ID NO:22:).

Human GFRA4 cDNAs were identified from a human thyroid cDNA (Clontech Marathon Ready cDNA) by 3' and 5' RACE method using the GC-rich PCR kit (Roche) according to the manufacturer's instructions. Reverse transcription reactions were performed using Superscript II (Life Technologies). PCR systems were GC-RICH PCR kit (Roche) for GFRA4 and PSPN, Expand Long Template PCR system (Roche) for GFRA1, GFRA2, GFRA3 and RET and Dynazyme II (Finnzymes) for PPIA (alias cyclophilin). PCR was run 40 cycles for GFRA4, 35 cycles for PSPN, GFRA1 and GFRA2, and 30 cycles for GFRA3, RET and PPIA using annealing temperatures of 55-60 (C. Full-length human GFRA4 cDNA was obtained using Expand High Fidelity system PCR enzyme (Roche) together with GC-RICH PCR system buffers (Roche). PCR products were cloned into mammalian expression vector pCR3.1 (Invitrogen).

EXAMPLE 3

Northern Blot and Reverse Transcription (RT)-PCR

Norther blot analysis of Gfra4 expression was carried out from total RNA essentially as described (Rossi et al., 1999). Analysis of the splicing pattern of Gfra4 was performed by RT-PCR using Superscript II (Life Technologies) for RT and the GC-RICH PCR kit (Roche) for PCR. The following primers were used (see FIG. 2C): P1, 5'-CCA CCA TGG CCC ACT GCA TGG AGTC-3' (SEQ ID NO:23:); P2, 5'-CCA CCA TGT TGA GAA GAG CA-3' (SEQ ID NO:24:); P3, 5'-GTG TAC AGC AGA CGA GCG GT-'3' (SEQ ID NO:25:); P5, 5'-ATA CAA GCC TTT GAC AGC TTG C-3' (SEQ ID NO:26:); and reverse primers P4, 5'-GTT CCT TGT AAA GAG CTT GCG-3' (SEQ ID NO:27:); and P6, 5'-TGG ACA AGA TGC CTA CTG ACG-3' (SEQ ID NO:28:). The amounts of total RNA was run 35-40 cycles using annealing temperatures of 55-58° C. All the PCR products of different length were sequenced to verify their identity.

EXAMPLE 4

RNAse Protection Analysis

RNAse protection assays were performed as described (Timmusk et al., 1993) using the RPAII kit of Ambion according to manufacturer's instructions. The template for Gfra4 specific cRNA probe was a 550 bp PCR fragment generated using primers P3 and P4. It yielded a fully protected fragment corresponding to Gfra4 mRNA that have spliced both introns between exons II and IV, as well as 235 bp and 315 bp fragment corresponding to Gfra4 mRNA that is unspliced between exons II and III.

EXAMPLE 5

In Situ Hybridization

In situ hybridizations for Ret, Gfra1 and Gfra2 was performed as described Rossi et al., 1999). A mouse full-length Gfra3 cDNA (AF051766) and a bp cDNA fragment of the 3'-end of the mouse Gfra4 was used as template for sense and anti-sense RNA probes. Control sections hybridized with sense probe did not show labeling above background (not shown).

In situ hybridizations for RET, GFRA1, GFRA2, GFRA3 and GFRA4 were performed principally in the same way as described above on cryosections of the same thyroid tumor samples analyzed by RT-PCR. A 206 bp cDNA fragment of the 5'-end of human GFRA4 was used as template for sense and antisense RNA probes. PCR fragments of GFRA1, GFRA2, GFRA3 and RET generated with the same primers as in RT-PCR were cloned and sequenced and used as templates for antisense and sense RNA probes. Control sections hybridized with sense probe did not show labeling above background (not shown). Dark-field and corresponding bright-field images of Nissl counter-stained sections were digitized and processed using Adobe PhotoShop software.

EXAMPLE 6

Immunohistochemistry

Ret-deficient (−/−) and control littermate mice were genotyped as described (Durbec et al., 1996). Anesthetized day E18 embryos were perfused transcardially with 41 paraformaldehyde in PBS, postfixed for 2 hours and cryoprotected overnight in 25% sucrose. Horizontal cryosections of the thyroid gland, serially sectioned at 15 µm, were stained and analyzed by standard immunofluorescence techniques. DAPI (Sigma) was included in embedding medium to stain the cell nuclei. The primary goat polyclonal antibody against calcitonin (sc-7784) was from Santa Cruz Biotechnology. All immunopositive profiles with a clear nucleus were counted in every section through the thyroid glands. The mean nuclear diameter of the C-cells was similar (<1% difference) between the Ret −/− and control groups (not shown). Raw profile numbers per animal without correction are given as mean ±S.D.

EXAMPLE 7

RNA Isolation

RNA from different human tissues was purchased from Clontech (Human Total RNA Panel I-V). Total RNA from frozen human thyroid tissue was isolated using Ultraspec™-II RNA isolation system (Biotecx Laboratories, Inc.). Total RNA from the TT cell-line (ATCC#CRL1803) was isolated with Trizol reagent (Life Technologies). The RET mutation of five MTC patients had been analyzed: one from a MEN2A family member contained the germline C634R mutation, one patient was positive for the M918T but the germline situation was unknown, and three were sporadic MTCs of which one was positive for the M918T mutation.

EXAMPLE 8

RT-PCR

The antisense primers used in 5'RACE were mouse specific Gfra4 primer 5'-CAC GTT GTC CAG GTA GTT GG-3' (SEQ ID NO:41:) and a second human specific GFRA4 nested primer 5'-GCA CTG CGC CAC ATA CTC GGA-3' (SEQ ID NO:42:). The 3'region of GFRA4 was cloned in two steps, first using a GFRA4 specific sense primer P2 (see FIG. 1A) 5'-GCT CCG AGT ATG TGG CGC AGT-3' (SEQ ID NO:43:) and a nested primer 5'-GCT CAC CCA CGC ACT GCT CTT CTG-3' (SEQ ID NO:44:). The 3'region containing the stop codon and 3'UTR sequence was cloned using a sense primer 5'-CCT AAC TAC GTG GAC AAC GTG AGC-3' (SEQ ID NO:45:) and a second nested primer 5'-ATG TGG CCA TTC AGG CCT TTG CCA G-3' (SEQ ID NO:46:) or 5'-GCA GGT GTC CTC CAC AGG CAG-3' (SEQ ID NO:47:). RT-PCR of genomic human DNA was used to locate the intronic nucleotide sequences between exons 4 and 5, and between exons 5 and 6, using a sense primer 5'-CCT AAC TAC GTG GAC AAC GTG AGC-3' (SEQ ID NO:45:) and an antisense primer 5'-GAA GTA TGG AGA GCA GGG AGC GTC-3' (SEQ ID NO:48:). Full-length human GFRA4 cDNAs were obtained using a sense primer P1 (see FIG. 9A); 5'-CCA CCA TGG TCC GCT GCC TGG-3' (SEQ ID NO:49:) and an antisense primer P3; 5'-GAG GTC GCT GTC CTA ATC AGA G-3' (SEQ ID NO:50:).

Primers used in RT-PCR for human, mouse and rat PSPN were as described in (Milbrandt, et al., 1998). Primers used in RT-PCR for human GFRA1 flanked nucleotides 491-870 of GenBank sequence AF042080, GFRA2 flanked nucleotides 148-427 of GenBank sequence U93703, GFRA3 flanked nucleotides 574-1203 of GenBank sequence NM001496 and RET flanked nucleotides 833-1114 of GenBank sequence X12949. The amounts of total RNA in samples were normalized by amplification of a PPIA fragment.

EXAMPLE 9

$^{125}$I-Labelled PSPN Binding

Murine neuroblastoma Neuro-2a cells were transfected (FuGene6, Roche) with full-length GFRA4a cDNA in pCR3.1 vector (Invitrogen), and bulk-selected with 400 (g/ml of G418. PSPN was enzymatically iodinated by lactoperoxidase, up to a specific activity of 100.000 cpm/ng. Binding assays were performed essentially as described (Laurikainen, et al., 2000) with 0.9 nM [$^{125}$I] PSPN in binding buffer (DMEM containing 0.2% BSA and 15 mM Hepes, pH 7.5) for 4 hrs on ice, either in the presence or absence of different concentrations of unlabeled human PSPN (PeproTech EC Ltd.), rat GDNF (Cephalon, Inc.), human NRTN (PeproTech EC Ltd.) or human ARTN (a gift from Drs. J. Milbrandt and E. M. Johnson, Jr.). The amount of [$^{125}$I]PSPN bound to mock-transfected cells was at the background level. KD was calculated using Cheng-Prusoff equation (McGonigle, et al., 1994).

EXAMPLE 10

Chemical Cross-Linking and Immunoprecipitation

CHO cells were transfected (FuGene 6) with full-length human GFRA4a cDNA, grown for two days, washed and incubated with 0.9 nM [$^{125}$I]PSPN in binding buffer (see above) on ice for 4 hrs. After washing the cells were incubated with 1 mM Bis suberate (Pierce) in PBS at RT for 25 min. Following washes, some samples were treated with 0.5 U/ml of PI-PLC (Sigma) at +37° C. for 30 min. Cells were lysed in Laemmli buffer containing β-mercaptoethanol.

The cross-linking reaction for human GFRA4a and mock transfected (pcDNA3; Invitrogen) Neuro-2a cells was done as described above but the cells were lysed in NP-40 lysis buffer (1×Tris-borate saline, 2 mM EDTA, 1% Nonidet P-40, 1% Triton X-100, 1 mM PMSF, Complete™ protease inhibitor cocktail, Roche), clarified by centrifugation at 14 000 rpm for 20 min., immunoprecipitated with 1 (g/ml of Ret antibodies (Santa Cruz Biotechnology) and collected with Protein A Sepharose. The immunocomplexes were washed with NP-40 buffer, and separated by 7.5% SDS-PAGE.

EXAMPLE 11

Ret Phosphorylation Assay

Semiconfluent human GFRA4a-, rat Gfra1- or vector-expressing Neuro-2a cells were maintained with 0.5% serum for 24 hr and then in serum free medium for 4 hr prior to stimulation. After stimulation with PSPN (0.01-100 ng/ml) or GDNF (100 ng/ml), cells were lysed and precipitated with agarose-conjugated anti-phosphotyrosine antibodies (4G10, Upstate Biotechnology) overnight at +4° C. on ice. The membranes were probed with 60 ng/ml anti-Ret antibodies (Santa Cruz).

EXAMPLE 12

Neuronal Microinjections

Postnatal day 1-2 superior cervical ganglion (SCG) neurons were grown 5-6 days on polyornithine-laminin-coated dishes with NGF (30 ng/ml). 50:50 ng/µl cDNA mixtures of short isoform of human RET (gift from Dr. M. Billaud) and either mouse Gfra4a1 (in pcDNA3, Invitrogen) or human GFRA4a (in pCR3.1, not shown) or empty pcDNA3 vector, were pressure-microinjected into nuclei. To find successfully injected neurons later, a plasmid encoding green fluorescent protein (10 ng/µl) was included in every injection mixture. Neurons were grown overnight with NGF and thereafter in NGF-free medium containing blocking anti-NGF antibodies (Boehringer-Mannheim) and PSPN, GDNF, NRTN or ARTN, all at 100 ng/ml. Number of living fluorescent neurons or uninjected control neurons was then counted (initial neurons). 30-80 initial neurons were successfully injected for every treatment group. Healthy fluorescent neurons with intact nuclei and phase-bright cytoplasm were counted 70-75 h later and expressed as percent of initial neurons. Experiments were repeated on independent cultures: n=7 for PSPN, n=4 for GDNF and NRTN, n=3 for ARTN. Significance of the differences between means was estimated by one-way ANOVA followed by Tuckey's post-hoc test at the significance level of α=0.05.

EXAMPLE 13

Analyzing Changes in Phosphorylation Status

To analyze changes in the phosphorylation status of MAPK (ERK1 and ERK2) and Akt (PKB) in Neuro-2a cell lines stable transfected with either hGFRα4, GFRα1 or empty vector, the semiconfluent cells were kept for 18 hrs in the culture medium containing 0.5% fetal calf serum and then were starved for 3 hours in serum-free medium. After stimulation with GDNF or PSPN, the cells were briefly washed with PBS containing sodium vanadate and sodium fluoride and lysed in NP-40 lysis buffer (Tris-buffered saline; 2 mM EDTA; 1% NP-40; 1% Triton X-100; 1 mM PMSF; 1 mM $Na_3VO_4$; 25 mM NaF; Complete™ protease inhibitors cocktail (Boehringer Mannheim). The proteins were separated by 10% SDS-polyacrylamide gel electrophoresis and transferred to Hybond ECL (Amersham) membrane. Immunoblotting was carried out using either MAPK (ERK1/2) Anti-Active™ (Promega) or anti-Akt antibodies (New England Biolabs) recognizing phosphorylated forms of the kinases, and detected with ECL system (Amersham). The blots were then reprobed with MAPK or Akt phosphorylation-independent antibodies.

EXAMPLE 14

Neurite Outgrowth Assay

To assay neurite outgrowth, cells were plated at 0.5 $10^5$ cells/$cm^2$ and maintained in RPMI-1640 containing 1 fetal calf serum supplemented with or without 100 ng/ml either GDNF or PSPN. After 72 hours the percentage of cells with neurites (i.e. bearing processes longer than cell body diameter) was determined. To assay cell survival, cells were washed with serum-free medium, detached and plated in 24-well tissue culture dishes (at approximately 0.5 $10^5$ cells/$cm^2$) containing serum-free medium supplemented with either GDNF or PSPN at different concentrations. Cell viability was determined at day 3 after plating, using Trypan Blue dye exclusion method.

The results of the experiments carried out during the studies are disclosed in more detail below.

THE DESCRIPTION OF THE DRAWINGS

FIG. 1. Sequence of the predicted GPI-linked mouse GFRα4 protein (SEQ ID NO: 1) and structure of mouse Gfra4 gene.

FIG. 1A. Alignment of mouse GFRα1 (SEQ ID NO: 51), GFRα2 (SEQ ID NO: 52), GFRα3 (SEQ ID NO: 53), and GFRα4 (SEQ ID NO: 1) and chicken GFRα4 (SEQ ID NO: 54) amino-acid sequences. Predicted signal sequences are underlined. Cysteines are highlighted. The sequence was divided between the predicted hinge regions into four parts and the two cysteines in the homologous Cys-rich domains (D1-D3, see FIG. 1D) were aligned manually. The last two amino-acids coded by exons II and exon V are marked by asterisk.

FIG. 1B. Phylogenetic tree of the GFRα family. Comparisons were made by using the protein encoding region of mouse Gfra1-Gfra4 cDNAs.

FIG. 1C. Structure of mouse Gfra4 gene (upper) as compared to mouse Gfra2 gene (lower) that has alternatively spliced exons 2 and 3 (Baloh et al., 1998). The structures of mouse Gfra3 (Baloh et al., 1998) and human GFRA1 genes (Angrist et al., 1998) are similar to the mouse Gfra2 gene, except for an additional short exon that encodes for hinge region in GFRA1 and lack of exon 8 in Gfra3. The intron separating exons II and III is very short (53 bp) in Gfra4 as compared to this intron in other Gfra genes (>2 kb). Exon grey shades refer to the homologous Cys-rich domains (D1-D3) and hinge regions in the domain model. N- and C-terminal signal sequences are lined. The lengths of the 5' UTR sequences of exons Ia and Ib (broken line) were not determined.

FIG. 1D. Proposed domain structure of mouse GFRα4 (left) and GFRα2 receptor (right) (Airaksinen et al., 1999). Mouse GFRα4 lacks the first domain (D1), which is present in other GFRα-receptors. Putative N-glycosylation sites are also indicated. (>-)

FIG. 2. Expressions and developmentally regulated tissue-specific splicing of Gfra4 gene.

FIG. 2A. Northern blot analysis of Gfra4 expression in various mouse tissues (upper). The major transcript in testis appears smaller (appr. 1.4 kb). Longer transcripts (appr. 1.6 kb and 2.5 kb) are also seen. Rehybridization with GAPDH probe (below) demonstrates equal loding.

FIG. 2B. Semiquantitative RT-PCR analysis of Gfra4 transcripts from various tissues and postnatal stages. Locations of PCR primers are indicated on the right and shown in FIG. 2C. Upper panel: Transcripts containing exon Ia and the spliced intron between exons II and III (Ia/Δi 703 bp) are produced in adrenal, pituitary and thyroid glands but not in brain or testis. $2^{nd}$ upper panel: mRNAs containing exon Ib (Ib/Δi 676 bp) show a expression pattern similar to those containing exon Ia. Middle panel: The short intron between exons II and III is efficiently spliced (Δi 550 bp) in thyroid and pituitary glands but not (i 603 bp) in brain and testis. $2^{nd}$ lower panel: 3-week-old thyroid glands express the shorter (GPI, 315 bp) splice form, whereas newborn and 6-week-old thyroid glands, preferably as well as postnatal adrenal and pituitary glands, produce the longer (TM 380 bp) splice form. Note that the testis and brain also express their TM or GPI splice forms, but protein synthesis would produce a putative soluble form due to intron inclusion. Lower panel: The lines contain similar levels of control Ppian transcript.

FIG. 2C. Structures of different Gfra4 mRNA splice forms containing exon Ia (a1-a4) and exon Ib (b1-b4). Primers P1-P6 used in FIG. 2B are indicated below the gene structure. Asterisks denote stop codons. The exon colours are the same as in FIGS. 1C and 1D. Transcript a1 (SEQ ID NO:7:) is predicted to encode for, the GPI-linked isoform of GFRα4 (SEQ ID NO:7:), whereas a2 (SEQ ID NO:8:) encodes for a putative trans-membrane (TM)-anchored receptor (SEQ ID NO:2:). Transcripts a3 and a4 (SEQ ID NO:9:) encode for truncated and secreted molecule (domain-2 only) (SEQ ID NO:3:). Transcripts b1-b4 are similar to the transcripts a1-a4 except for usage of exon Ib, which encodes for a putative weak N-terminal signal sequence instead of exon Ia. Shown in FIGS. 2A and 2B are representative results from one of three independent experiments. Abbreviations: ad, adult; pit, pituitary gland.

FIG. 3. Intron-exon junctions (SEQ ID NOS 55-62, respectively in order of appearance) in the coding region of mouse Gfra4 gene. Consensus splicing sequences are indicated (upper line) (SEQ ID NO: 55). There are more non-canonical nucleotides (marked in bold) in the splicing signals of the alternatively spliced introns. Splice acceptor and donor sites are shaded.

Figure 4:
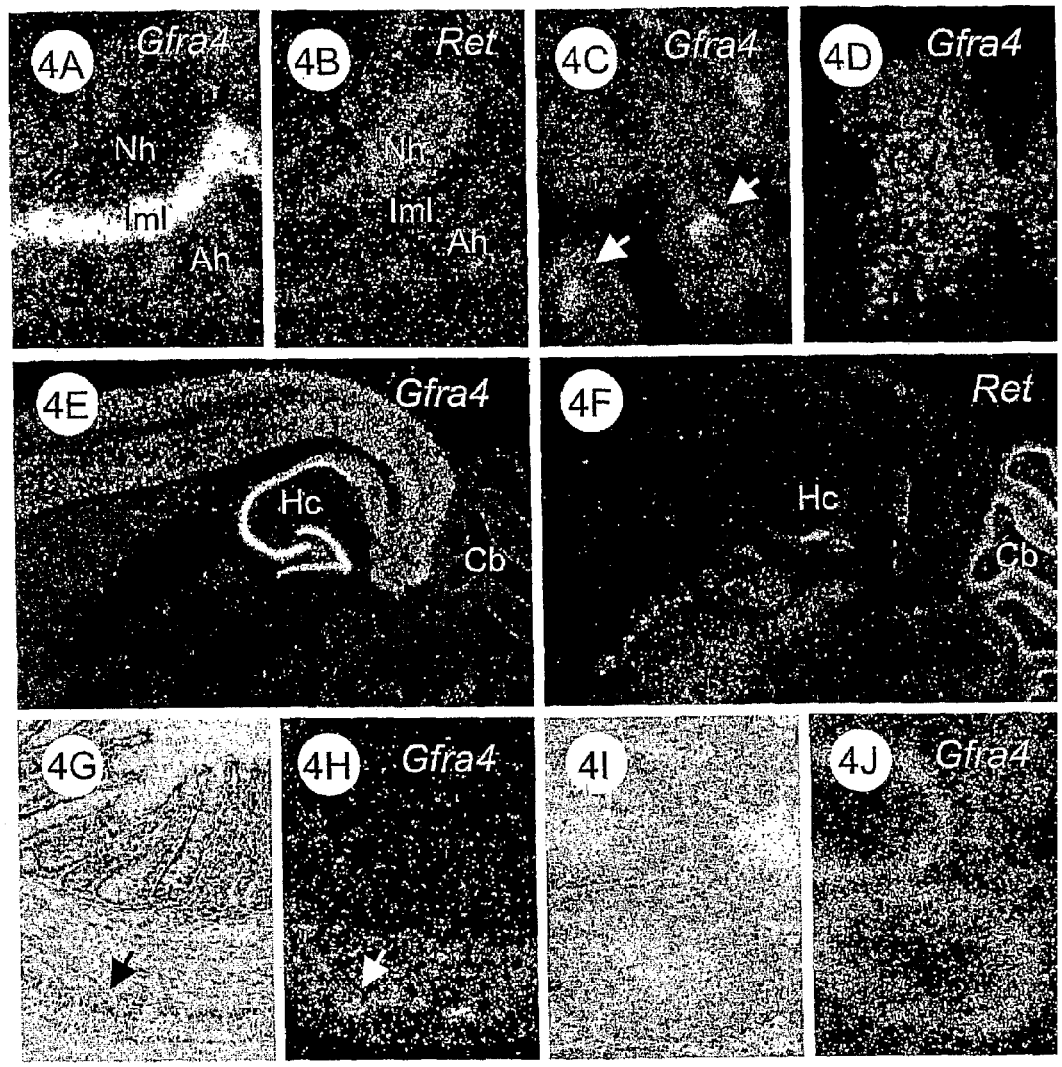

FIG. 4. Localization of Gfra4 and Ret mRNAs in developing and mature mouse tissues by in situ hybridization.

FIG. 4A. Gfra4 is highly expressed in the intermediate lobe (Iml) of E18 pituitary gland (sagittal section), while moderate Ret expression is seen in the neurohypophysis (Nh). Ah, adenohypophysis.

FIG. 4B. Gfra4 is highly expressed in the intermediate lobe (Iml) of E18 pituitary gland (sagittal section), while moderate Ret expression is seen in the neurohypophysis (Nh). Ah, adenohypophysis.

FIG. 4C. The condensing mesenchyme of developing limbs (arrows) shows moderate Gfra4 expression at E16.

FIG. 4D. Many neurons of adult spinal cord (coronal section) show moderate to high Gfra4 expression.

FIG. 4E. In adult brain (horizontal section), the distribution of Gfra4 and Ret mRNAs are not overlapping. Gfra4 is highest in the hippocampus (Hc). Cb, cerebellum.

FIG. 4F. In adult brain (horizontal section), the distribution of Gfra4 and Ret mRNAs are not overlapping. Gfra4 is highest in the hippocampus (Hc). Cb, cerebellum.

FIG. 4G. The circular muscle layer and the myenteric ganglia of the adult colon express Gfra4. H & E staining.

FIG. 4H. The circular muscle layer and the myenteric ganglia of the adult colon express Gfra4. Dark field image.

FIG. 4I. Seminiferous tubules in adult testis express Gfra4. H & E staining.

FIG. 4J. Seminiferous tubules in adult testis express Gfra4. Dark field image.

Figure 5:
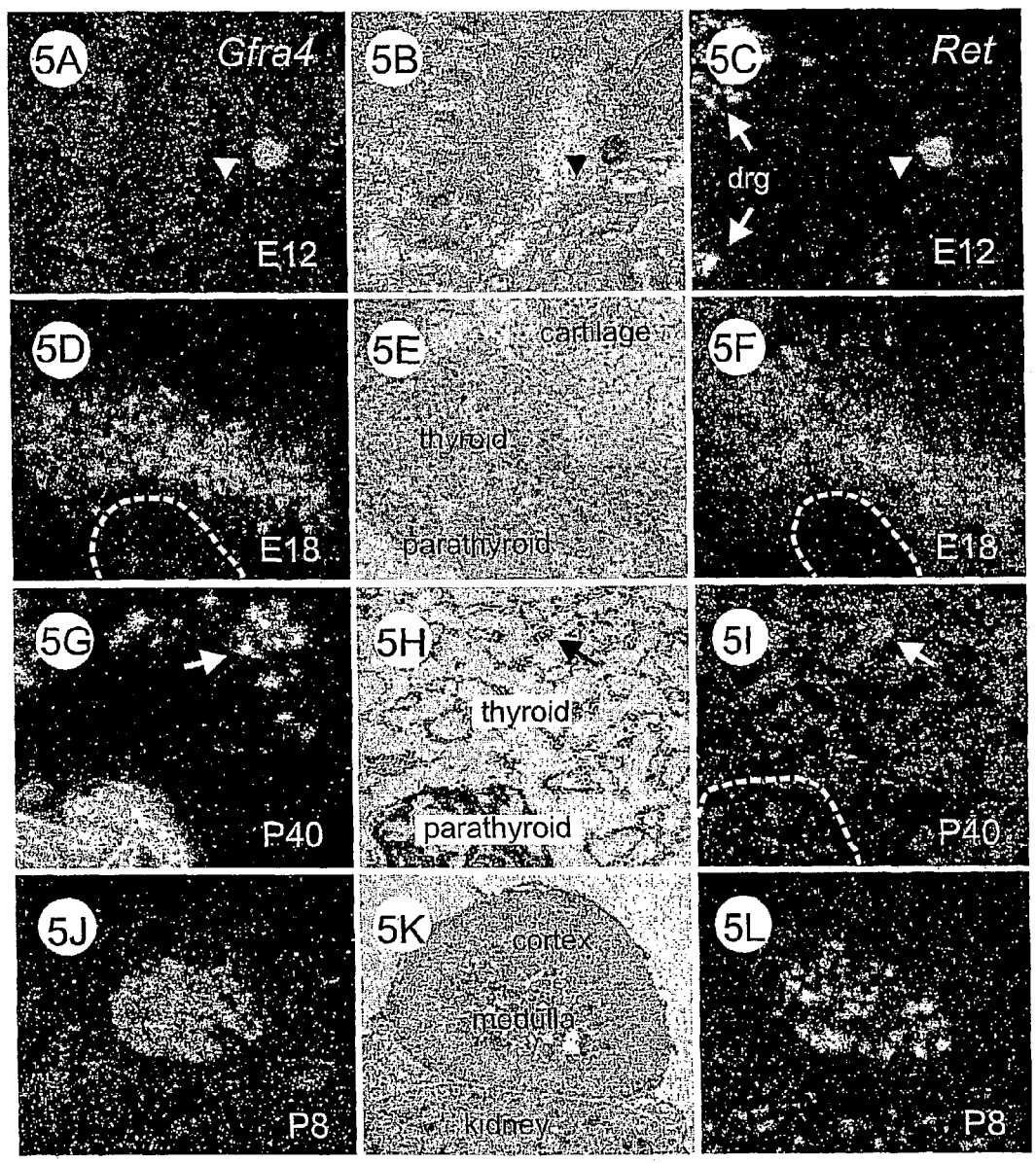

FIG. 5. Gfra4 and Ret are co-expressed in mouse thyroid C-cells and adrenal chromaffin cells.

FIG. 5A. In situ hybridization of adjacent sagittal sections of E12 mouse embryos for Gfra4 (FIG. 5A) and Ret (FIG. 5C). Arrowheads point to the ultimobranchial body. drg dorsal root ganglia.

FIG. 5B. In situ hybridization of adjacent sagittal sections of E12 mouse embryos for Gfra4 (FIG. 5A) and Ret (FIG. 5C). Arrowheads point to the ultimobranchial body. drg dorsal root ganglia.

FIG. 5C. In situ hybridization of adjacent sagittal sections of E12 mouse embryos for Gfra4 (FIG. 5A) and Ret (FIG. 5C). Arrowheads point to the ultimobranchial body. drg dorsal root ganglia.

FIG. 5D. Adjacent sagittal sections of E18 embryos hybridized for Gfra4 (FIG. 5D) and Ret (FIG. 5F). Both Gfra4 and Ret are expressed in the C-cells but not in the parathyroid gland (broken line).

FIG. 5E. Adjacent sagittal sections of E18 embryos hybridized for Gfra4 (FIG. 5D) and Ret (FIG. 5F). Both Gfra4 and Ret are expressed in the C-cells but not in the parathyroid gland (broken line).

FIG. 5F. Adjacent sagittal sections of E18 embryos hybridized for Gfra4 (FIG. 5D) and Ret (FIG. 5F). Both Gfra4 and Ret are expressed in the C-cells but not in the parathyroid gland (broken line).

FIG. 5G. In 6-week-old mice, Gfra4 is highly expressed in the thyroid parafollicular C-cells (arrow), but also in the parathyroid gland (broken line). In contrast, Ret expression is detectable only in the C-cells (arrow) but not in the parathyroid gland.

FIG. 5H. In 6-week-old mice, Gfra4 is highly expressed in the thyroid parafollicular C-cells (arrow), but also in the parathyroid gland (broken line). In contrast, Ret expression is detectable only in the C-cells (arrow) but not in the parathyroid gland.

FIG. 5I. In 6-week-old mice, Gfra4 is highly expressed in the thyroid parafollicular C-cells (arrow), but also in the parathyroid gland (broken line). In contrast, Ret expression is detectable only in the C-cells (arrow) but not in the parathyroid gland.

FIG. 5J. Gfra4 is highly expressed by all cells in adrenal medulla at postnatal day P8, while only a subpopulation of them express Ret.

FIG. 5K. Gfra4 is highly expressed by all cells in adrenal medulla at postnatal day P8, while only a subpopulation of them express Ret.

FIG. 5L. Gfra4 is highly expressed by all cells in adrenal medulla at postnatal day P8, while only a subpopulation of them express Ret. The bright-field images shown in FIGS. 5B, 5E, 5H, and 5K correspond to those in 5A, 5F, 5I and 5L, respectively.

Figure 6:
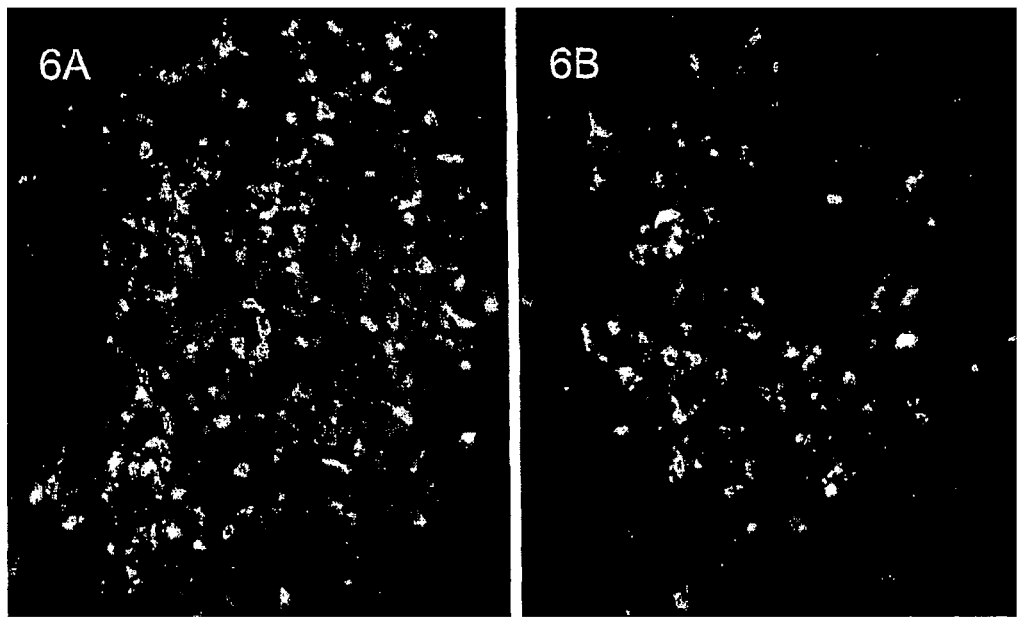

FIG. 6. Ret-deficient mice have less thyroid calcitonin-cells.

FIG. 6A. E18 thyroid glands from wild-type (FIG. 6A) and Ret-deficient (FIG. 6B) mice are immunostained for calcitonin. Shown are representative sections containing the highest number of labeled C-cells through the middle part of the thyroid gland. The remaining C-cells in Ret-deficient mice appear morphologically normal.

FIG. 6B. E18 thyroid glands from wild-type (FIG. 6A) and Ret-deficient (FIG. 6B) mice are immunostained for calcitonin. Shown are representative sections containing the highest number of labeled C-cells through the middle part of the thyroid gland. The remaining C-cells in Ret-deficient mice appear morphologically normal.

Figure 7:
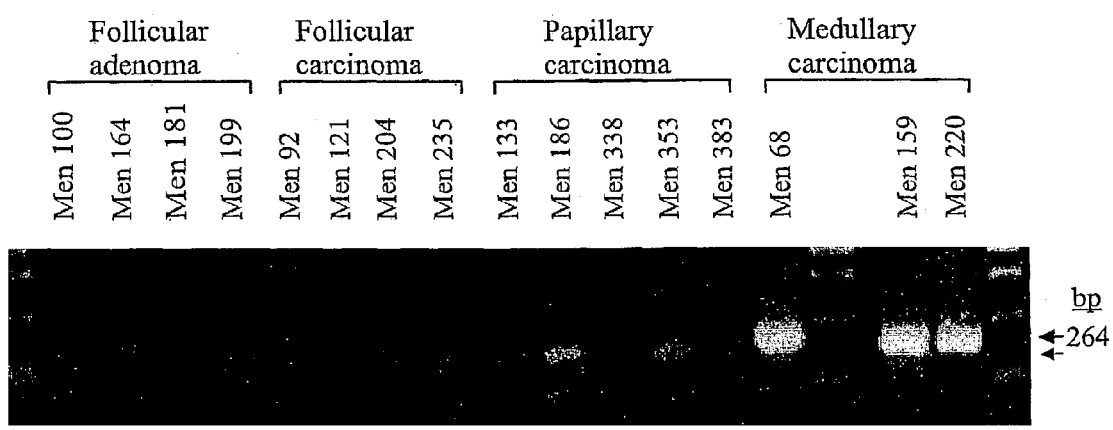

FIG. 7. RT-PCR analysis of GFRA4 expression in human thyroid tumors. Each line represents analysis of a tumor from a different patient. The specific 264 bp PCR product representing GFRA4 (exon 1a) expression is high in all medullary carcinoma samples (3/3) but not detectable in other thyroid tumours tested including, 4 follicular adenoma, 4 follicular carcinoma and 5 papillary carcinoma samples.

Figure 8:
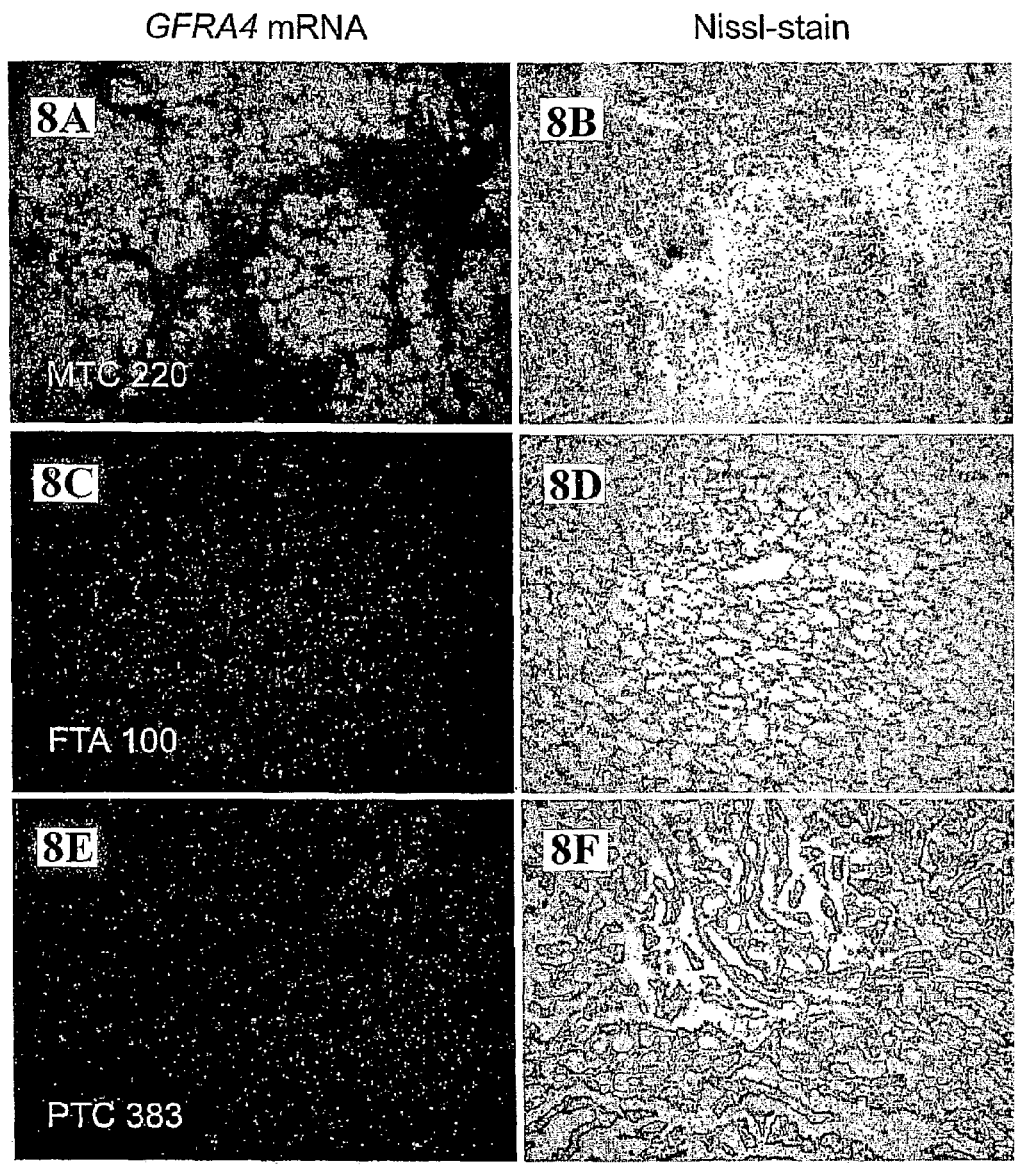

FIG. 8. Localization of human GFRA4 mRNA expression in medullary thyroid carcinoma but not in other thyroid tumors. In situ hybridization was performed using a human GFRA4 specific antisense cRNA probe on frozen sections.

FIG. 8A. GFRA4 is highly expressed by virtually all cells in the medullary thyroid carcinoma (MTC) but not in the surrounding connective tissue (dark field image).

FIG. 8B. Light-field image shows the Nissl-stained structure of tissue.

FIG. 8C. Other thyroid tumors, including follicular adenoma (FTA) (FIGS. 8C and 8D) and papillary carcinoma (PTC) (FIGS. 8E and 8F) show no GFRα4 expression above sense control levels (not shown).

FIG. 8D. Other thyroid tumors, including follicular adenoma (FTA) (FIGS. 8C and 8D) and papillary carcinoma (PTC) (FIGS. 8E and 8F) show no GFRα4 expression above sense control levels (not shown).

FIG. 8E. Other thyroid tumors, including follicular adenoma (FTA) (FIGS. 8C and 8D) and papillary carcinoma (PTC) (FIGS. 8E and 8F) show no GFRα4 expression above sense control levels (not shown).

FIG. 8F. Other thyroid tumors, including follicular adenoma (FTA) (FIGS. 8C and 8D) and papillary carcinoma (PTC) (FIGS. 8E and 8F) show no GFRα4 expression above sense control levels (not shown).

Figure 9:
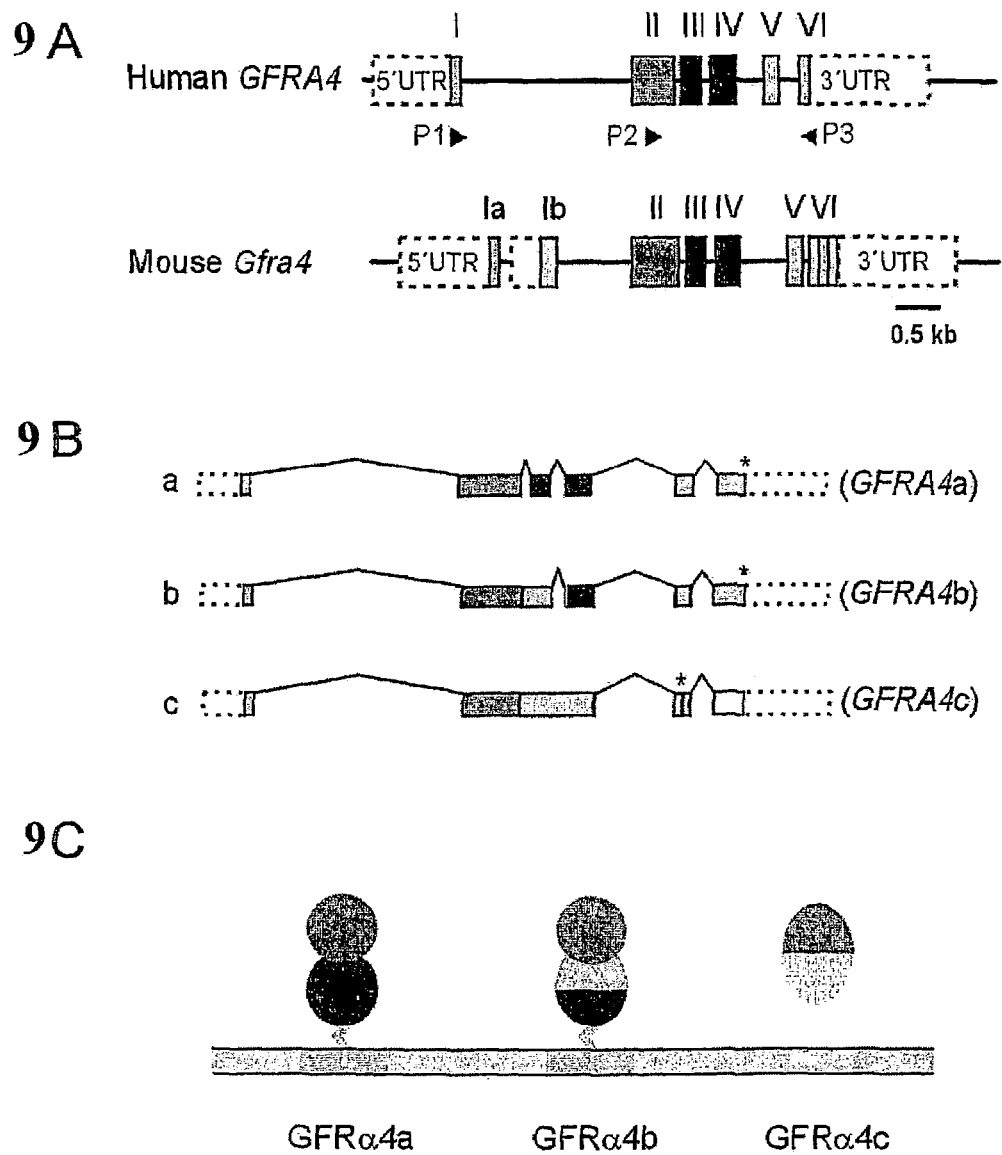
Figure 10:
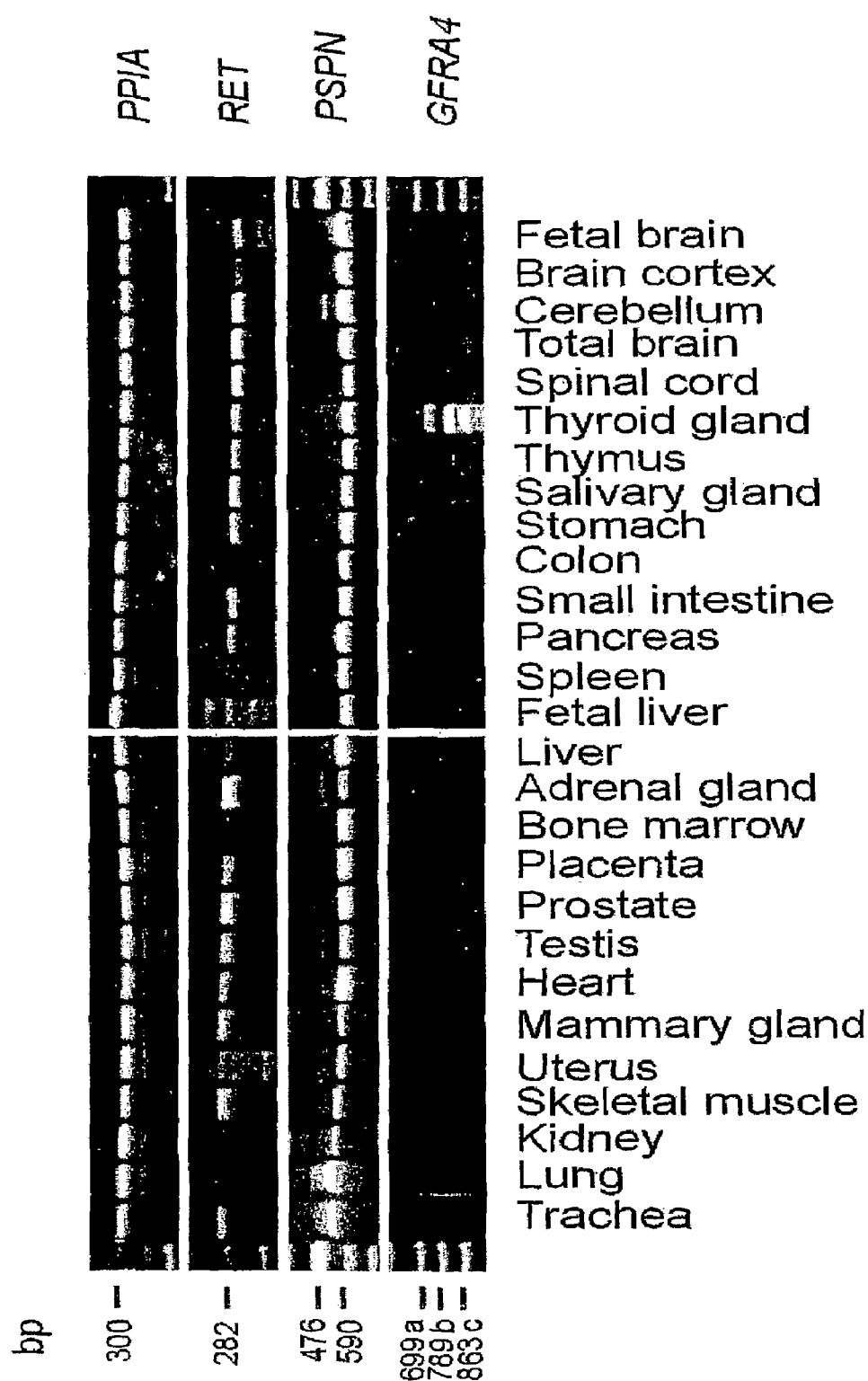

FIG. 9. Structure of the human GFRA4 gene compared to mouse Gfra4 and different splice forms of human GFRA4 mRNA.

FIG. 9A. Structure of the human GFRA4 gene (top) compared to mouse Gfra4 gene (bottom). Both contain at least 6 exons but no alternative exon 1b has been found in human. Also the putative transmembrane form encoded by the alternatively spliced exon 6 found in mouse is absent in human. Primers P1-P3, used in RT-PCR in FIGS. 2 and 5 are marked by arrowheads.

FIG. 9B. Splicing of GFRA4 gene in human thyroid gland. Two GPI-linked isoforms (GFRA4a and GFRA4b), and one putative soluble isoform (GFRA4c) are produced by alternative splicing. In transcript encoding for GFRα4a all the introns are spliced, whereas GFRα4b contains the intron between exon 2 and exon 3. Transcript encoding GFRα4c contain introns between exons 2 and 3 and between exons 3 and 4. Asterisk marks the stop codon.

FIG. 9C. Proposed schematic domain structure of human GFRα4 isoforms.

FIG. 10. RT-PCR analysis of GFRA4, PSPN and RET transcripts in various human tissues. Top row: GFRA4 expression is detected only in thyroid gland using primers P2 and P3 (see FIG. 15A). All the introns in the transcript corresponding to 699 bp are spliced. The 789 bp transcript contains a small intron between exon 2 and exon 3 and corresponds to the GFRα4b form. The 863 bp fragment contains introns between exons 2 and 3 and between exons 3 and 4, and corresponds to the soluble GFRα4c form. Second row: An unspliced transcript of the human PSPN is expressed in all tissues (approximately 590 bp, intron size not determined), whereas the spliced transcript (476 bp), which corresponds to the functional PSPN, is weakly expressed in cerebellum, adrenal gland and testis and barely detectable in spinal cord. To exclude DNA contamination in RT-PCR reactions, controls containing RNA were also subjected to PCR (not shown). Third row: RET expression (282 bp) is detectable in almost all human tissues examined but the expression levels are strongest in adult brain, cerebellum, spinal cord, salivary gland, adrenal gland and prostate. Bottom row: Control RT-PCR with PPIA transcript showing equal loading of cDNA. In all PCR experiments, negative water controls were included (not shown).

FIG. 11. Binding and Chemical Cross-linking of [$^{125}$I] PSPN to Human GFRα4 and Ret.

FIG. 11A. Displacement binding of [$^{125}$I]PSPN by PSPN, NRTN, GDNF and ARTN from human GFRα4a-expressing Neuro-2a cells, shown as percentage of [$^{125}$I]PSPN bound in the absence of a cold ligand (100%). One representative experiment out of four is shown.

FIG. 11B. Chemical cross-linking of [$^{125}$I]PSPN to vector- (lanes 1, 2) or hGFRA4a transfected (lanes 3-6) CHO cells, in the presence (lanes 2, 3, 5) or absence (lanes 1, 4, 6) of unlabeled PSPN, treated (lanes 3, 4) or not treated (lanes 1, 2, 5, 6) with PI-PLC. Bands are designated as follows: arrowhead, approximately 46 kD; arrow, approximately 62 kD; asterisk, approximately 92 kD.

FIG. 11C. Proteins cross-linked to [$^{125}$I]PSPN in the presence (lanes 1, 3) or absence (lanes 2, 4) of unlabeled PSPN in vector- (lanes 1, 2) or GFRA4a- (lanes 3, 4) transfected Neuro-2a cells. Bands are designated as in FIG. 11B.

FIG. 11D. Immunoprecipitation of Ret from vector- (lanes 1, 3) or GFRA4a-transfected (lanes 2, 4) Neuro-2a cells after chemical cross-linking of [$^{125}$I]PSPN, separated in the presence (lanes 1, 2) or absence (lanes 3, 4) of (β-mercaptoethanol (β-Me). Bands are designated as follows: arrowhead, approximately 46 kD; arrow, approximately 196 kD; diamond approximately 232 kD; asterisk, approximately 400 kD.

FIG. 11E. Phosphorylation of Ret in mock- (lanes 1, 2), GFRA4a- (lanes 3, 4, 5) or Gfra1-transfected Neuro-2a cells upon stimulation with 100 ng/ml of PSPN (lanes 2, 4, 5) or 100 ng/ml of GDNF (lane 7).

FIG. 11F. Dose-dependent phosphorylation of Ret with PSPN in hGFRA4a-transfected Neuro-2a cells.

FIG. 12. PSPN specifically promotes survival of RET/Gfra4-injected SCG neurons. Neonatal mouse SCG neurons were grown five days with NGF, injected with indicated plasmid mixtures (all 50:50 ng/μl), grown overnight with NGF, then NGF was changed for indicated factors (all 100 ng/ml). Numbers of viable neurons after 3-day treatment period are expressed relative to the number of initial neurons. Means ±s.e.m of three to seven independent repeats for each factor is shown. $p<0.05$ (*); $p<0.001$ (***).

FIG. 13. Semiquantitative RT-PCR analysis of GFRA4, PSPN and RET in different human thyroid tumors. Top row: GFRA4 mRNA is selectively expressed in medullary thyroid carcinomas (MTC). No GFRA4 transcripts are detectable in follicular thyroid adenomas (FTA), follicular thyroid carcinomas (FTC) or papillary thyroid carcinomas (PTC). Each lane represents tumor cDNA from different patient. Normal thyroid gland, including medullary tissue (NT) also expresses GFRA4. Two major transcripts of 831 and 910 bp seen in MTC and TT-cells correspond to GFRα4a and GFRα4b, respectively (primers P1 and P3, see FIG. 15A). The minor transcript of 999 bp corresponds to the soluble GFRα4c. Second row: No spliced form of the PSPN transcript is detectable using primers covering the initiation and the stop codons. Third row: RET mRNA is expressed in all MTC samples. Bottom row: Control RT-PCR with PPIA transcript showing equal loading of cDNA. All experiments contained negative water controls (not shown).

FIG. 14. Localization of GFRA1, GFRA2 GFRA3, GFRA4 and RET mRNAs in thyroid tumors by in situ hybridization.

FIG. 14A. Typical representative examples of autoradiography films showing GFRA1-GFRA4 and RET cRNA hybridization to adjacent frozen sections of different thyroid tumors. Of the four types of tumors represented, only the MTC sections were strongly stained for GFRA4 and RET expression. GFRA1, GFRA2, GFRA3 mRNA levels were very low or undetectable in all samples including MTC.

FIG. 14B. GFRA4 and RET probes were hybridized to frozen sections representing follicular thyroid adenoma (FTA), follicular thyroid carcinoma (FTC), papillary thyroid carcinoma (PTC), and medullary thyroid carcinoma (MTC) samples and sections were counter-stained by Nissl-substance. GFRA4 and RET is highly expressed in all malignant cells of the MTC sample but not in the surrounding connective tissue. Bar in A=0.5 cm, in B=100 μm.

FIG. 15. Activation of Akt in Neuro-2a cells expressing either GFRα1 or hGFRα4 with their respective ligands.

FIG. 15A. Neither GDNF nor PSPN (native or heat-inactivated) stimulate Akt phosphorylation in mock-transfected Neuro-2a cells. In Neuro-2a cells expressing GFRα1, GDNF, but not PSPN evokes Akt phosphorylation.

FIG. 15B. PSPN, but not GDNF, stimulates Akt phosphorylation in Neuro-2a cells expressing GFRα4. Upper panels in FIG. 15A and FIG. 15B show immunoblotting of the cell lysates with anti phospho-Akt (Ser 473) antibodies. Lower panels show the re-probing of the same blots with phosphorylation state-independent anti Akt antibodies.

Figure 16:
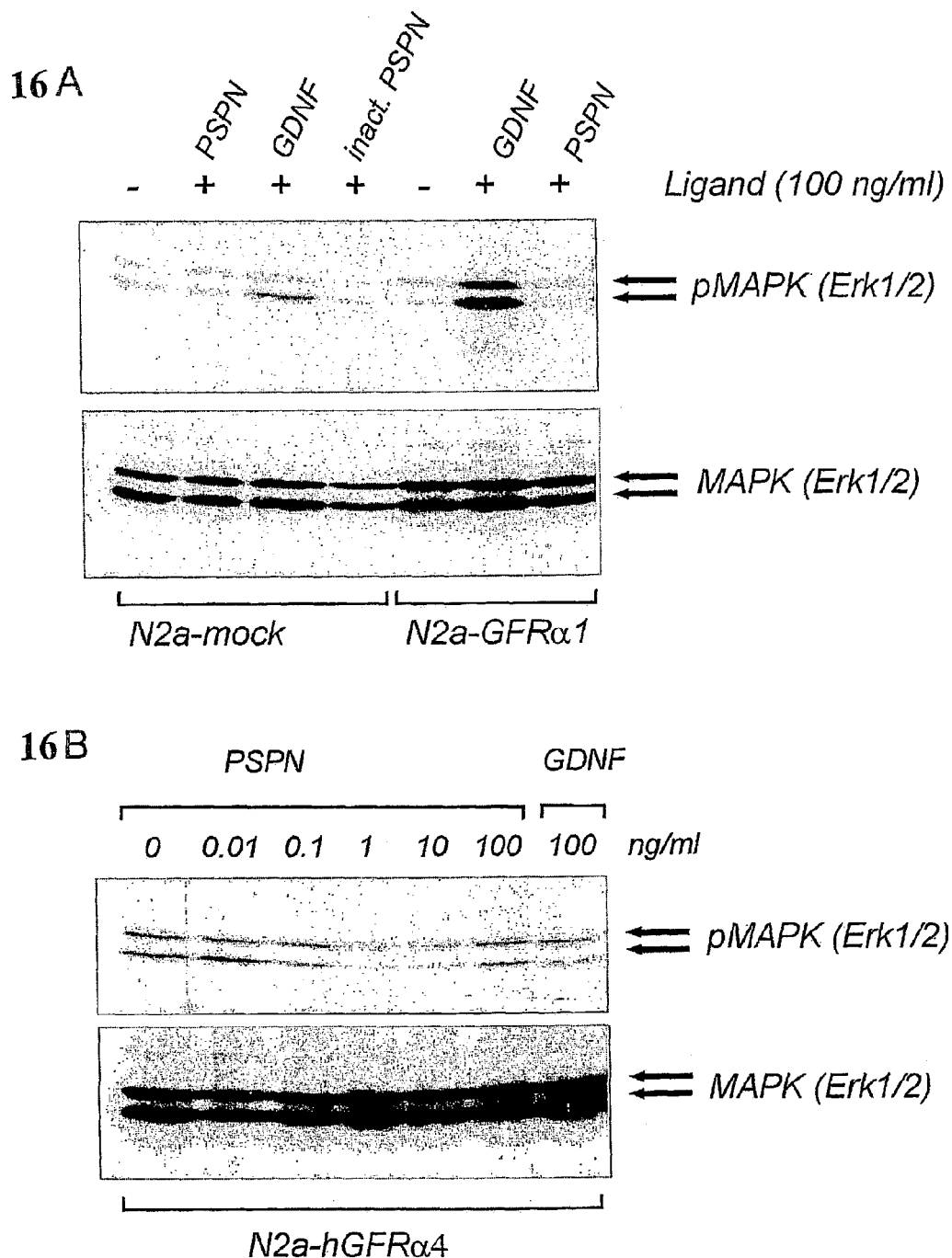

FIG. 16. MAP kinases are activated in response to GDNF but not to PSPN in the Neuro-2a cells.

re-probing of the same blots with phosphorylation state-independent anti MAPK antibodies.

FIG. 17A. GDNF and PSPN both stimulate cell survival in dose-dependent manner via their respective receptors in serum-free conditions.

FIG. 17B. PSPN, in contrast to GDNF, cannot induce neurite outgrowth in Neuro-2a/hGFRα4 cells. Shown are mean values with SEM. —$P<0.01$; *—$P<0.001$.

FIG. 18. cDNA and amino-acid sequences of mouse GFRα4 GPI-isoform a1. The GPI-linked isoform, (cf. FIG. 1A) corresponds to transcript a1 in FIG. 2C. The signal sequence encoded by exon 1a is underlined (SEQ ID NO:7 and SEQ ID NO:1).

FIG. 19. The putative TM-anchored isoform, GFRα4-a2, encoded by transcript a2 in FIG. 2C (SEQ ID NO:8 and SEQ ID NO:2).

FIG. 20. cDNA and amino-acid sequence of GFRα4-a3/4, a soluble isoform of mouse GFRα4. The signal sequence encoded by exon 1a is underlined. GFRα4-a3/4 is encoded by transcripts a3-a4 as shown in FIG. 2C (SEQ ID NO:9 and SEQ ID NO:3).

FIG. 21. Shown are the cDNA and amino-acid sequence of human GFRα4 a GPI-linked isoform a (SEQ ID NO:10 and SEQ ID NO:4).

FIG. 22. Human GFRα4 b, putative GPI-linked isoform b (SEQ ID NO:11 and SEQ ID NO:5).

FIG. 23. Human GFRα4 c, a putative secreted isoform, formed by alternative splicing of the second short intron (SEQ ID NO:12 and SEQ ID NO:6).

FIG. 24. Genomic sequence of human GFRA4 locus. The coding sequences are in uppercase. Intronic sequences are in lower-case and bold. The alternatively spliced 3'-end of the $2^{nd}$ short intron is shown in italics (SEQ ID NO:13).

TABLE 1

Expression of Gfra4 and Ret mRNAs in Selected Mouse Tissues and Cells

| Age | E12 | | E16 | | P0 | | P20 | | adult | |
|---|---|---|---|---|---|---|---|---|---|---|
| Area | Gfra4 | Ret | Gfra4 | Ret | Gfra | Ret | Gfra4 | Ret | Gfra4 | Ret |
| NC | ± | − | ++ | − | ++ | − | nd | nd | ++ | − |
| HC | nd | nd | nd | nd | ++ | − | nd | nd | +++ | + |
| VM | + | +++ | nd | nd | + | +++ | nd | nd | + | +++ |
| VSC | + | +++ | ++ | +++ | + | +++ | nd | nd | + | +++ |
| PNS | ± | +++ | + | +++ | ++ | +++ | ++ | +++ | ++ | +++ |
| PI | nd | nd | +++ | − | +++ | − | +++ | nd | +++ | − |
| TC | ++ | ++ | +++ | ++ | +++ | ++ | +++ | ++ | +++ | + |
| PT | nd | nd | − | − | ± | − | +++ | − | +++ | − |
| AdM | nd | nd | nd | nd | ++ | ++* | ++ | + | ++ | +* |
| Kidney | + | +++ | + | +++ | ± | +++ | − | + | − | ± |
| Lung | + | + | + | + | ± | − | nd | nd | − | − |
| Liver | − | − | − | − | − | − | nd | nd | − | − |
| Testis | nd | nd | nd | nd | + | ++* | ++ | ± | ++ | ± | mRNA expression was graded from −, no labeling above background, to +++, highest detected expression level based on visual inspection of in situ hybridization sections.
Expression of Gfra4 and Ret at E14 and E16 as well as P8 and P20 were overlapping.
*Expression differs from that reported by Golden et al., 1999.

FIG. 16A. Neither GDNF, nor PSPN (native or heat-inactivated), stimulate MAPK phosphorylation in mock-transfected Neuro-2a cells. In Neuro-2a/GFRα1 cells GDNF, but not PSPN, activates MAPK.

FIG. 16B. In Neuro-2a/hGFRα4 cells PSPN is unable to stimulate phosphorylation of MAPK. Upper panels in FIG. 16A and FIG. 16B show immunoblotting of the cell lysates with anti phospho-MAPK antibodies. Lower panels show the

ABBREVIATIONS

IML, intermediate lobe; nd, not determined; PNS, peripheral nervous system including sensory (DRG), sympathetic (SGG) and enteric ganglia; NC, Neocortex; HC, Hippocampus; VM, Ventral Midbrain; VSC, Ventral Spinal Cord; PNS, PNS ganglia; PI, Pituitary (IML); TC, Thyroid (C-cells); PT, Parathyroid; AdM, Adrenal Medulla; nd, not determinated.

TABLE 2

Expression of human GFRA1, GFRA2, GFRA3, GFRA4 and RET in thyroid tumours and normal thyroid

| Tumour | GFRA1 RT | GFRA1 In situ | GFRA2 RT | GFRA2 In Situ | GFRA3 RT | GFRA3 In situ | GFRA4 RT | GFRA4 In situ | RET RT | RET In situ |
|---|---|---|---|---|---|---|---|---|---|---|
| FTA | + | + | + | + | + | + | – | – | – | – |
|  | 1/4 | 1/2 | 3/4 | 2/2 | 4/4 | 2/2 | 0/4 | 0/3 | 0/4 | 0/2 |
| FTC | + | – | + | + | + | + | – | – | – | – |
|  | 1/4 | 0/1 | 2/4 | 1/1 | 2/4 | 1/2 | 0/4 | 0/3 | 0/4 | 0/1 |
| PTC | + | – | + | + | + | + | – | – | – | – |
|  | 2/5 | 0/2 | 3/5 | 2/2 | 2/5 | 1/3 | 0/5 | 0/4 | 0/5 | 0/2 |
| MTC | + | + | + | + | + | + | +++ | +++ | +++ | +++ |
|  | 5/8 | 4/6 | 7/8 | 4/6 | 4/8 | 2/6 | 8/8 | 6/6 | 8/8 | 6/6 |
| NT | + | Nd | + | Nd | + | Nd | ++ | Nd | ++ | Nd |
|  | 1/1 |  | 1/1 |  | 2/3 |  | 1/3 |  | 1/1 |  |
| TT cells | + | Nd | – | Nd | – | Nd | +++ | Nd | +++ | Nd | mRNA expression is graded from –, no labelling above background, to +++, highest detected expression based on visual inspection. The numbers below the tissue gradings denote the number of samples positive/total number of samples analyzed.

ABBREVIATIONS

RT, RT-PCR; FTA, follicular thyroid adenoma; FTC, follicular thyroid carcinoma; PTC, papillary thyroid carcinoma; MTC, medullary thyroid carcinoma; NT, normal thyroid; Nd, not determined.

REFERENCES

Acton, D. S. et al., 2000. Oncogene 19: 3121-3125
Airaksinen, M. S. et al., 1999. Mol. Cell. Neurosci. 13: 313-325
Angrist, M. et al., 1998. Genomics 48: 354-362
D' Arcangelo, G. et al., 1993. Mol. Cell. Biol. 13: 3146-3155
Ashcroft et al., 1999. Oncogene 18: 4586-4597
Baloh, R. H. et al., 1998. Proc. Natl. Acad. Sci. USA
Baloh, R. H. et al., 1998. Neuron 21: 1291-1302
Baloh, R. H. et al., 2000. Curr. Opin. Neurobiol. 10: 103-110
Belluardo, N. et al., 1999. Cell Tissue Res 295: 467-475
Bilak, M. M. et al., 1999. Mol. Cell. Neurosci. 13: 326-336
Bongarzone, I. et al., 1998. Oncogene 16: 2295-2301
Borrello et al., 1995. Oncogene 11: 2419-24177
Califano et al., 1995. Oncogene 11: 107-112
Califano et al., 2000. J Biol Chem 275: 19297-305
Carlomagno, F. et al., 1998. Endocrinology 139: 3613-3619
Carson-Walter et al., 1998. Oncogene 17: 367-376
Durbec, P. L. et al., 1996. Development 122: 349-358
Edery, P. et al. 1997. Bioassays 19: 385-395
Eng, C., 1999. J. Clin. Oncol. 17: 380-394
Enokido, Y. et al., 1998. Curr. Biol. 8: 1019-1022
Frisk, T. et al., 2000. Eur. J. Endocrinol. 142: 643-649
Golden, J. P. et al., 1999. Exp. Neurol. 158: 504-528
Grabowski, P. J., 1998. 92: 709-712
Gunn, T. M. et al., 1999. Nature 398: 152-156
Ho, T. W. et al., 2000. Exp. Neurol. 161: 664-675
Iwashita, T. et al., 1996. Oncogene 12: 481-487
Jaszai, J. et al., 1998. J. Neurosci. Res. 53: 494-501
Jing, S. et al., 1996. Cell 85: 1113-1124
Kaplan, D. R. and Miller, F. D. 2000. Curr. Opin. Neurobiol. 10(3):381-391
Kazlauskas, A. 1994. Curr. Opin. Genet. Dev. 4: 5-14
Klein, R. D. et al., 1997. Nature 387: 717-721
Laurikainen, A. et al., 2000. J. Neurobiol. 43: 198-205
Leitner, M. L. et al., 1999. J. Neurosci. 19: 9322-9331
Lindahl, M. et al., 2000. Mol. Cell. Neurosci. 15: 522-533
Lopez, A. J., 1998. Annu. Rev. Genet. 32: 279-305
Lorenzo, M. J. et al., 1995. Oncogene 10: 1377-1383
Lou, H. et al., 1998. J. Endocrinol. 156: 401-405
Masure, S. et al., 2000. J. Biol. Chem. (in press).
McGonigle, P. et al., 1994. Basic Neurochemistry, 5th Ed. Ed. Siegel, G. J. Raven Press, NY: 209-230
Michiels, F.-M. et al., 1997. Proc. Natl. Acad. Sci. USA 94:
Milbrandt, J. et al., 1998. Neuron 20: 245-253
Murakami et al., 1999. Biochem Biophys Res Commun 262: 68-75
Nakagawa et al., 1987. Proc Natl Acad Sci USA 84: 5923-5927
Nakamura, T. et al., 1994. J. Pathol. 172: 255-260
Pachnis, V. et al., 1993. Development 119: 1005-1017
Pearse, A. G. et al., 1976. Nature 214: 929-930
Pearse, A. G. et al., 1999. Histochemie 27: 96-102
Perron et al., 1999. Mol Cell Neurosci 13: 362-378
Ponder, B. A., 1999. Cancer Res. 59: 1736s-1741s
Rossel et al., 1997. Oncogene 14: 265-275
Rossi, J. et al., 1999. Neuron 22: 243-252
Sanicola, M. et al., 1997. Proc. Natl. Acad. Sci. 94:
Santoro, M. et al., 1990. Oncogene 5: 1595-1598
Santoro, M. et al., 1995. Science 267: 381-383
Segouffin-Cariou et al., 2000. J Biol Chem 275: 3568-3576
Smith-Hicks, C. L. et al., 2000. EMBO J. 19: 612-622
Thompson, J. et al., 1998. Neurosci. 11: 117-126
Timmusk, T. et al., 1993. Eur. J. Neurosci. 5: 605-613
Trupp, M. et al., 1998. Mol. Cell. Neurosci. 11: 47-63
Tsuzuki, T. et al., 1995. Oncogene 10: 191-198
Udenfriend, S. et al., 1995. Annu. Rev. Biochem. 64: 563-591
Widenfalk, J. et al., 1998. Eur. J. Neurosci. 10: 1508-1517

What is claimed is:

1. An isolated and purified nucleic acid sequence, wherein the nucleic acid sequence is a cDNA encoding a splicing isoform of mammalian GFRα4 consisting of the amino acid sequence SEQ ID NO:4, SEQ ID NO:5 or SEQ ID NO:6 having a functional activity of GFRα4, wherein the functional activity of GFRα4 comprises interacting with neurotrophic factor persephin or tyrosinase kinase receptor RET.

2. The nucleic acid sequence according to claim 1, wherein the nucleic acid sequence is a cDNA encoding a splicing isoform of human GFRα4 consisting of the amino acid sequence SEQ ID NO:4, SEQ ID NO:5 or SEQ ID NO:6 having a functional activity of GFRα4, wherein the functional activity of GFRα4 comprises interacting with neurotrophic factor persephin or tyrosinase kinase receptor RET.

3. An isolated and purified nucleic acid sequence, wherein the nucleic acid sequence is a cDNA encoding a splicing isoform of mammalian GFRα4 consisting of the sequence SEQ ID NO:10, SEQ ID NO:11, SEQ ID NO:12 or SEQ ID NO:13 encoding a polypeptide having a functional activity of GFRα4, wherein the functional activity of GFRα4 comprises interacting with neurotrophic factor persephin or tyrosinase kinase receptor RET.

4. A purified and isolated polypeptide, wherein the polypeptide comprises a polypeptide consisting of the amino acid sequence SEQ ID NO:4, SEQ ID NO:5, or SEQ ID NO:6.

5. The nucleic acid sequence according to claim 1, wherein the nucleic acid sequence is a cDNA encoding a splicing isoform of human GFRα4 consisting of the amino acid sequence SEQ ID NO:4 having a functional activity of GFRα4, wherein the functional activity of GFRα4 comprises interacting with neurotrophic factor persephin or tyrosinase kinase receptor RET.

6. The nucleic acid sequence according to claim 1, wherein the nucleic acid sequence is a cDNA encoding a splicing isoform of human GFRα4 consisting of the amino acid sequence SEQ ID NO:5 having a functional activity of GFRα4, wherein the functional activity of GFRα4 comprises interacting with neurotrophic factor persephin or tyrosinase kinase receptor RET.

7. The nucleic acid sequence according to claim 1, wherein the nucleic acid sequence is a cDNA encoding a splicing isoform of human GFRα4 consisting of the amino acid sequence SEQ ID NO:6 having a functional activity of GFRα4, wherein the functional activity of GFRα4 comprises interacting with neurotrophic factor persephin or tyrosinase kinase receptor RET.

8. The nucleic acid sequence according to claim 3, wherein the nucleic acid sequence is a cDNA consisting of the sequence SEQ ID NO:10 encoding a polypeptide having a functional activity of GFRα4, wherein the functional activity of GFRα4 comprises interacting with neurotrophic factor persephin or tyrosinase kinase receptor RET.

9. The nucleic acid sequence according to claim 3, wherein the nucleic acid sequence is a cDNA consisting of the sequence SEQ ID NO:11 encoding a polypeptide having a functional activity of GFRα4, wherein the functional activity of GFRα4 comprises interacting with neurotrophic factor persephin or tyrosinase kinase receptor RET.

10. The nucleic acid sequence according to claim 3, wherein the nucleic acid sequence is a cDNA consisting of the sequence SEQ ID NO:12 encoding a polypeptide having a functional activity of GFRα4, wherein the functional activity of GFRα4 comprises interacting with neurotrophic factor persephin or tyrosinase kinase receptor RET.

11. The nucleic acid sequence according to claim 3, wherein the nucleic acid sequence is a cDNA consisting of the sequence SEQ ID NO:13 encoding a polypeptide having a functional activity of GFRα4, wherein the functional activity of GFRα4 comprises interacting with neurotrophic factor persephin or tyrosinase kinase receptor RET.

12. An isolated and purified nucleic acid sequence, wherein the nucleic acid sequence is a cDNA encoding a splicing isoform of human GFRα4 consisting of the SEQ ID NO:10, SEQ ID NO:11, SEQ ID NO:12 OR SEQ ID NO:13 that encodes the amino acid sequences of SEQ ID NO:4, SEQ ID NO:5 or SEQ ID NO:6 having human GFRα4 receptor activity, wherein the functional activity of GFRα4 comprises interacting with neurotrophic factor persephin or tyrosinase kinase receptor RET.

* * * * *